US008388982B2

(12) United States Patent
Kong et al.

(10) Patent No.: US 8,388,982 B2
(45) Date of Patent: Mar. 5, 2013

(54) PHOTO-INDUCED DAMAGE MITIGATING AGENTS AND PREPARATION AND METHODS OF USE THEREOF

(75) Inventors: Xiangxu Kong, Foster City, CA (US); Gene Shen, Santa Clara, CA (US); Andrei Fedorov, San Mateo, CA (US); John Lyle, Fremont, CA (US); Grace Lee, San Ramon, CA (US); Lubomir Sebo, Redwood City, CA (US); Duc Do, San Jose, CA (US); Robert Weber, Mountain View, CA (US); Stephen Dudek, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 469 days.

(21) Appl. No.: 12/622,375

(22) Filed: Nov. 19, 2009

(65) Prior Publication Data

US 2010/0136592 A1 Jun. 3, 2010

Related U.S. Application Data

(60) Provisional application No. 61/116,048, filed on Nov. 19, 2008.

(51) Int. Cl.
*A61K 9/00* (2006.01)
*A61K 8/00* (2006.01)
*A61F 13/00* (2006.01)
*C12Q 1/68* (2006.01)
*C12Q 1/48* (2006.01)
*C12Q 1/02* (2006.01)

(52) U.S. Cl. ........... 424/400; 424/59; 424/422; 435/6.1; 435/15; 435/29

(58) Field of Classification Search .................. None
See application file for complete search history.

(56) References Cited

U.S. PATENT DOCUMENTS

| | | | |
|---|---|---|---|
| 2,511,428 | A | 6/1950 | Buxton et al. |
| 3,986,980 | A | 10/1976 | Cort |
| 4,003,919 | A | 1/1977 | Scott et al. |
| 4,302,569 | A | 11/1981 | Halle et al. |
| 5,242,835 | A | 9/1993 | Jensen |
| 6,068,848 | A | 5/2000 | Gubernick et al. |
| 7,235,357 | B2 | 6/2007 | Iwaki |
| 7,351,397 | B2 | 4/2008 | Cyr |
| 2002/0037479 | A1 | 3/2002 | Schwartzkopf et al. |
| 2003/0044830 | A1 | 3/2003 | Iwaki |
| 2003/0129642 | A1 | 7/2003 | Buechler et al. |
| 2007/0128133 | A1 | 6/2007 | Eid et al. |
| 2007/0161017 | A1 | 7/2007 | Eid et al. |
| 2008/0176241 | A1 | 7/2008 | Eid et al. |
| 2008/0176316 | A1 | 7/2008 | Eid et al. |

OTHER PUBLICATIONS

Grams, G.W. "Oxidation of alpha-tocopheroi by singlet oxygen" Tetrahedron Lett (1971) 50:4823-4825.
Kitajima, J. et al. "Constitutents of *Ficus pumila* leaves" Chem Pharm Bull (1998) 46(10):1647-1649.
International Search Report from Corresponding PCT Application PCT/US2009/065222 filed Nov. 19, 2009 issued Aug. 6, 2010.
International Preliminary Report on Patentability from Corresponding PCT Application PCT/US2009/065222 filed Nov. 19, 2009 issued Jun. 3, 2011.
Barra, et al. (2003) "Triplet State Dynamics within Cyclodextrin Solid Complexes." Arkivoc, 4:48-58.
Chen, et al. (2006) "Benzopyrans, Biphenyls and Xanthones from the Root of *Garcinia linii* and Their Activity Against *Mycobacterium tuberculosis*." Plant Medica 72:473-477.
Chen, et al. (2006) "New Cytotoxic Tetrahydrofuran- and Dyhydrofuran- Type Lignans from the Stem of BEilSchmiedia Tsangii." Plant Medica 72:351-357.
Chen, et al. (2007) "Anti-inflammatory Benzenoids from *Antrodia camphorate*." J. Natural Products 70(6):989-992.
Chen, et al. (2007) "Tocopherols and Triterpenoids from Sida Acute." J. Chinese Chemical Society 54(1):41-45.
Chiang, et al. (2003) "Two Novel α-Tocopheroids from the Aerial Roots of *Ficus microcarpa*." Tetrahedron Letters 44(27):5125-5128.
Cordes et al. (2009) "On the Mechanism of Trolox as Antiblinking and Antibleaching Reagent." J Am Chem Soc 131: 5018-5019.
D'Ischia, et al. (1991) "Dye-Sensitized Photooxidation of Vitamin E Revisited. New 7-Oxaspiro[ 4. Sldec-1 -ene-3,6-dione Products by Oxygenation and Ring Contraction of a-Tocopherol." J. Am. Chem. Soc. 113: 8353-8356.
Friaa, et al. (2006) "Kinetics of the Reaction Between the Antioxidant Trolox and the Free Radical DPPH in Semi-Aqueous Solution." Org Biomol Chem 4:2417-2423.
Gao, et al. (2008) "Chemical Constituents from Leaves of Allelopathic Cultivar Sunflower in China." Chemistry of Natural Compounds 44(6):773-775.
Gazdaru, D. (2001) "Characterization of the Fluorescence Quenching of Chlorophyll a by 1, 4 Benzoquinone Using the Nonlinear Analysis." J Optoelec Adv Mat 3(1):145-148.
Ham, et al. (1997) "Antioxidant Reactions of Vitamin E in the Perfused Rat Liver: Product Distribution and Effect of Dietary Vitamin E Supplementation." Archives of Biochem and Biophys 339(1):157-164.
Lin, et al. (2003) "Anti-Platelet Aggregation and Chemical Constituents from the Rhizome of Gyura Japonica." Plant Medica 69:757-764.
Matsuo, et al. (1987) "Oxygenations of Vitamin E (a-Tocopherol) and Its Model Compound 2,2,5,7,8-Pentamethylchroman-6-0i1n the Presence of the Superoxide Radical Solubilized in Aprotic Solvents: Unique Epoxidations and Recyclizations." J. Org. Chem. 52:3514-3520. Nonell, S. et al. (1995) "Solvent Influence on the Kinetics of the Photodynamic Degradation of Trolox, a Water-Soluble Model Compound for Vitamin E." J. Photochemistry and Photobiology B: Biology 29: 157-162.
Rasnik, et al. (2006) "Nonblinking and Longlasting Single-Molecule Fluorescence Imaging." Nature Methods 3(11):891-893.
Sapino, et al. (2008) "On the Complexation of Trolox with Methylb-Cyclodextrin: Characterization, Molecular Modelling and Photostabilizing Properties." J Incl Phenom Macrocycl Chem 62(1-2):179-186.
Schwille, Haustein E. (2001) Fluorescence correlation spectroscopy. An introduction to its concepts and applications. Biophysics Textbook Online. pp. 1-33.

*Primary Examiner* — Michael G Hartley
*Assistant Examiner* — Sun Y Kim
(74) *Attorney, Agent, or Firm* — Deana A. Arnold

(57) ABSTRACT

Compositions, devices, systems and methods for reducing and/or preventing photo-induced damage of one or more reactants in an illuminated analytical reaction by addition of one or more photo-induced damage mitigating agents to the reaction mixture and allowing the reaction to proceed for a period that is less than a photo-induced damage threshold period.

25 Claims, 35 Drawing Sheets

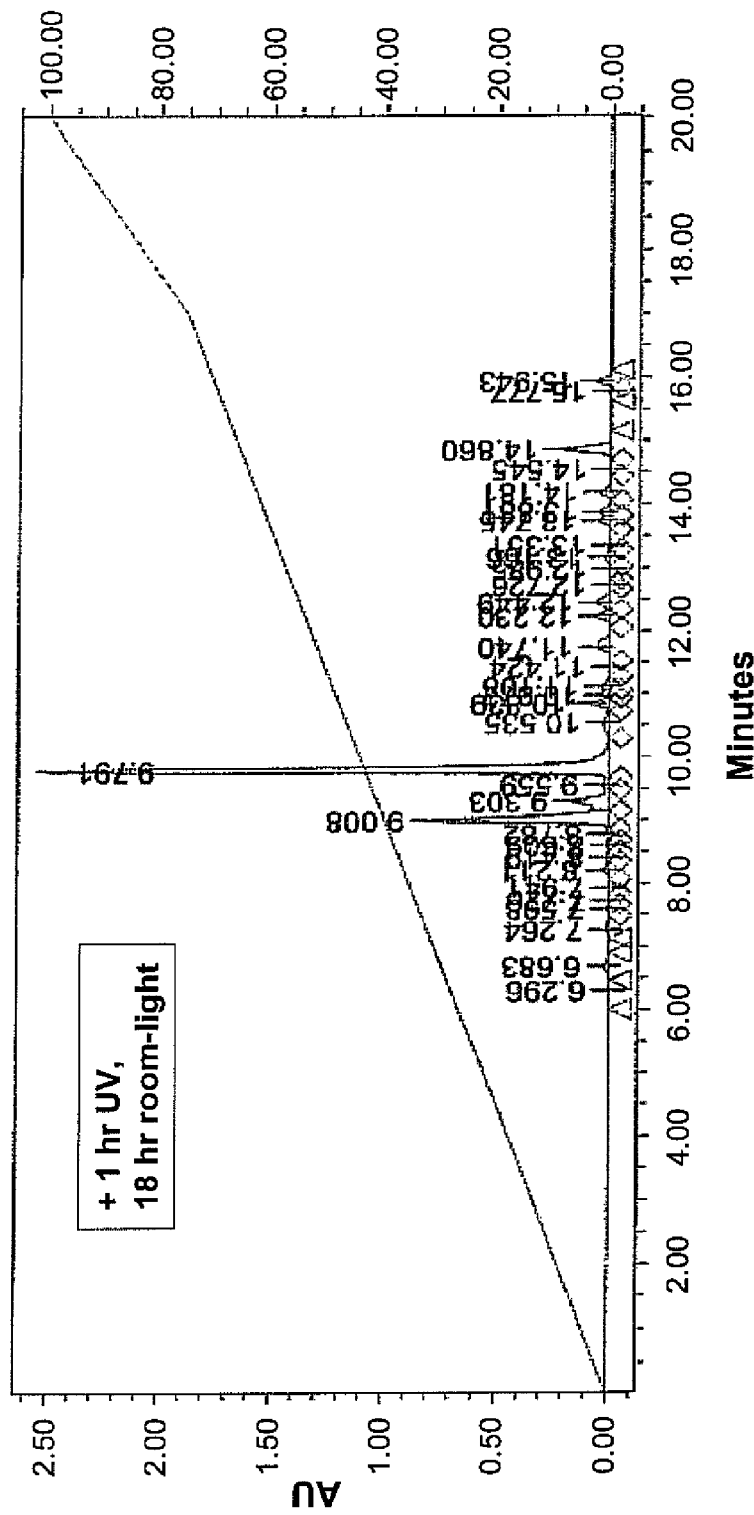
Figure 10, cont.

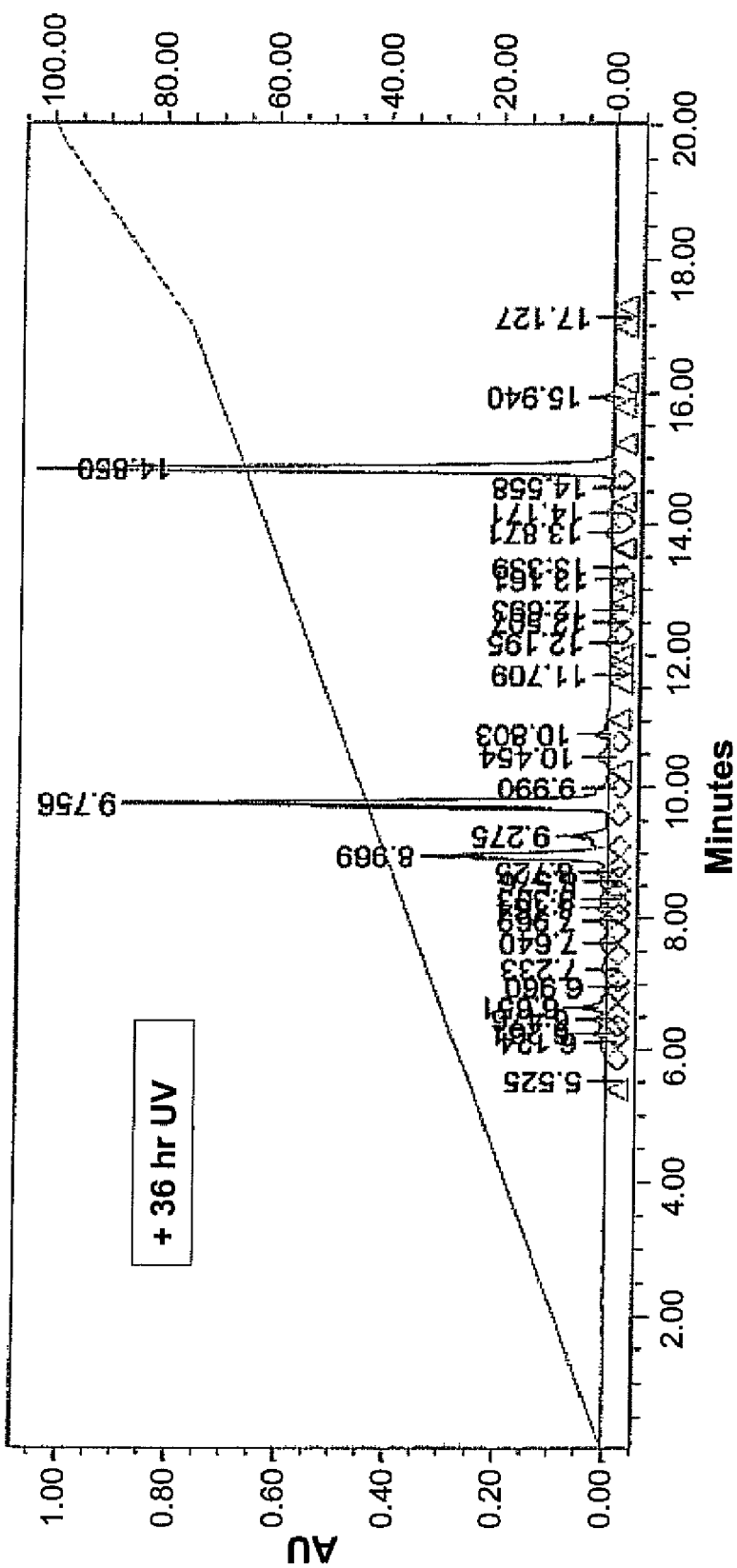
Figure 10, cont.

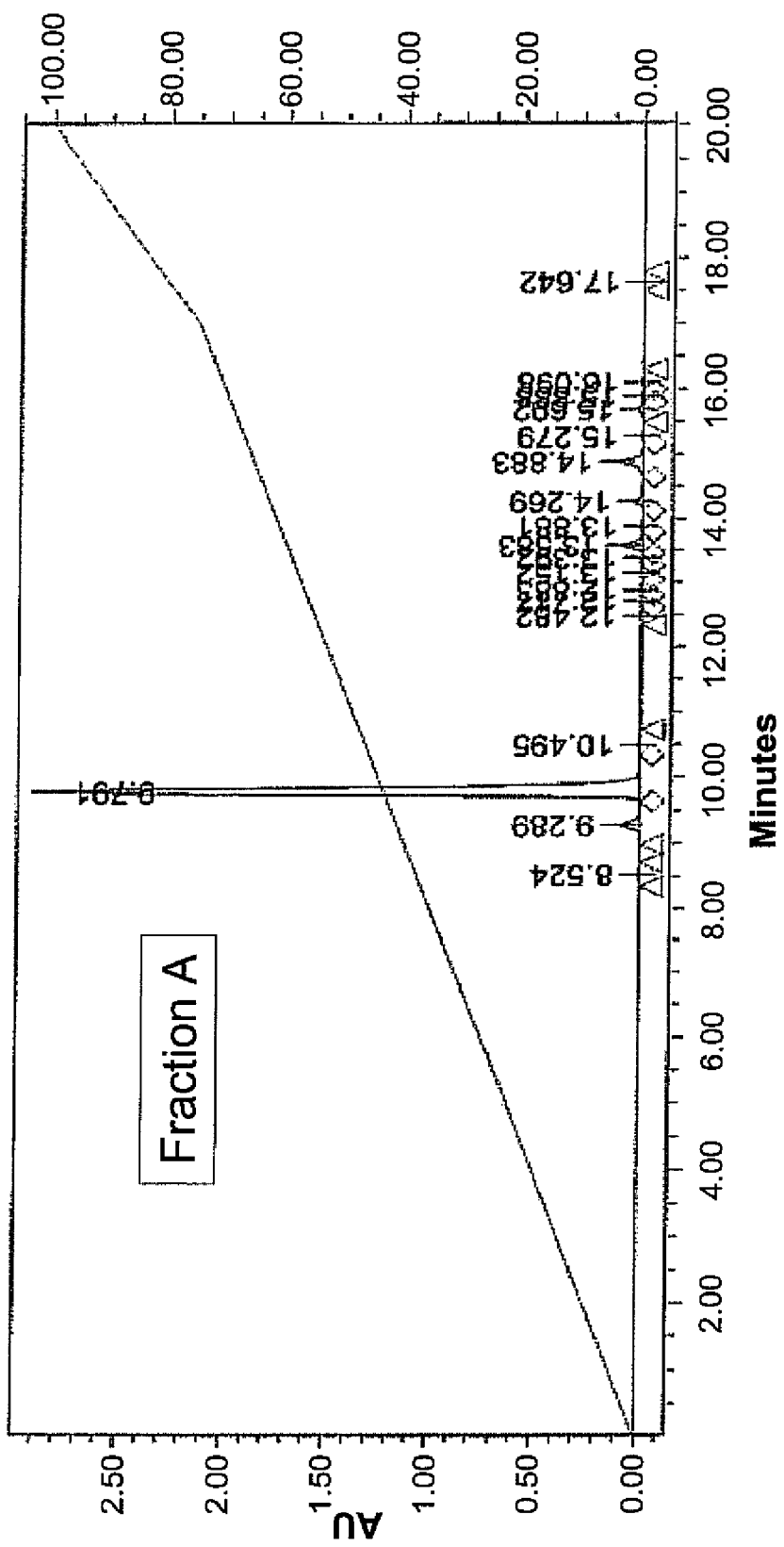
Figure 10, cont.

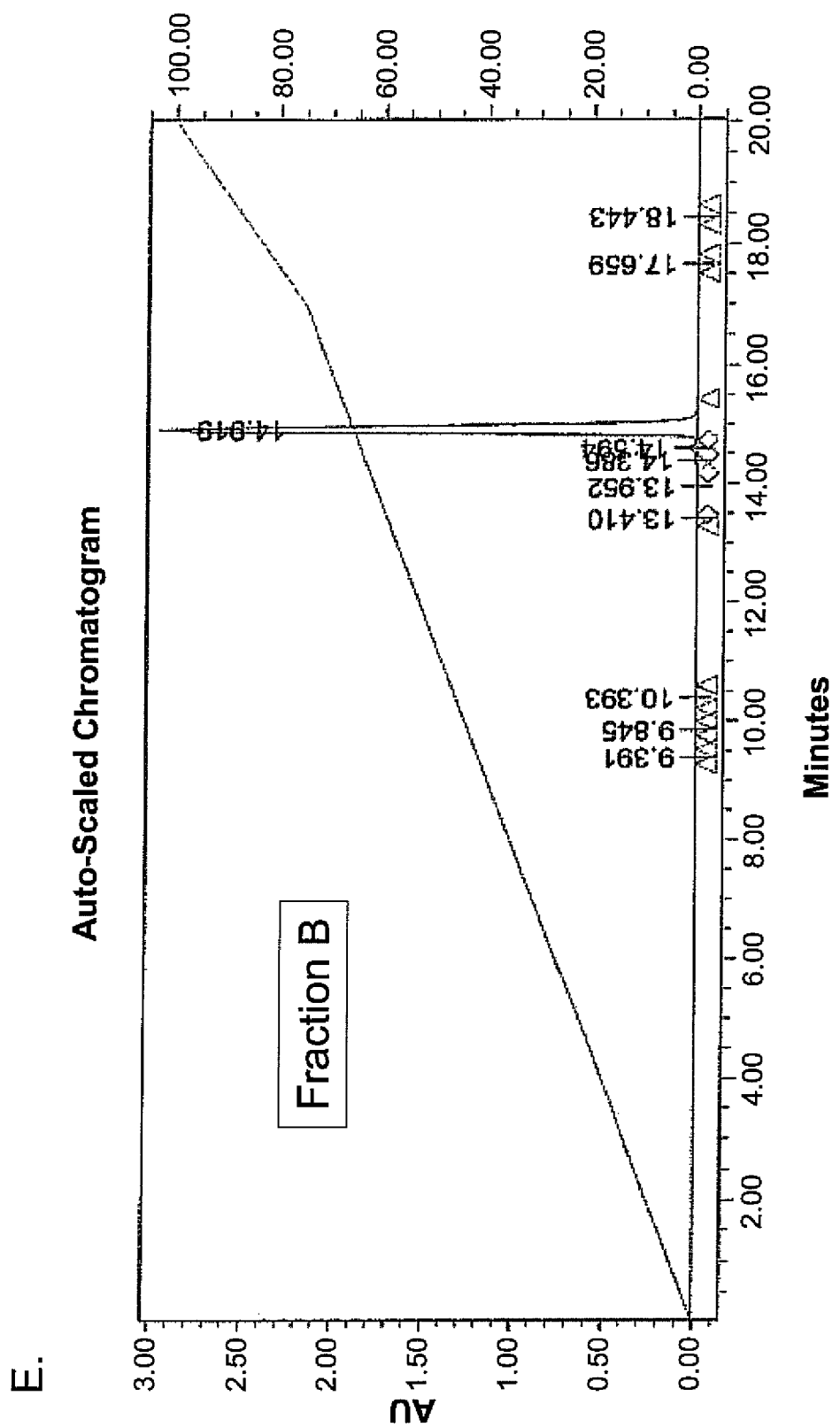
Figure 10, cont.

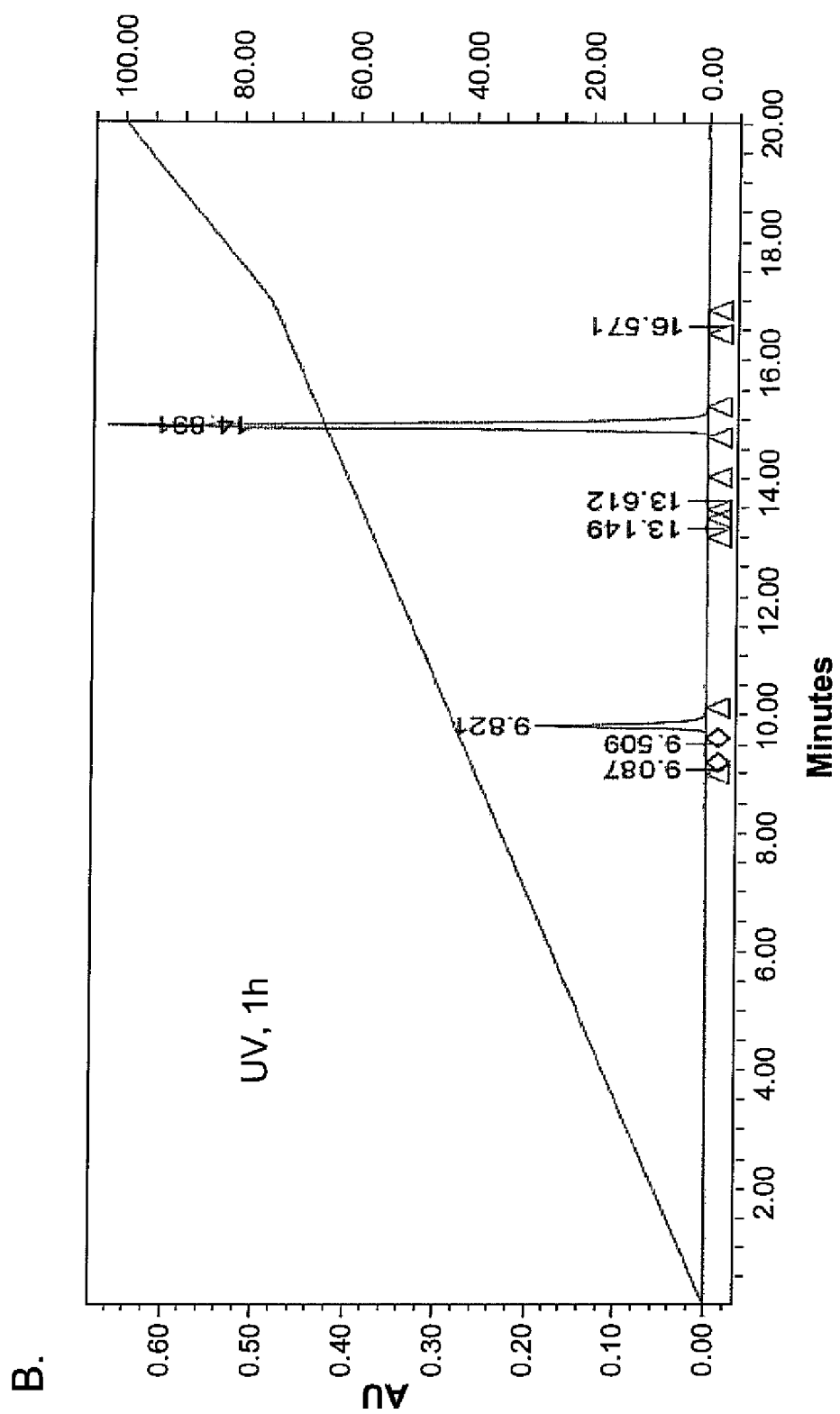
Figure 12, cont.

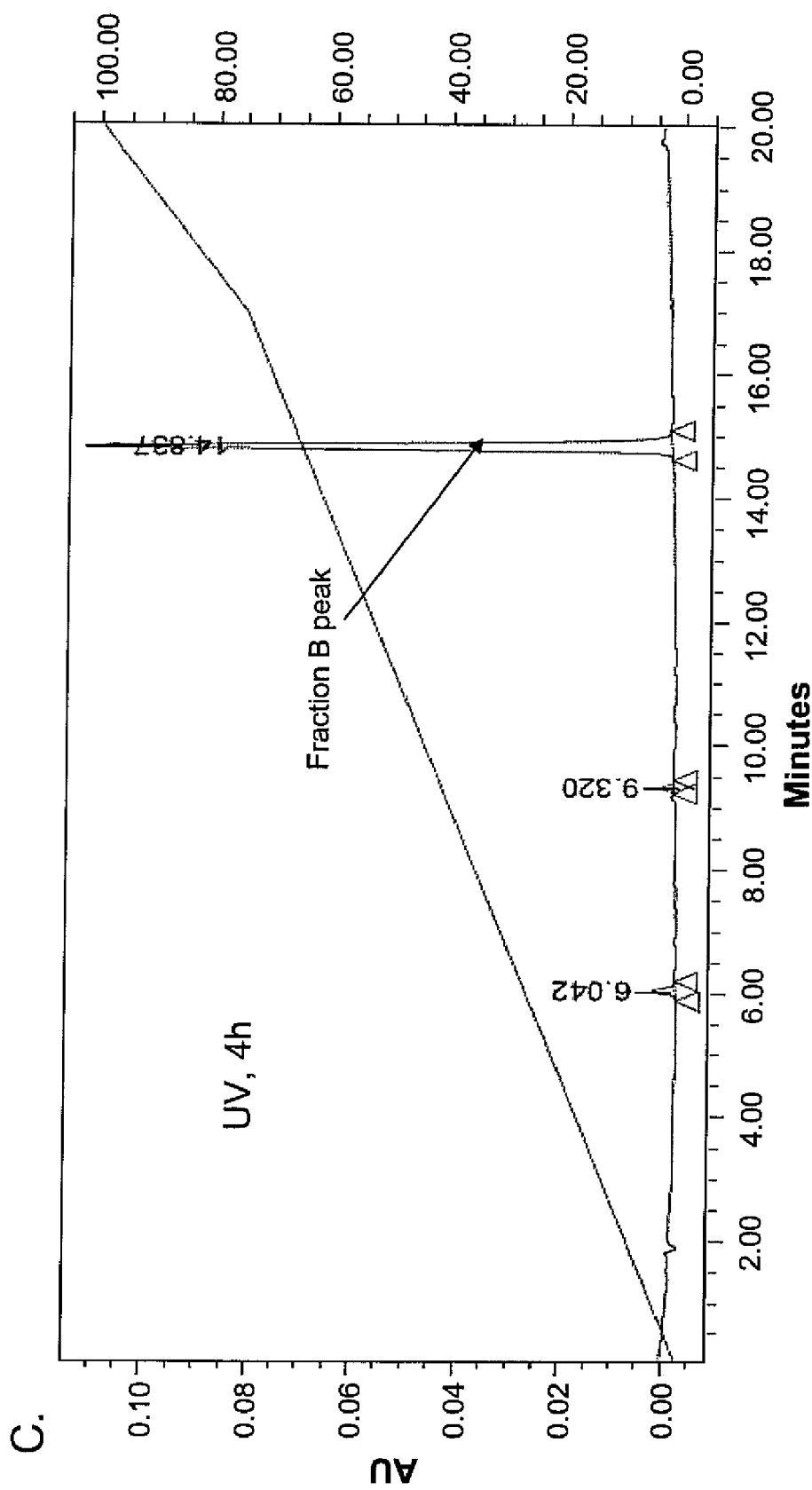
Figure 12, cont.

6-hydroxy-2,5,7,8-tetramethylchroman-2-carboxylic acid
Chemical Formula: $C_{14}H_{18}O_4$
Exact Mass: 250.12
Molecular Weight: 250.29 hv, $O_2$

TroloxQ (Fraction A)
Chemical Formula: $C_{14}H_{18}O_5$
Exact Mass: 266.12
Molecular Weight: 266.29 hv, $O_2$

G-Lox (Fraction B)
Chemical Formula: $C_{13}H_{16}O_3$
Exact Mass: 220.11
Molecular Weight: 220.26

A    B

C    D

E    F

A

B

C

D

E

A B

C D

A					B

C					D

A

B

C

D

A

B

C

D

E

F

A

B

C

D

E

PHOTO-INDUCED DAMAGE MITIGATING AGENTS AND PREPARATION AND METHODS OF USE THEREOF

CROSS-REFERENCE TO RELATED APPLICATIONS

This application claims the benefit of U.S. Provisional Application No. 61/116,048, filed Nov. 19, 2008, the disclosure of which is incorporated herein by reference in its entirety for all purposes.

STATEMENT REGARDING FEDERALLY SPONSORED RESEARCH

Not Applicable.

BACKGROUND OF THE INVENTION

The use of optically detectable labeling groups, and particularly those groups having high quantum yields, e.g., fluorescent or chemiluminescent groups, is ubiquitous throughout the fields of analytical chemistry, biochemistry, and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

Such analyses have generally been performed under conditions where the amounts of reactants are present far in excess of what is required for the reaction in question. The result of this excess is to provide ample detectability, as well as to compensate for any damage caused by the detection system and allow for signal detection with minimal impact on the reactants. For example, analyses based on fluorescent labeling groups generally require the use of an excitation radiation source directed at the reaction mixture to excite the fluorescent labeling group, which is then separately detectable. However, one drawback to the use of optically detectable labeling groups is that prolonged exposure of chemical and biochemical reactants to such light sources, alone, or when in the presence of other components, e.g., the fluorescent groups, can damage such reactants. The traditional solution to this drawback is to have the reactants present so far in excess that the number of undamaged reactant molecules far outnumbers the damaged reactant molecules, thus minimizing or negating the effects of the photo-induced damage.

A variety of analytical techniques currently being explored deviate from the traditional techniques. In particular, many reactions are based on increasingly smaller amounts of reagents, e.g., in microfluidic or nanofluidic reaction vessels or channels, or in "single molecule" analyses. Such low reactant volumes are increasingly important in many high throughput applications, such as microarrays.

The use of smaller reactant volumes offers challenges to the use of optical detection systems. When smaller reactant volumes are used, damage to reactants, such as from exposure to light sources for fluorescent detection, can become problematic and have a dramatic impact on the operation of a given analysis. This can be particularly detrimental, for example, in real time analysis of reactions that include fluorescent reagents that can expose multiple different reactions components to optical energy. In addition, smaller reactant volumes can lead to limitations in the amount of signal generated upon application of optical energy.

As such, methods and compositions that result in increased effective concentrations of reactants and detection molecules in smaller reactant volumes, thereby increasing signal in a smaller volume, would provide useful improvements to the methods and compositions currently available. For example, methods and compositions that prevent or mitigate to some extent photo-induced damage in a reaction of interest would be particularly useful.

BRIEF SUMMARY OF THE INVENTION

The present invention is generally directed to compounds, compositions, methods, devices and systems for preventing, reducing, or limiting the effects of photo-induced damage during illuminated reactions, particularly reactions that employ fluorescent or fluorogenic reactants. The term "photo-induced damage" refers generally to any direct or indirect impact of illumination on one or more reagents in a reaction resulting in a negative impact upon that reaction. The term "illuminated reactions" as used herein refers to reactions which are exposed to an optical energy source. Typically, such illumination is provided in order to observe the generation and/or consumption of reactants or products that possess a particular optical characteristic indicative of their presence, such as a shift in the absorbance spectrum and/or emission spectrum of the reaction mixture or its components.

In a first aspect, compositions of the invention can comprise a first reactant, a second reactant, and a photo-induced damage mitigating agent, wherein interaction of the first reactant with the second reactant under excitation illumination causes photo-induced damage to the first reactant in the absence of the photo-induced damage mitigating agent. In certain embodiments, the first reactant is confined, e.g., immobilized on a surface and/or in an optical confinement. In some embodiments, the first reactant is an enzyme, e.g., a polymerase. In some embodiments, the photo-induced damage mitigating agent is a triplet-state quencher and/or a free radical quencher, and in certain specific embodiments the photo-induced damage mitigating agent is a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, a photo-induced damage mitigating agent is a photo-induced damage mitigating agent admixture comprising multiple quinone derivatives. In certain embodiments, the second reactant is a fluorogenic or fluorescent molecule.

In another aspect of the invention, methods for performing an illuminated reaction are provided that comprise providing a substrate having a reaction mixture disposed thereon and illuminating the reaction mixture on the substrate with an excitation illumination. In some embodiments, the reaction mixture comprises first reactant, a second reactant, and a photo-induced damage mitigating agent, wherein the photo-induced damage mitigating agent reduces an amount of photo-induced damage to the first reactant that would otherwise result from interaction of the first reactant with the second reactant under excitation illumination in the absence of the photo-induced damage mitigating agent. In certain embodiments, the method further comprises monitoring a reaction between the first and second reactants during illumination. In some embodiments, the reaction is a base extension reaction and/or the first reactant is a polymerase enzyme. In certain embodiments, the second reactant is a fluorogenic or fluorescent molecule. In some embodiments, the photo-induced damage mitigating agent is a triplet-state quencher and/or a free radical quencher, and in certain specific embodiments the photo-induced damage mitigating agent is a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, a photo-induced damage mitigating agent is a photo-induced damage mitigating agent admixture comprising multiple quinone derivatives.

In yet another aspect, certain methods of the invention monitor a reaction mixture comprising at least one enzyme, a fluorescent or fluorogenic substrate for the enzyme, and a photo-induced damage mitigating agent, wherein interaction of the enzyme and the substrate under excitation illumination result in altered activity of the enzyme. Such methods can comprise directing an excitation radiation at a first observation region for a first period that is less than a photo-induced damage threshold period, which is lengthened by the presence of the photo-induced damage mitigating agent. In some embodiments, the photo-induced damage mitigating agent is a triplet-state quencher and/or a free radical quencher, and in certain specific embodiments the photo-induced damage mitigating agent is a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, a photo-induced damage mitigating agent is a photo-induced damage mitigating agent admixture comprising multiple quinone derivatives.

In further aspects, certain methods of the invention lengthen a photo-induced damage threshold period. Such methods can comprise including in a reaction mixture a photo-induced damage mitigating agent, such as a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, a photo-induced damage mitigating agent is a photo-induced damage mitigating agent admixture comprising multiple quinone derivatives.

In other aspects, compounds of the invention include or comprise one or more quinone derivatives, e.g., one or more benzoquinone derivatives, one or more hydroquinone derivatives, one or more epoxy quinone derivatives, one or more further quinone derivatives provided herein, or a combination thereof. In certain embodiments, compounds of the invention further include or comprise 6-hydroxy-2,5,7,8-tetramethylchroman-2-carboxylic acid or a derivative thereof. In some embodiments, a compound of the invention comprises a linking group, e.g., linking a photo-induced damage mitigating agent to at least one of a nucleotide polyphosphate, a polymerase, a surface, another component of an illumination reaction, or a combination thereof.

In certain aspects, devices of the invention can comprise a substrate having an observation region, a first reactant immobilized within the observation region, a second reactant disposed within the observation region, and at least one photo-induced damage mitigating agent disposed within the observation region, where interaction between the first and second reactants under excitation illumination causes photo-induced damage to the first reactant, and further wherein the photo-induced damage is reduced by the presence of the photo-induced damage mitigating agent. In some embodiments, the first reactant is an enzyme (e.g., a polymerase) and/or the observation region is within a zero mode waveguide. In some embodiments, the photo-induced damage mitigating agent is a triplet-state quencher and/or a free radical quencher, and in certain specific embodiments the photo-induced damage mitigating agent is a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, the photo-induced damage mitigating agent comprises multiple quinone derivatives, e.g., in an admixture.

In certain aspects, a system of the invention can serve to analyze an illuminated reaction that is susceptible to photo-induced damage when illuminated for a period longer than a photo-induced damage threshold period. Such a system can comprise a substrate having reagents for the reaction disposed thereon, including at least one photo-damage mitigating agent of the invention; a mounting stage supported by the substrate and configured to receive the substrate; an optical train positioned to be in optical communication with at least a portion of the substrate to illuminate the portion of the substrate and detect signals emanating therefrom; and a translation system operably coupled to the mounting stage or the optical train for moving one of the optical train and the substrate relative to the other. In some embodiments, the illuminated reaction is a sequencing reaction, e.g., a nucleotide sequencing-by-synthesis reaction. In certain embodiments, the substrate comprises at least one optical confinement, e.g., a zero mode waveguide.

In further aspects, a reaction mixture of the invention can comprise at least one fluorescent dye molecule and at least one photo-induced damage mitigating agent provided herein. Such a photo-induced damage mitigating agent can be a triplet-state quencher and/or a free radical quencher, and in certain specific embodiments, the agent is a quinone derivative, e.g., a benzoquinone derivative, a hydroquinone derivative, an epoxy quinone derivative, or other quinone derivative described herein, e.g., compounds of formulas I, II, III, IV, V, VI, VII, VIII, IX, and X. The photo-induced damage mitigating agent may further comprise 6-hydroxy-2,5,7,8-tetramethylchroman-2-carboxylic acid or a derivative thereof. In certain preferred embodiments, the photo-induced damage mitigating agent comprises multiple quinone derivatives. In some embodiments, one or more components of the reaction mixture are immobilized within an optical confinement, e.g., a zero mode waveguide. In certain embodiments, the reaction mixture comprises an enzyme, such as a polymerase enzyme. In specific embodiments, the reaction mixture is a sequencing-by-incorporation reaction mixture, e.g., comprises all components necessary for a sequencing-by-incorporation reaction. In further embodiments, at least one photo-induced damage mitigating agent is chemically linked to at least one other of the reaction components.

In yet further aspects, photo-induced damage mitigating agent admixtures are provided. In certain embodiments, such admixtures comprise at least about 2%, 5%, 10%, 15%, or 20% of a given component of the admixture, e.g. a quinone derivative provided herein. In certain embodiments, such admixtures comprise no more than about 50%, 40%, 30%, 20%, or 10% of a given component of the admixture, e.g. a quinone derivative provided herein. In certain preferred embodiments, such admixtures comprise at least about 2%, 5%, 10%, 15%, or 20% of a first component of the admixture, and no more than about 50%, 40%, 30%, 20%, or 10% of a second component of the admixture.

In another aspect, various methods for preparing photo-induced damage mitigating agent admixtures are provided. In certain embodiments, 6-hydroxy-2,5,7,8-tetramethylchroman-2-carboxylic acid is dissolved in methanol and the pH of the resulting solution is raised to at least about 11. The resulting basic solution is incubated for at least about 15 hours. The pH is typically readjusted after the incubation, e.g., to about 7-8. In certain preferred embodiments, the concentration of 6-hydroxy-2,5,7,8-tetramethylchroman-2-carboxylic acid in the incubated solution is about 100 mM. The incubation preferably is performed at room temperature (e.g., 18° C.-22° C.). In certain embodiments, the incubation is performed under ambient light, e.g., for about 15-20 hours. In more preferred embodiments, the incubation is performed in the absence of light (i.e., in the dark), e.g., for about 48-72 hours. The invention also provides methods for preparing reaction mixtures comprising adding a photo-induced damage mitigating agent admixture so prepared. Those of skill in the art will appreciate that that the compositions, systems, methods, and devices provided by the invention for mitigating photo-induced damage can be used alone or in combination.

The present invention also provides kits that incorporate photodamage-induced mitigating agents, or admixtures thereof, optionally with additional useful reagents. Such kits can include, e.g., a photodamage-induced mitigating agent of the invention packaged in a fashion to enable use of the agent with any of a variety of enzymes that participate in a reaction with one or more fluorescent or fluorogenic substrate. Depending upon the desired application, the kits of the invention optionally include, e.g., buffer solutions and/or salt solutions, divalent metal ions, i.e., $Mg^{++}$, $Mn^{++}$, $Ca^{++}$, and/or $Fe^{++}$, enzyme cofactors, substrates, standard solutions, e.g., dye standards for detector calibration, etc. Kits can optionally include reagents and instructions for preparing photo-induced damage mitigating agent admixtures. Such kits also typically include instructions for use of the compounds and other reagents in accordance with the desired application methods, e.g., nucleic acid sequencing and the like.

DETAILED DESCRIPTION OF THE INVENTION

Figure 1:
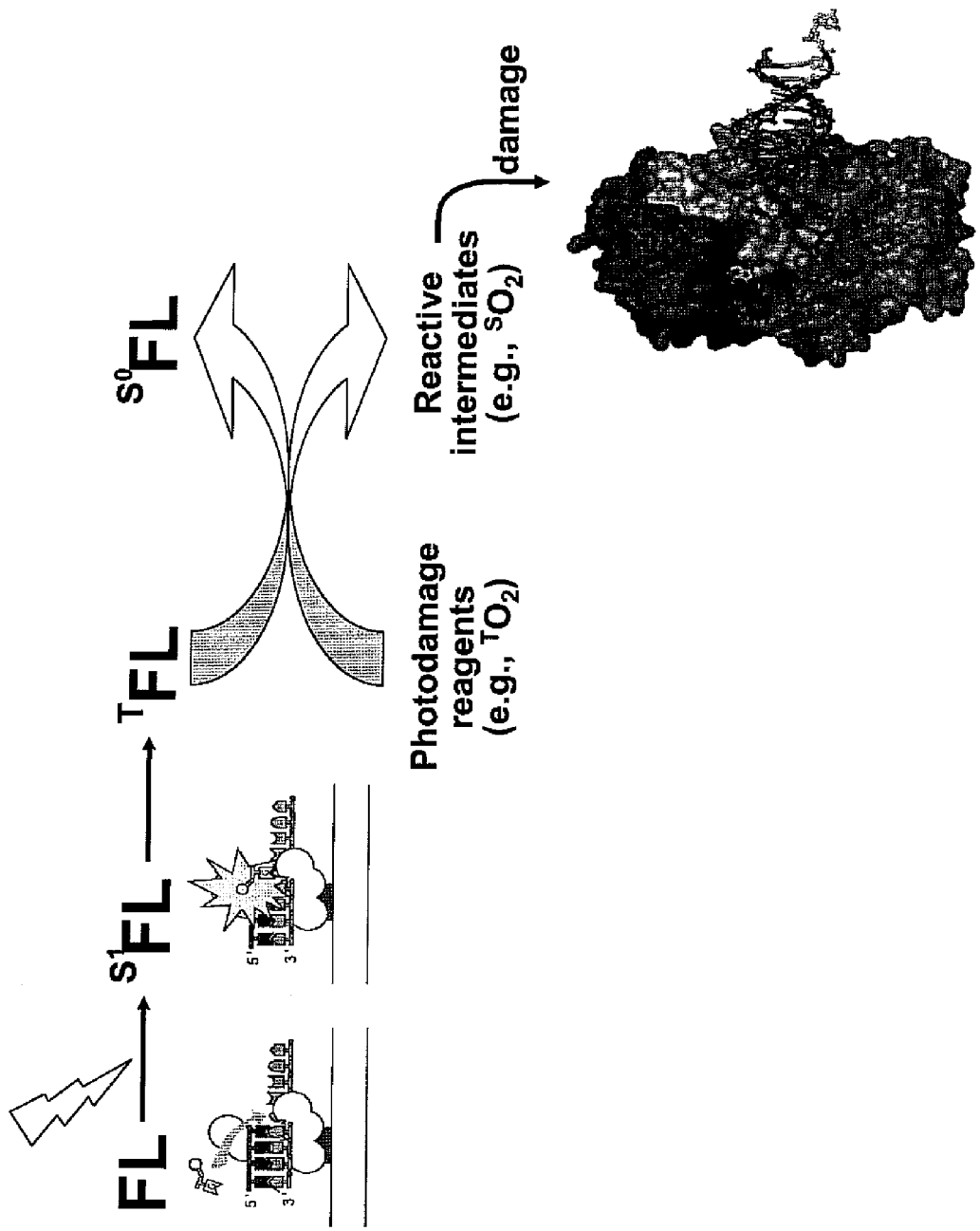
FIG. 1 is a schematic illustration of a proposed mechanism of photo-induced damage to DNA polymerase in template-dependent synthesis using fluorescent nucleotide analogs while under excitation illumination.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention. Further, unless otherwise clear from the context or expressly stated, any concentration, percentage, or ratio values or ranges provided herein are generally given in terms of admixture values or ranges without regard to any conversion of the particular component of a mixture that occurs upon or following subsequent treatment of the mixture, e.g., addition of the mixture to an analytical reaction. For example, a mixture comprising 10% of component A may be added to an analytical reaction, and subsequent to that addition component A may be partially or completely converted to one or more additional components in the analytical reaction, e.g., by reaction with other components of the analytical reaction and/or by conditions present (e.g., electromagnetic radiation, optical energy, pH, temperature, etc.) present in the analytical reaction. Likewise, a mixture comprising essentially equivalent amounts of two or more different components may see the ratio of the amounts of these components change after addition to an analytical reaction.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

I. General

The present invention is generally directed to compounds, compositions, methods, devices and systems for preventing, reducing, or limiting the effects of photo-induced damage during illuminated reactions, particularly reactions that employ fluorescent or fluorogenic reactants. The term "photo-induced damage" refers generally to any direct or indirect impact of illumination on one or more reagents in a reaction resulting in a negative impact upon that reaction. The term "illuminated reactions" as used herein refers to reactions which are exposed to an optical energy source. Typically, such illumination is provided in order to observe the generation and/or consumption of reactants or products that possess a particular optical characteristic indicative of their presence, such as a shift in the absorbance spectrum and/or emission spectrum of the reaction mixture or its components.

For example, the fluorescence detected in a fluorescence-based optical assay is the result of a three-stage process that occurs in the fluorophores or fluorescent dyes present in a reaction mixture. The first stage is excitation in which a photon with quantized energy from an external light source having a specific wavelength (e.g., from a laser) is supplied and absorbed by a fluorophore creating an excited electronic singlet state ($S_1'$). The second stage is the excited-state lifetime in which the excited fluorophore undergoes several different changes to relax its energy to the lowest singlet state ($S_1$). From the $S_1$ state several possible mechanisms can occur in the third stage, fluorescence, in which a photon of energy ($S_1$-$S_0$) is emitted returning the fluorophore to its ground state.

One of the many pathways that dissipate the energy of the excited electronic singlet state ($S_1$) is the intersystem crossing (ISC), which involves a change in spin multiplicity that transits the electron from $S_1$ to the excited triplet state ($T_1$). In many fluorescent dye molecules, the formation of the much longer lifetime triplet-state species greatly reduces the brightness of the fluorescence emission. In addition, it exhibits a high degree of chemical reactivity in this state that often results in photobleaching and the production of damaging free radicals and reactive intermediates, e.g., radical ions, carbenes, carbocations, carbanions, etc.

In general terms, the invention is directed to the performance of illuminated reaction analyses, where such analyses are illuminated for an amount of time that permits the effective performance of the analysis. In some embodiments, one or more photo-induced damage mitigating agents (e.g., triplet-state quenchers and/or free radical quenchers) may be provided in excess of the reactants in order to ensure that their protective effects extend to all reactant molecules in the reaction. However, in small volume reactions, providing such an excess of the photo-induced damage mitigating agent can potentially interfere with the ability of a reaction to proceed to completion. In certain aspects, compounds of the invention function as triplet-state quenchers and/or free radical quenchers. In further aspects, quenching slows the accumulation of damaging excited triplet-state forms of one or more reaction components. For example, in specific embodiments, quenching of a fluorescent dye in a reaction can slow the accumulation of the excited triplet state of the fluorophore, greatly improving the photophysical properties of the dye.

In certain preferred embodiments, the invention provides methods and compositions for nucleic acid analysis in which a photo-induced damage mitigating agent is linked to another reaction component or to a reaction site to bring the photo-induced damage mitigating agent into close spatial proximity to the reactants susceptible to damage by the illumination. For example, the photo-induced damage mitigating agent may be linked to one or more of a reactant (e.g., a nucleic acid or fluorescent dye), an enzyme (e.g., a polymerase or nuclease), or to a surface at which the reaction will take place (e.g., a well, chip, fiber, bead, etc.). In certain embodiments, the invention provides methods and compositions for nucleic acid analysis in which a nucleoside polyphosphate is linked to a fluorescent dye, and wherein the compound further includes, integrated into its structure (e.g., in the linker itself), a photo-induced damage mitigating agent, which generally refers to any agent that can prevent and/or mitigate damages caused by illumination, for example, by triplet/radical quenching. Such conjugates and compositions of the present invention are particularly useful in small reaction volumes, because incorporating the photo-induced damage mitigating agent into one of the reactants itself helps to maintain the protective effects of the agent without needing to provide the agent in an excess quantity.

The invention is generally applicable to any of a variety of optical assays that require substantial illumination and/or photoactivated conversion or excitation of chemical groups, e.g., fluorophores, and is particularly useful for assays that are impaired by the generation and/or accumulation of triplet-state forms or free radicals. For example, the compositions and methods provided herein may be used with fluorescence microscopy, optical traps and tweezers, spectrophotometry, fluorescence correlation spectroscopy, confocal microscopy, near-field optical methods, fluorescence resonance energy transfer (FRET), structured illumination microscopy, total internal reflection fluorescence microscopy (TIRF), etc.

Further, the methods provided herein are particularly useful in analyses that utilize very limited concentrations of reactants that might be subject to photo-induced damage, such as single molecule detection/monitoring assays. As will be appreciated, in such reagent limited analyses, any degradation of a critical reagent will dramatically impact the analysis by further limiting the reagent, which not only can adversely effect the detectable signal, but may also directly impact the reaction being monitored, e.g., by changing its rate, duration, or product(s). For example, photo-induced damage can include a photoinduced change in a given reagent that reduces the reactivity of that reagent in the reaction, e.g., photobleaching of a fluorescent molecule, which diminishes or removes its ability to act as a signaling molecule. Also included in the term photo-induced damage are other changes that reduce a reactant's usefulness in a reaction, e.g., by making the reagent less specific in its activity in the reaction. Likewise, photo-induced damage includes undesired changes in a reagent that are caused by interaction of that reagent with a product of another photoinduced reaction, e.g., the generation of singlet oxygen during a fluorescence excitation event, which singlet oxygen may damage organic or other reagents, e.g., proteins. For example, damage to an enzyme that catalyzed a reaction being monitored may cause a reduction in the rate of the reaction, in some cases stopping it altogether, or may reduce the duration or fidelity of the reaction.

One particularly apt example of analyses that benefit from the invention are single-molecule biological analyses, including, inter alia, single molecule nucleic acid sequencing analyses, single molecule enzyme analyses, hybridization assays (e.g., antibody assays), nucleic acid hybridization assays, and the like, where the reagents of primary import are subjected to prolonged illumination with relatively concentrated light sources (e.g., lasers and other concentrated light sources, such as mercury, xenon, halogen, or other lamps) in an environment where photoconversion/excitation is occurring with its associated generation of products. In certain embodiments, the methods, compositions, and systems are used in nucleic acid sequencing processes that rely on detection of fluorescent or fluorogenic reagents. Examples of such sequencing technologies include, for example, SMRT™ nucleic acid sequencing (described in, e.g., U.S. Pat. Nos. 6,399,335, 6,056,661, 7,052,847, 7,033,764, 7,056,676, 7,361,466, 7,416,844, and in Eid, et al. (2009) Science 323: 133-138, the full disclosures of which are incorporated herein by reference in their entireties for all purposes), non-real time, or "one base at a time" sequencing methods available from, e.g., Illumina, Inc. (San Diego, Calif.), Helicos Biosciences (Cambridge, Mass.), Clonal Single Molecule Array™, and SOLiD™ sequencing. Such prolonged illumination can result in photo-induced damage to these reagents and diminish their effectiveness in the desired reaction.

II. Illuminated Analyses

Certain aspects of the invention are generally directed to mitigating photo-induced damage during the performance of illuminated analyses. The terms "illuminated analysis" and "illuminated reaction" are used interchangeably and generally refer to an analytical reaction that is occurring while being illuminated (e.g., with excitation radiation), so as to evaluate the production, consumption and/or conversion of luminescent (e.g., fluorescent) reactants and/or products. As used herein, the terms "reactant" and "reagent" are used interchangeably. In certain preferred embodiments, the illuminated reaction is a sequencing reaction and the photo-induced damage results, directly or indirectly, from an excitation radiation source used to detect nucleotides as they are added to a nascent nucleic acid strand.

The amount of time an illuminated analysis may be carried out before photo-induced damage so substantially impacts the reactants to render the analysis non-useful is referred to as the "photo-induced damage threshold period." A photo-induced damage threshold period is assay-dependent, and is affected by various factors, including but not limited to characteristics of enzymes in the assay (e.g., susceptibility to photo-induced damage and the effect of such damage on enzyme activity/processivity), characteristics of the radiation source (e.g., wavelength, intensity), characteristics of the signal-generating molecule (e.g., type of emission, susceptibility to photo-induced damage, propensity to enter triplet state, and the effect of such damage on the brightness/duration of the signal), similar characteristics of other components of the assay. It can also depend on various components of the assay system, e.g., signal transmission and detection, data collection and analysis procedures, etc. It is well within the abilities of the ordinary practitioner to determine an acceptable photo-induced damage threshold period for a given assay, e.g., by monitoring the signal decay for the assay in the presence of a photodamaging agent and identifying a period for which the signal is a reliable measure for the assay. In terms of the invention, the photo-induced damage threshold period is that period of illuminated analysis during which such photo-induced damage occurs so as to reduce the rate of the subject reaction by at least 10%, 20%, 30%, 40%, 50%, 60%, 70%, 80%, or 90% over the same reaction in the absence of such illumination. It is an object of the invention to increase the photo-induced damage threshold period, thereby increasing the amount of time reactions can proceed toward completion with minimal damage to the reactants, thereby lengthening the time in which the detectable signal is an accurate measure of reaction progression.

In some contexts, a "photo-induced damaged" reaction may be subject to spurious activity, and thus be more active than desired. In such cases, it will be appreciated that the photo-induced damage threshold period of interest would be characterized by that period of illuminated analysis during which such spurious activity, e.g., as measured by an increase in reaction rate, or an increase in non-specific reaction rate, is no more than 10% over a non-illuminated reaction, no more than 20% over a non-illuminated reaction, no more than 50% over a non-illuminated reaction, and in some cases, no more than 90% over a non-illuminated reaction. In one non-limiting example, where a nucleic acid polymerase, by virtue of a photodamaging event, begins to incorrectly incorporate nucleotides during template directed synthesis, such activity would impact the photo-induced damage threshold period as set forth above. In this case, the compounds and methods of the invention would increase the photo-induced damage threshold period, thus increasing the amount of time the reaction could be illuminated before the above-described spurious activity occurred.

With reference to nucleic acid analyses, it has been observed that in template-directed synthesis of nucleic acids using fluorescent nucleotide analogs as a substrate, prolonged illumination can result in a substantial degradation in the ability of the polymerase to synthesize the nascent strand of DNA, as described previously, e.g., in U.S. Published Patent Application No. 20070161017, incorporated by reference herein in its entirety for all purposes. Damage to polymerase enzymes, template sequences, and/or primer sequences can significantly hinder the ability of the polymerase to process longer strands of nucleic acids. For example, reduction in the processivity of a polymerase leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. Such a reduction in the activity of an enzyme can have significant effects on many different kinds of reactions in addition to sequencing reactions, such as ligations, cleavages, digestions, phosphorylations, etc.

Without being bound to a particular theory or mechanism of operation, it is believed that at least one cause of photo-induced damage to enzyme activity, particularly in the presence of fluorescent reagents, results from the direct interaction of the enzyme with photo-induced damaged fluorescent reagents. Further, it is believed that this photo-induced damage of the fluorescent reagents (and possibly additional damage to the enzyme) is at least partially mediated by reactive intermediates (e.g., reactive oxygen species) that are generated during the relaxation of triplet-state fluorophores. One or both of the photo-induced damaged fluorescent reagents and/or reactive intermediates may be included in the overall detrimental effects of photo-induced damage. One possible mechanism for this photo-induced damage is shown in FIG. 1. As shown, a fluorophore excited by exposure to electromagnetic radiation at an excitation wavelength can transition into a triplet state. This may occur directly, or as a result of multi-photon processes, where an excited fluorophore transitions to the triplet state upon contact with a photon of a wavelength that is shorter (or bluer) than the nominal excitation wavelength of the fluorophore. Subsequent relaxation of the triplet-state fluorophore can lead to generation of reactive intermediates, which can, in turn, damage one or both of the fluorophore or the enzyme processing the fluorophore, e.g., the polymerase. Accordingly, photo-induced damage mitigating agents (e.g., free radical and/or triplet-state quenching agents) are needed to prevent or slow the formation of reactive intermediates. Such agents can be included within the reaction mixtures or directly incorporated into compounds of the invention to alleviate and/or prevent the effects of reactive intermediates, as well as other species generated during illuminated reaction that can cause photo-induced damage.

As will be appreciated, the photo-induced damage sought to be prevented by the methods and compositions of the invention is not merely photo-induced damage to fluorescent reagents, e.g., photobleaching, but is also directed to prevention or reduction of the downstream effects of photoactivation of such fluorescent reagents to other reagents that are of limited quantity in a reaction mixture, and as such, their limited presence is more greatly impacted by even slight losses due to photo-induced damage, and particularly reactive proteins or enzymes, which, without being bound to a theory of operation, may include damage to the enzymes or reactive proteins or irreversible interactions between such enzymes or proteins and the photo-induced damaged reagents. As suggested by the foregoing, photo-induced damage generally refers to an alteration in a given reagent, reactant, or the like, that causes such reagent to have altered functionality in a desired reaction, e.g., reduced activity, reduced specificity, or a reduced ability to be acted upon, converted, or modified, by another molecule, that results from, either directly or indirectly, a photo-induced reaction, e.g., a photo-induced reaction creates a reactant that interacts with and causes damage to one or more other reactants. Typically, such photoreaction directly impacts either the reactant of interest, e.g., direct photo-induced damage, or impacts a reactant within one, two or three reactive steps of such reactant of interest. Further, such photoreaction can directly impact the reaction of interest, e.g., causing a change in rate, duration, or fidelity of the reaction.

As generally referred to herein, such limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized, or otherwise confined within a given area (e.g., a zero mode waveguide), so as to provide limited quantity of reagents in that given area, and in certain cases, provide small numbers of molecules of such reagents within that given area, e.g., from 1 to 1000 individual molecules, preferably between 1 and 10 molecules. As will be appreciated, photo-induced damage of immobilized reactants in a given area will have a substantial impact on the reactivity of that area, as other, non-damaged reactants are not free to diffuse into and mask the effects of such damage.

III. Prevention Or Mitigation Of Photo-Induced Damage

In a first aspect, the invention is directed to methods and compositions that reduce the amount of photo-induced damage to one or more reactants during an illuminated reaction, e.g., during excitation, the excited-state lifetime, or emission. In particular, compositions are provided that yield a reduction in the level of photo-induced damage (or an increase in the photo-induced damage threshold period) as compared to such reactions in the absence of such compositions. As used herein, the components of such compositions that provide such effects are generally referred to as photo-induced damage mitigating agents. In particular, photo-induced damage Mitigating agents are provided in the context of the illuminated reaction to reduce the level of photo-induced damage (and/or increase the photo-induced damage threshold period), that would otherwise have occurred but for the presence of the photo-induced damage mitigating agent.

Again, the definition of an agent as a photo-induced damage mitigating agent is generally reflective of the impact that such agent has on the actual photo-induced damage event or the downstream impacts of that damage. As such, the detrimental impact of the photo-induced damage event, whether resulting from actual damage to a given reagent or from interaction with a damaged reagent, is generally referred to herein as photo-induced damage. Therefore, a photo-induced damage mitigating agent may prevent photo-induced damage of one or more reagents, or it may mitigate the impact that a photo-induced damaged reagent may have on a particular, limited reagent in the reaction of interest. By way of example, an agent that blocks a detrimental interaction between a photo-induced damaged fluorescent compound and a critical enzyme component (e.g., by quenching the triplet state of the fluorescent compound) would still be referred to as a photo-induced damage mitigating agent, regardless of the fact that it did not prevent the initial photo-induced damage to the fluorescent reagent.

Measurements of reduction of photo-induced damage as a result of inclusion or treatment with one or more photo-induced damage mitigating agents may be characterized as providing a reduction in the level of photo-induced damage over an untreated reaction. Further, characterization of a reduction in photo-induced damage generally utilizes a comparison of reaction rates, durations, or fidelities, e.g., of enzyme activity, and/or a comparison of the photo-induced damage threshold period, between a treated reaction mixture and an untreated reaction mixture.

In the case of the present invention, the inclusion of photo-induced damage mitigating agent(s) of the invention generally results in a reduction of photo-induced damage of one or more reactants in a given reaction, as measured in terms of "prevented loss of reactivity" in the system. Using methods known in the art, the amount of prevented loss of activity can at least 10%, preferably greater than 20%, 30%, or 40%, and more preferably at least 50% reduction in loss of reactivity, and in many cases greater than a 90% and up to and greater than 99% reduction in loss of reactivity. By way of illustration, and purely for the purpose of example, when referring to reduction in photo-induced damage as a measure of enzyme activity in the presence and absence of the photo-induced damage mitigating agent, if a reaction included a reaction mixture having 100 units of enzyme activity that would, in the absence of a photo-induced damage mitigating agent and following illuminated analysis, yield a reaction mixture having only 50 units of activity, then a 10% reduction in photo-induced damage would yield a final reaction mixture of 55 units (e.g., 10% of the 50 units otherwise lost, would no longer be lost).

IV. Photo-Induced Damage Mitigating Agents

Accordingly, in at least one aspect, the present invention is directed to the inclusion within the illuminated reaction volume of one or more photo-induced damage mitigating agents that function to block or otherwise minimize the pathways that lead to such photo-induced damage. Such agents include reducing and/or oxidizing agents or anti-fade agents that reduce the formation/lifetime of the triplet-state fluorophores (also referred to as triplet-state quenchers), in some cases by interacting/reacting with a triplet-state fluorophore, thereby preventing its interaction with (and resulting photo-induced damage to) other reaction components. Such agents also include oxygen and/or radical scavenging/quenching agents that remove oxygen, reactive oxygen species, and other radicals from the reaction mixture, thus preventing downstream damage to enzymes within the system. Such agents also include mixtures of agents having one or more reducing, oxidizion, anti-fade, triplet-state quenching, oxygen radical scavenging/quenching, or radical scavenging/quenching activities. Certain examples of photo-induced damage mitigating agents are provided, e.g., in U.S. Published Patent Application No. 20070161017, previously incorporated herein by reference in its entirety for all purposes.

In certain embodiments, a photo-induced damage mitigating agent may be physically linked to one or more reaction components (e.g., a dye molecule, enzyme, nucleotide, etc.), or to a reaction site (e.g., on a substrate, in a well, in a zero mode waveguide, on a bead or optical fiber, etc.). In certain embodiments, a photo-induced damage mitigating agent may be linked to multiple reaction components or to one or more reaction components and to a reaction site. In some such embodiments, a tridendate structure may be formed connecting the photo-induced damage mitigating agent to two different reaction components, such as when the photo-induced damage mitigating agent is incorporated into a linker connecting two other components of the reaction. Methods of producing such compounds are provided, e.g., in U.S. Ser. No. 61/026,992 (filed Feb. 7, 2008) and Ser. No. 12/367,411, (filed Feb. 6, 2009), both of which are incorporated herein by reference in their entireties for all purposes. In a single molecule sequencing reaction, such a tridendate structure may include a photo-induced damage mitigating agent, a dye, and a nucleotide, for example. Such an embodiment may be beneficial to bring the photo-induced damage mitigating agent near the dye to facilitate rapid quenching of any triplet state occurring in the dye molecule. In certain embodiments, a photo-induced damage mitigating agent is a quinone derivative, as described below.

In at least one aspect, the present invention provides compounds of the formula:

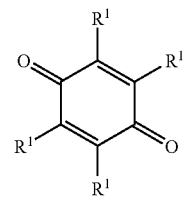

I and the formula

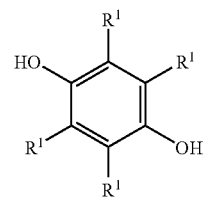

II wherein each $R^1$ group is independently selected from the group consisting of hydrogen, halogen, alkyl, —$CH_3$, —$(CH_2)_nR^2$, —$(CH_2)_nR^2R^3$, —$SO_3H$, —$NO_2$, —$OR^2$, —$COR^2$, —$COOR^2$, —$(CH_2)_nOR^2$, —$CH(OH)R^2$, —$S(O)_mR^2$, —$SO_3R^2$, —$CONH_m(R^2)_{2-m}$, —$SO_2NH_m(R^2)^{2-m}$, $NH_m(R^2)_{2-m}$, —$CONHSO_3H$, —$(CH_2)_nR^5$, —$CH(OR^2)R^3$, —$(CH_2)_nR^2R^5$, —$R^5$, —$OR^5$, —$COR^5$, —$COOR^5$, —$(CH_2)_nOR^5$, where m is an integer and where n is an integer from 1 to 4;

$R^2$ is selected from the group consisting of hydrogen, halogen, alkyl, —$CH_3$, hydroxyl, —$SO_3H$, —$NO_2$, —$OR^3$, —$COR^3$; —$COOR^3$, —$CH(OR^3)R^4$, —$C(OH)R^3$, —$SO_3R^3$, —$OR^3R^5$, —$COR^5$, —$COR^3R^5$, —$COR^3R^4R^5$, —$CH(OH)R^5$, —$S(O)_mR^3$, —$SO_3R^3$, —$CONH_m(R^3)_{2-m}$, $NH_m(R^3)_{2-m}$, —$CONHSO_3H$, —$SO_2NH_m(R^3)^{2-m}$, where in is an integer;

$R^3$ and $R^4$ are independently selected from the group consisting of hydrogen, halogen, hydroxyl, alkyl, —$CH_3$, —$SO_3H$, $NO_2$, and —COOH; and $R^5$ is a "linker" to physically link the compounds of the invention to other reactants or reaction sites so as to improve the ability of such compounds to mitigate photo-induced damage to materials normally susceptible to such damage. In certain preferred embodiments, a combination of at least one compound of formula I and at least one compound of formula II is a photo-induced damage mitigating agent. In certain preferred embodiments, a combination of 6-hydroxy-2,5,7,8-tetramethylchroman-2-carboxylic acid (also a quinone derivative, and specifically a hydroquinone derivative) and at least one compound of formula I and/or at least one compound of formula II is a photo-induced damage mitigating agent.

In a further aspect, the invention provides quinone derivatives of the formulas:

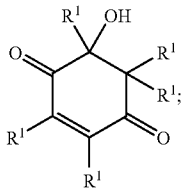

the formula III

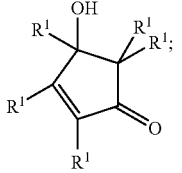

the formula IV

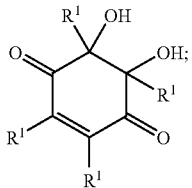

the formula V

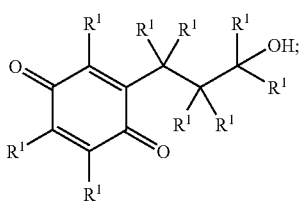

the formula VI

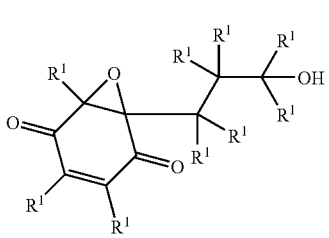

the formula VII

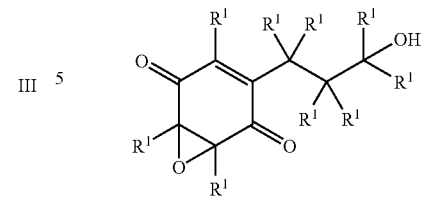

the formula VIII

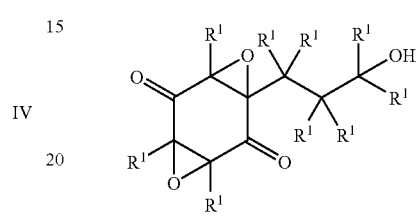

and the formula IX

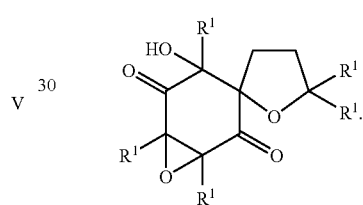

X wherein each $R^1$ group is independently selected from the groups provided above for $R^1$ of formulas I and II. In certain embodiments, compounds of formula III are produced by base treatment of a compound of formula IV. A scheme for the transformation of compounds of formula IV into compounds of formula III is described elsewhere herein and a reaction scheme is provided in FIG. 6.

There are various mechanisms for derivation of certain quinone derivatives of the invention. For example, such derivation can comprise a) hydrolytic opening of a ring by addition of $H_2O$ under acidic, basic, or neutral conditions, b) oxidation of a hydroquinone to quinone by loss of c) further oxidation, e.g., epoxidation, by addition of O, and d) photolytic insertion of singlet oxygen. The order of these three steps may vary. Equivalently, oxidation of hydroquinone to quinone may occur through addition of $O_2$ and release of $H_2O_2$, and/or the further oxidation step may occur through addition of $H_2O_2$ and release of $H_2O$. In certain preferred embodiments, a combination of at least two compounds of formulas III, IV, V, VI, VII, VIII, IX, and X is a photo-induced damage mitigating agent. In certain preferred embodiments, a combination of at feast two compounds of formulas III is a photo-induced damage mitigating agent. In certain preferred embodiments, a combination of 6-hydroxy-2,5,7,8-tetramethylchroman-2-carboxylic acid and at least one compound of formulas III, IV, V, VI, VII, VIII, IX, and X is a photo-induced damage mitigating agent. In certain preferred embodiments, a combination of at least one compound of formula I and/or formula II and at least one compound of formula III IV, V. VI VII VIII, IX, and X is a photo-induced damage mitigating agent.

The term "linker" encompasses any moiety that is useful to connect one or more compounds of the invention (e.g., a triplet-state or free radical quencher described herein) to a component of an illuminated reaction (e.g., a reporter molecule). Methods for choosing, synthesizing, and attaching linkers to reactants are well known to those of ordinary skill in the art and further discussion and exemplary linker moieties are provided, e.g., in U.S. Ser. No. 61/026,992 (filed Feb. 7, 2008) and Ser. No. 12/367,411, (filed Feb. 6, 2009). Linkers may also be branched to connect three or more components of a reaction mixture, e.g., in to a tridentate, tetradentate, or higher order structure. For example, a dye may be linked to one or more photo-induced damage mitigating agents, enzymes, or other reaction components. In certain preferred embodiments, a luminescently labeled reaction component (e.g., fluorescent nucleotide) is linked to at least one photo-induced damage mitigating agent provided herein.

In certain embodiments, the linker is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker moiety is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl). In certain embodiments, molecules that have trifunctional linkage capability are used, including, but are not limited to, cynuric chloride, mealamine, diaminopropanoic acid, aspartic acid, cysteine, glutamic acid, pyroglutamic acid, S-acetylmercaptosuccinic anhydride, carbobenzoxylysine, histine, lysine, serine, homoserine tyrosine, piperidinyl-1,1-amino carboxylic acid, diaminobenzoic acid, etc.

The linker as a whole may comprise a single covalent bond or a series of stable bonds. Thus, a reporter molecule (e.g., a fluorescent dye) may be directly attached to a triplet-state or free radical quencher of the invention (e.g., a quinone derivative). A linker that is a series of stable covalent bonds can incorporate non-carbon atoms, such as nitrogen, oxygen, sulfur and phosphorous, as well as other atoms and combinations of atoms, as is known in the art. If the linker is not directly attached to a reactant by a single covalent bond, the attachment may comprise a combination of stable chemical bonds, including for example, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In an exemplary embodiment, the dye is conjugated to the nucleoside triphosphate as an alkylated tetraphosphate analog.

In certain preferred embodiments, linkers are derived from molecules which comprise at least two reactive functional groups (e.g., one on each terminus), and these reactive functional groups can react with complementary reactive functional groups on the various reaction components or used to immobilize one or more reaction components at the reaction site. "Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfenic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

The compound of formula I may also be generically referred to as "2,3,5,6-Tetra[$R^1$]-1,4-Benzoquinone," and the compound of formula II may also be generically referred to as "2,3,5,6-Tetra[$R^1$]-1,4-Hydroquinone." In general, one or more of the R groups may be chosen to bring additional properties to the compound, e.g., solubility, increased quenching abilities, or ability to physically link the compound to other reaction components (e.g., a dye molecule, enzyme, nucleotide, etc.) or to a reaction site (e.g., on a substrate, in a well, in a zero mode waveguide, on a bead or optical fiber, etc.), as described above. In certain preferred embodiments, the $R^1$ group comprises a $C_1$ to $C_6$ alkyl group, which may be branched or unbranched, and is substituted in certain preferred embodiments.

Figure 2:
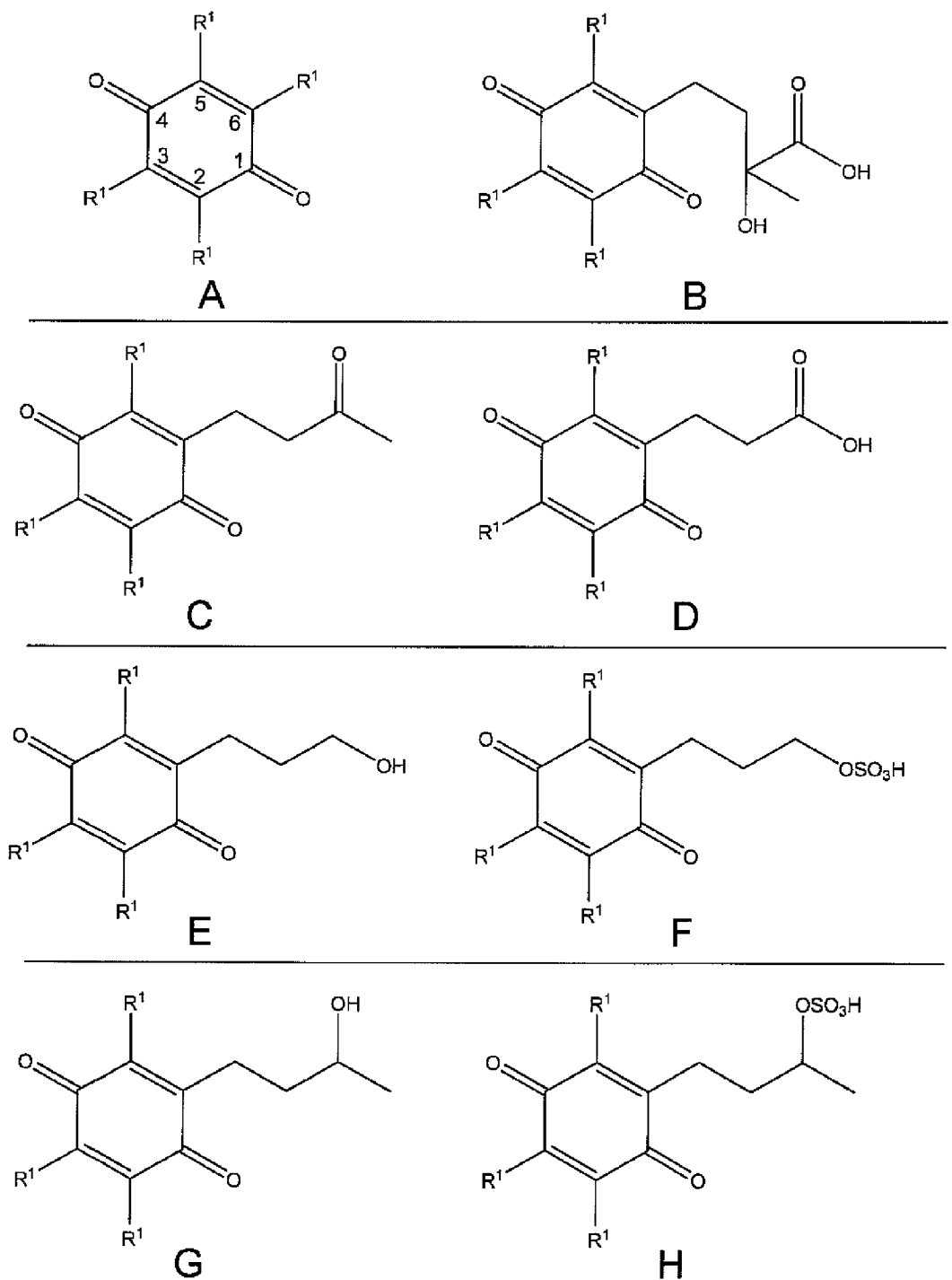
FIG. 2 provides certain exemplary embodiments of the photo-induced damage mitigating agents provided herein.

Certain exemplary embodiments of photo-induced damage mitigating agents of formula I are shown in FIG. 2. For ease of reference, the general structure of formula I is also shown (A). In certain preferred embodiments, $R^1$ at C6 is $(CH_2)_2R^2$ and $R^2$ is selected from the group consisting of —$COCH_3$ (formula C), —COOH (formula D), and —$C(OH)CH_3$ (formula G). In other preferred embodiments, $R^1$ is $(CH_2)_3R^2$ and $R^2$ is —OH (formula E). In still further preferred embodiments, $R^1$ is selected from the group consisting of —$(CH_2)_3OSO_3H$ (formula F), —$(CH_2)_2CH(OSO_3H)CH_3$ (formula H), and —$(CH_2)_2COH$—$CH_3COOH$ (formula B). Formulas B-H are shown with only one substituted alkyl group, but as indicated by the $R^1$ groups at positions 2, 3, and 5, formulas having more than one substituted alkyl chain are contemplated and represent additional embodiments of the invention.

Figure 3:
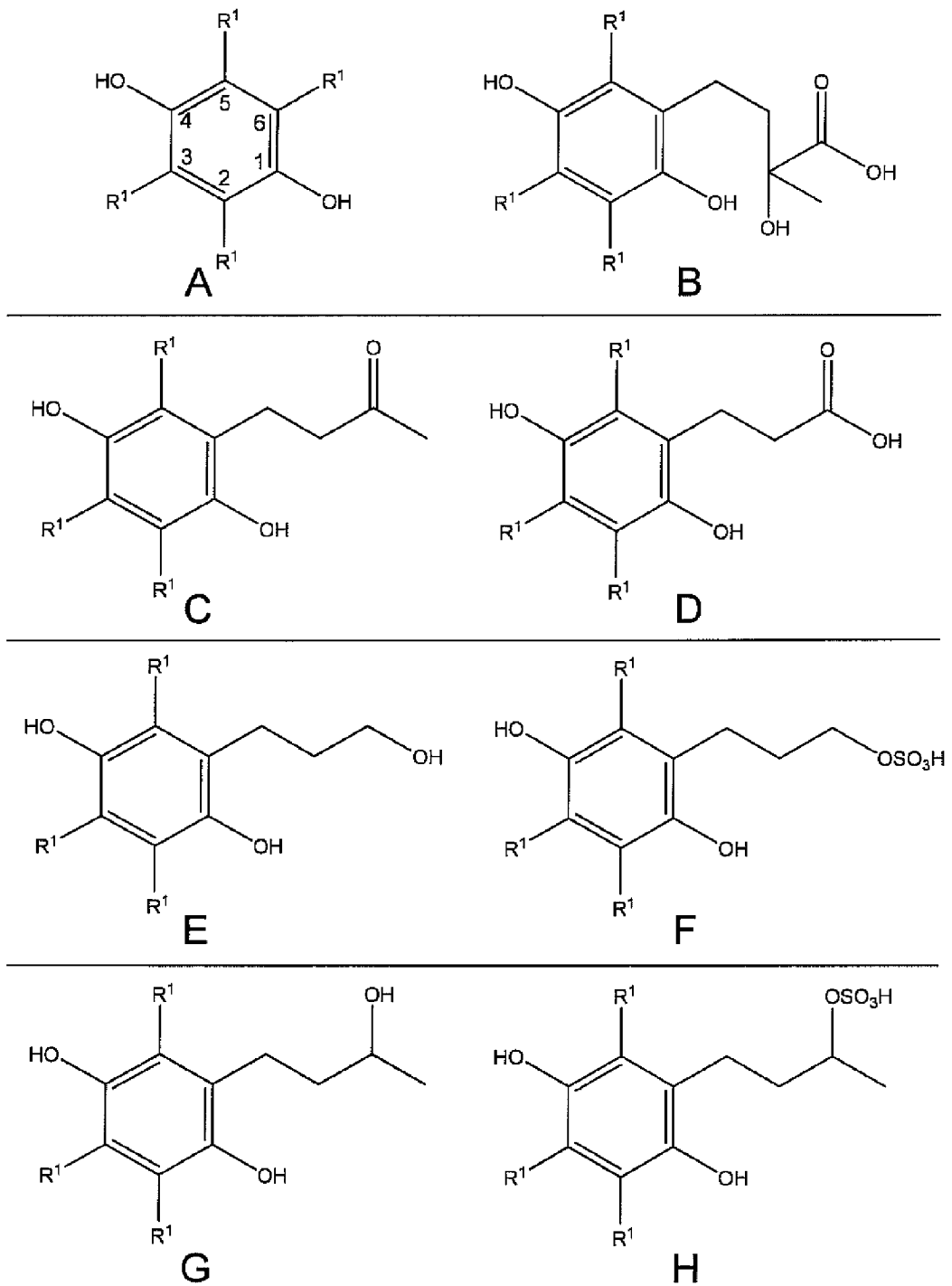
FIG. 3 provides certain exemplary embodiments of the photo-induced damage mitigating agents provided herein.

Certain exemplary embodiments of photo-induced damage mitigating agents of formula II are provided in FIG. 3. For ease of reference, the general structure of formula II is also shown (A). In particular, in some embodiments $R^1$ at C6 is $(CH_2)_2R^2$ and $R^2$ is selected from the group consisting of —$COCH_3$ (formula C), —COOH (formula D), and —C(OH) $CH_3$ (formula G). In other preferred embodiments, $R^1$ is $(CH_2)_3R^2$ and $R^2$ is —OH (formula E). In still further preferred embodiments, $R^1$ is selected from the group consisting of —$(CH_2)_3OSO_3H$ (formula F), —$(CH_2)_2CH(OSO_3H)CH_3$ (formula H), and —$(CH_2)_2COH$—$CH_3COOH$ (formula B). As for FIG. 2, formulas B-H in FIG. 3 are shown with only one substituted alkyl group, but as indicated by the $R^1$ groups at positions 2, 3, and 5, formulas having more than one substituted alkyl chain are contemplated and represent additional embodiments of the invention.

Figure 4:
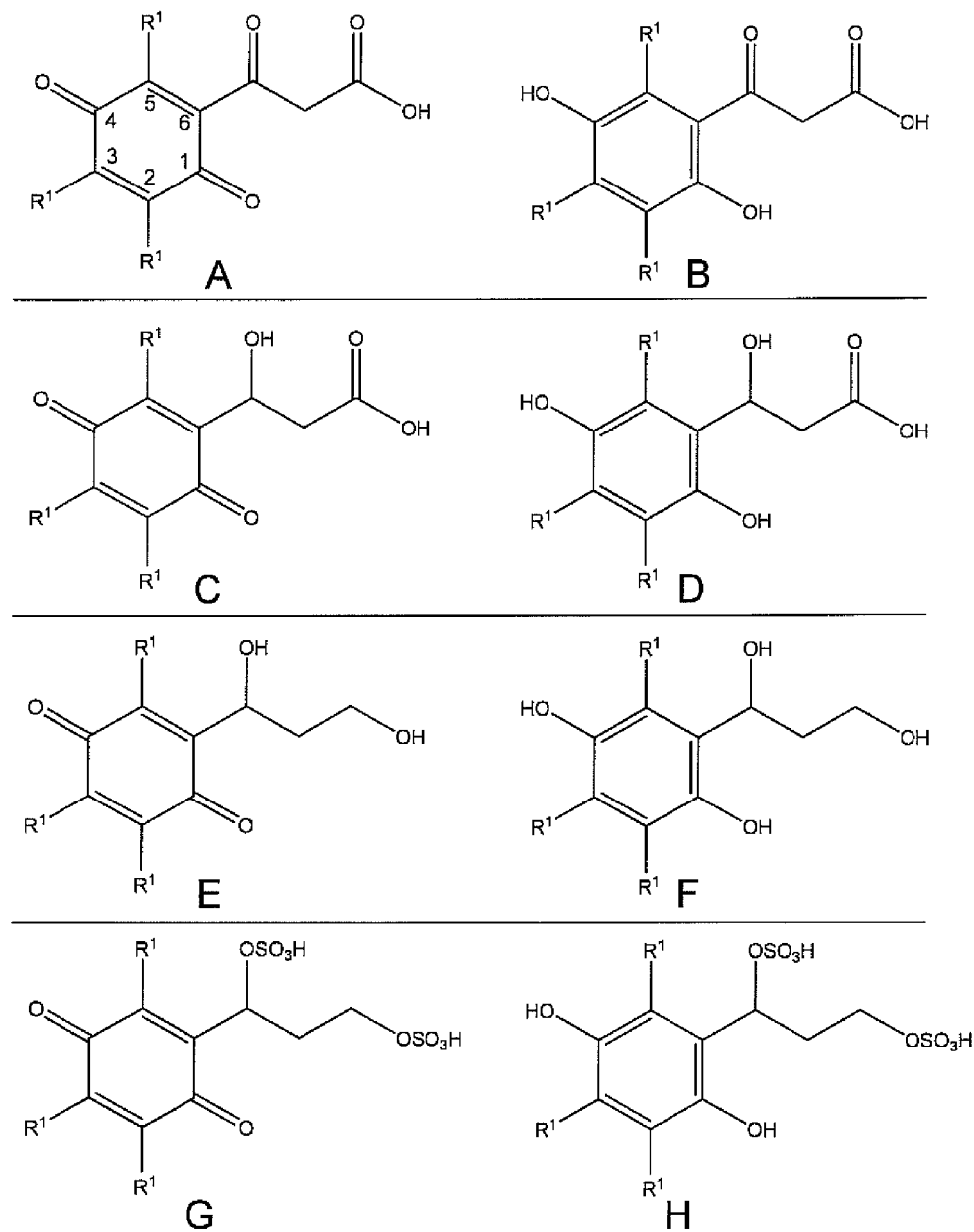
FIG. 4 provides certain exemplary embodiments of the photo-induced damage mitigating agents provided herein.

Further preferred embodiments of formulas I and II are provided in FIG. 4. Specifically, formulas shown at A, C, E, and G are embodiments of formula I, and formulas shown at B, D, F, and H are embodiments of formula II. Each of these formulas comprises at least two oxidizing or reducing groups on at least one substituted alkyl group extending from the ring. As for FIGS. 2 and 3, formulas in FIG. 4 are shown with only one substituted alkyl chain at C6, but as indicated by the $R^1$ groups at positions 2, 3, and 5, formulas having more than one substituted alkyl group are contemplated and represent additional embodiments of the invention. Further, the presence of two oxidizing and/or reducing groups on a substituted alkyl chain is in no way limiting and additional oxidizing and/or reducing groups on a single substituted alkyl chain are also included as additional embodiments of the invention.

Figure 5:
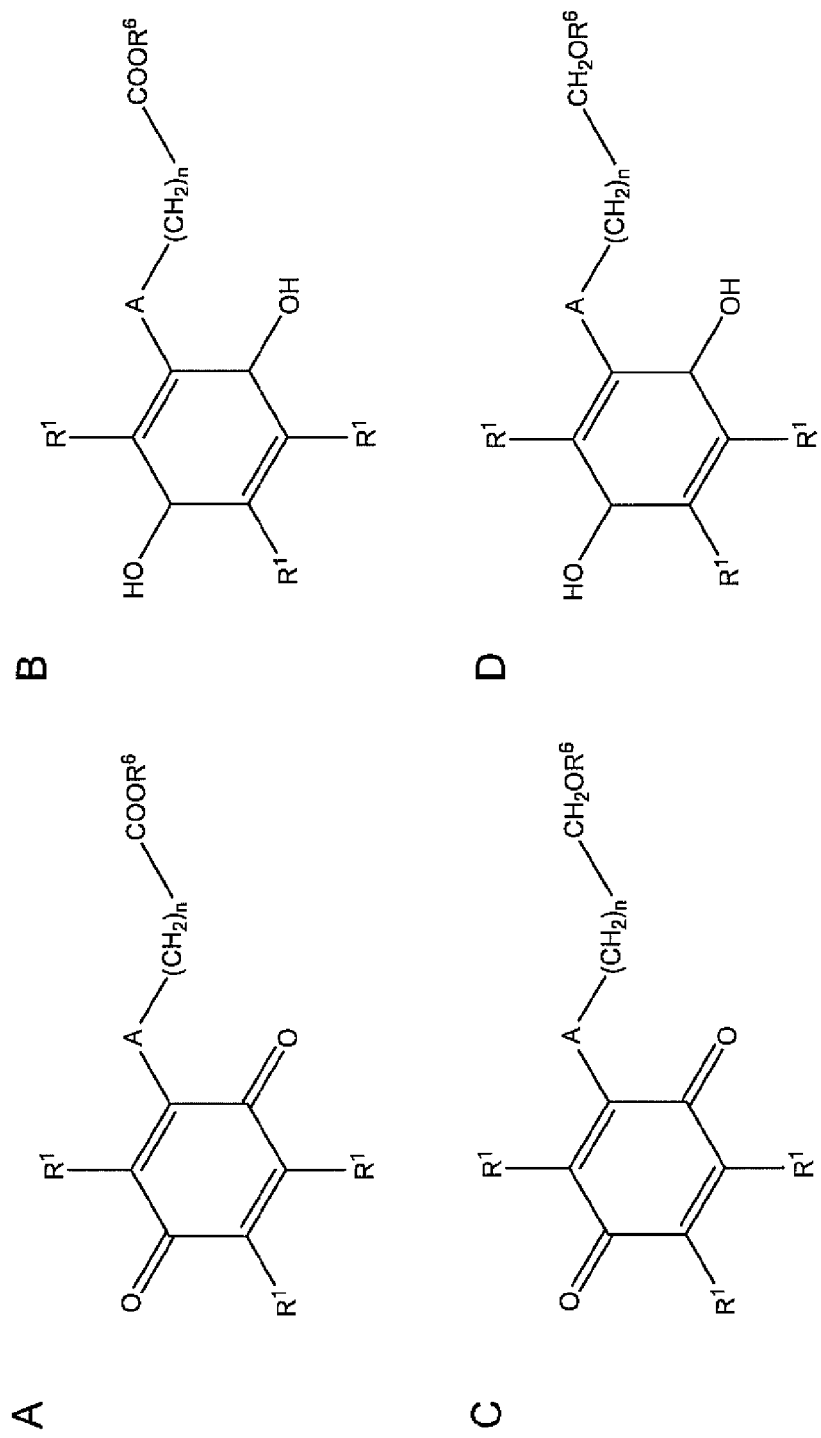
FIG. 5 provides certain exemplary embodiments of the photo-induced damage mitigating agents provided herein.

In certain preferred embodiments, the compound of formula I is compound A or C in FIG. 5, where A is —$CH_2$—, —CO—, —CH(OH)—, or —CH($OSO_3$H)—; n represents an integer from one to eight; and $R^6$ is a hydrogen, alkyl, $SO_3$H, acetate, or other group (see $R^1$-$R^5$ above). In certain preferred embodiments, the compound of formula II is compound B or D in FIG. 5, where A is —$CH_2$—, —CO—, —CH(OH)—, or —CH($OSO_3$H)—; n represents an integer from one to eight; and $R^6$ is a hydrogen, alkyl, $SO_3$H, acetate, or other group (see, e.g., $R^1$—$R^5$ above).

Figure 7:
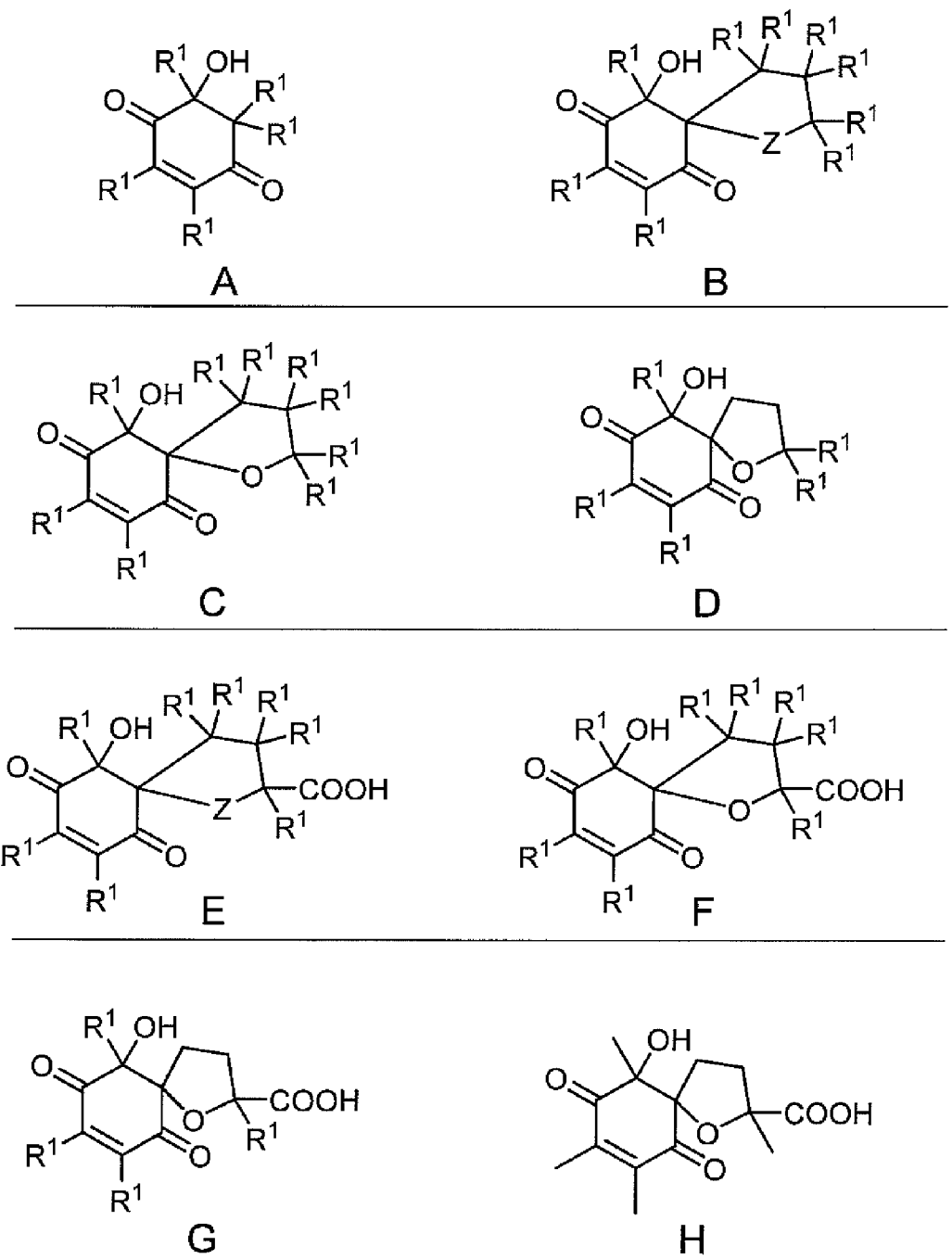
FIG. 7 illustrates certain exemplary embodiments of compounds of formula III.

Certain exemplary embodiments of photo-induced damage mitigating agents of formulas III are shown in FIG. 7. For ease of reference, the general structure of formula III is shown (A), and further embodiments of formula III are provided as formulas B, C, D, E, F. G, and H. The Z group can be essentially any bridging group, including but not limited to O, S, N—$R^1$, $(CH_2)_n$, CO, and combinations thereof. e.g., CONR, COO, $CH_2$O, and the like. The chemical name for formula H is 10-hydroxy-2,7,8,10-tetramethyl-6,9-dioxo-1-oxaspiro[4.5]dec-7-ene-2-carboxylic acid.

Figure 8:
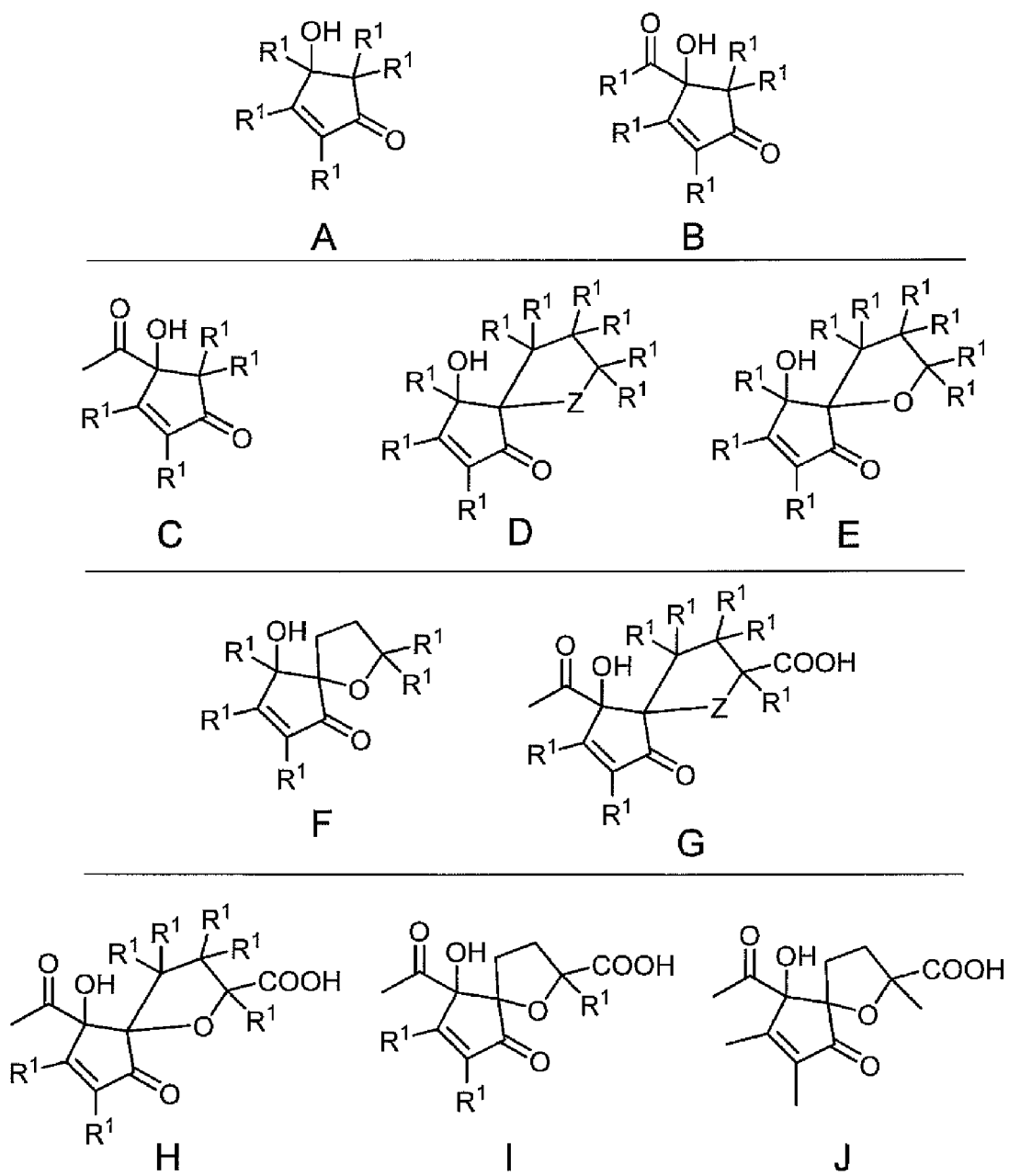
FIG. 8 illustrates certain exemplary embodiments of compounds of Formula IV.

Certain exemplary embodiments of photo-induced damage mitigating agents of formulas IV are shown in FIG. 8. For ease of reference, the general structure of formula IV is shown (A), and further embodiments of formula IV are provided as formulas B, C, D, E, F, G, H, and J. As above, the Z group can be essentially any bridging group, including but not limited to O, S, N—$R^1$, $(CH_2)_n$, CO, and combinations thereof, e.g., CONR, COO, $CH_2$O, and the like. The chemical name for formula J is 6-acetyl-6-hydroxy-2,7,8-trimethyl-9-oxo-1-oxaspiro[4.4]non-7-ene-2-carboxylic acid. A simplified scheme for the production of compounds of formula H in FIG. 7 and formula J in FIG. 8 is provided in FIG. 19.

Figure 21:
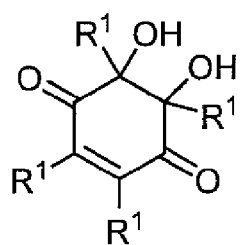
FIG. 21 illustrates certain exemplary embodiments of compounds of formula V.
Figure 21:
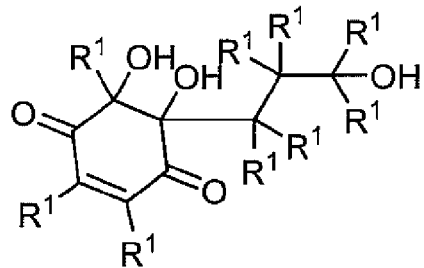
Figure 21:
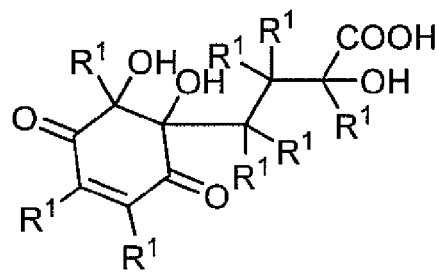
Figure 21:
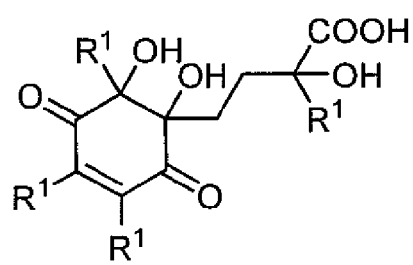
Figure 21:
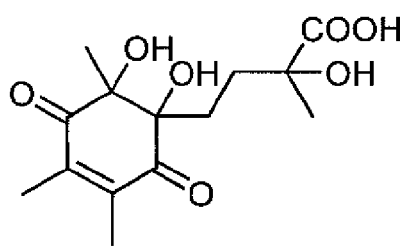

Certain exemplary embodiments of compounds of formula V are shown in FIG. 21. For ease of reference, the general structure of formula V is shown (A), and further embodiments of formula V are provided as formulas B, C, D, and E. The chemical name for formula E is 4-(1,6-dihydroxy-3,4,6-trimethyl-2,5-dioxocyclohex-3-enyl)-2-hydroxy-2-methylbutanoic acid.

Figure 22:
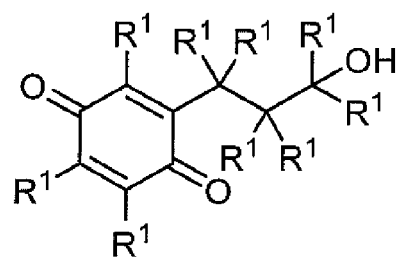
FIG. 22 illustrates certain exemplary embodiments of compounds of formula VI.
Figure 22:
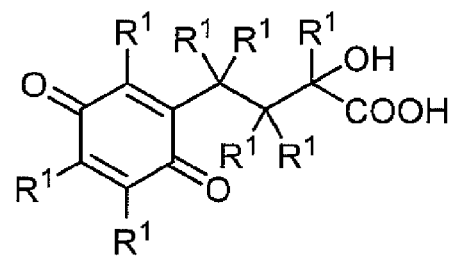
Figure 22:
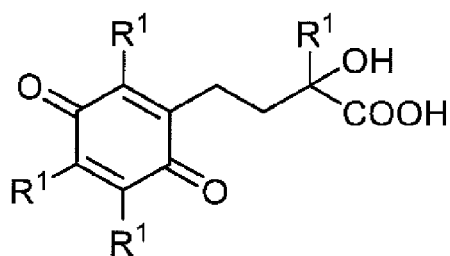
Figure 22:
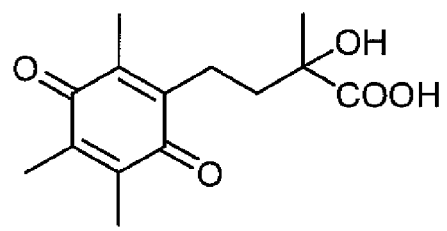

Certain exemplary embodiments of compounds of formula VI are shown in FIG. 22. As will be clear to one of ordinary skill, compounds of formula VI are also compounds of formula I, so all of the compounds depicted in FIG. 22 are also compounds of formula I. For ease of reference, the general structure of formula VI is shown (A), and further embodiments of formula VI are provided as formulas B, C, and D. The chemical name for formula D is 2-hydroxy-2-methyl-4-(2,4,5-trimethyl-3,6-dioxocyclohexa-1,4-dienyl)butanoic acid.

Figure 23:
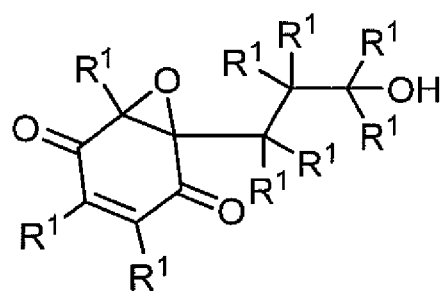
FIG. 23 illustrates certain exemplary embodiments of compounds of formula VII.
Figure 23:
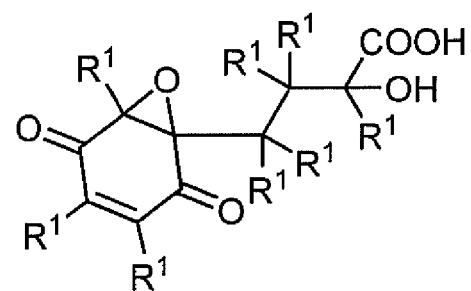
Figure 23:
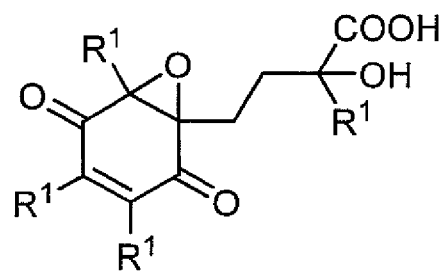
Figure 23:
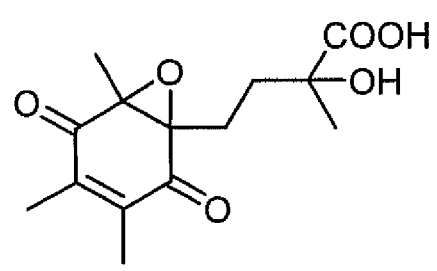

Certain exemplary embodiments of compounds of formula VII are shown in FIG. 23. For ease of reference, the general structure of formula VII is shown (A), and further embodiments of formula VII are provided as formulas B, C, and D. The chemical name for formula D is 2-hydroxy-2-methyl-4-(3,4,6-trimethyl-2,5-dioxo-7-oxabicyclo[4.1.0]hept-3-en-1-yl)butanoic acid.

Figure 24:
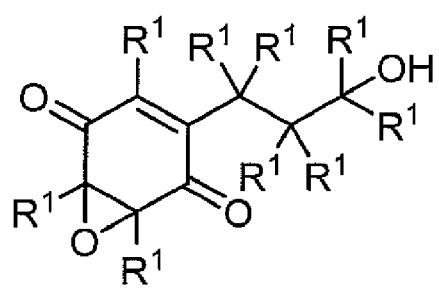
FIG. 24 illustrates certain exemplary embodiments of compounds of formula VIII.
Figure 24:
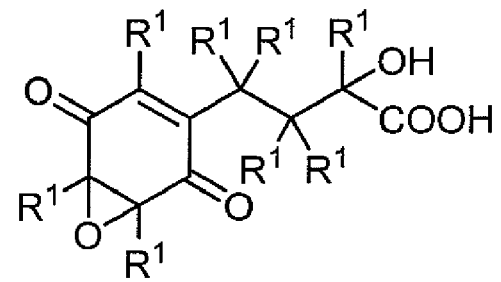
Figure 24:
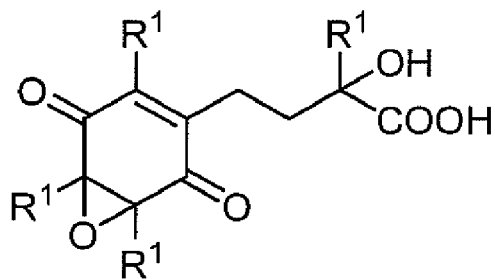
Figure 24:
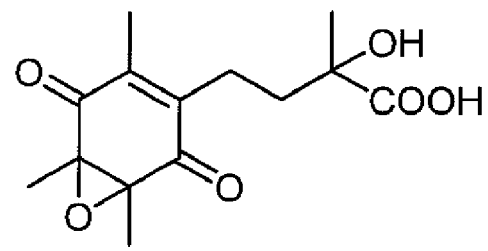

Certain exemplary embodiments of compounds of formula VIII are shown in FIG. 24. For ease of reference, the general structure of formula VIII is shown (A), and further embodiments of formula VIII are provided as formulas B, C, and D. The chemical name for formula D is 2-hydroxy-2-methyl-4-(1,4,6-trimethyl-2,5-dioxo-7-oxabicyclo[4.1.0]hept-3-en-3-yl)butanoic acid.

Figure 25:
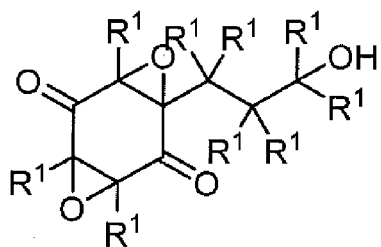
FIG. 25 illustrates certain exemplary embodiments of compounds of formula IX and X.
Figure 25:
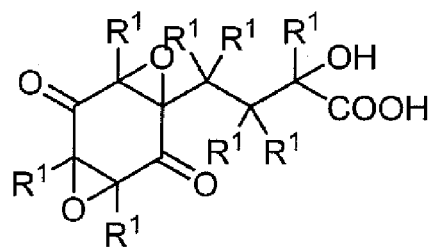
Figure 25:
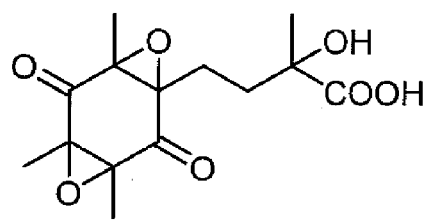
Figure 25:
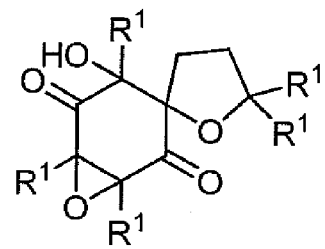
Figure 25:
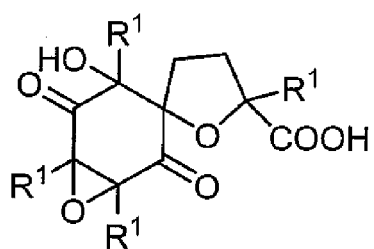
Figure 25:
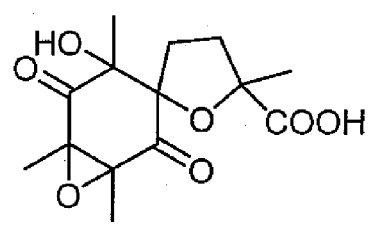

Certain exemplary embodiments of compounds of formula IX are shown in FIG. 25. For ease of reference, the general structure of formula IX is shown (A), and further embodiments of formula IX are provided as formulas B and C.

Certain exemplary embodiments of compounds of formula X are shown in FIG. 25. For ease of reference, the general structure of formula X is shown (D), and further embodiments of formula X are provided as formulas E, and F. The chemical name for formula F is 4-hydroxy-1,4,5',6-tetramethyl-2,5-dioxodihydro-3'H-7-oxaspiro[bicyclo[4.1.0]heptane-3,2'-furan]-5'-carboxylic acid.

Figure 26:
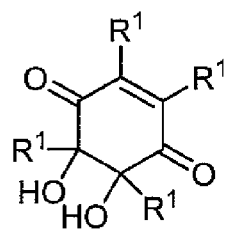
FIG. 26 illustrates certain exemplary embodiments of compounds of formula V.
Figure 26:
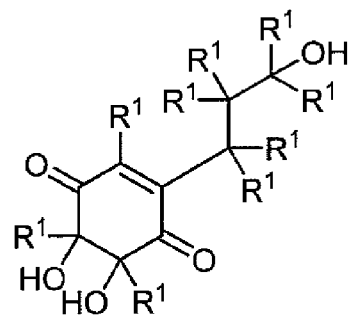
Figure 26:
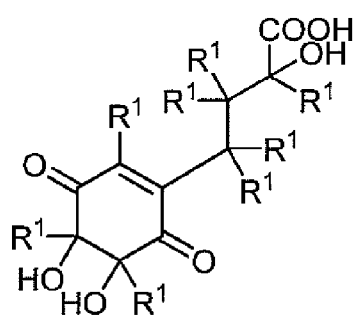
Figure 26:
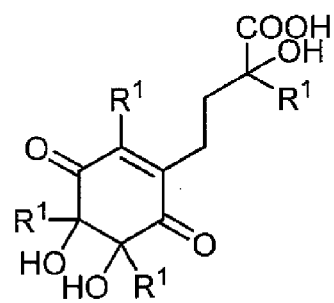
Figure 26:
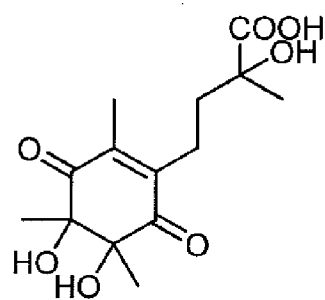

Certain exemplary embodiments of compounds of formula V are shown in FIG. 26. For ease of reference, the general structure of formula V is shown (A), and further embodiments of formula V are provided as formulas B, C, D, and E. The chemical name for formula E is 4-(4,5-dihydroxy-2,4,5-trimethyl-3,6-dioxocyclohex-1-enyl)-2-hydroxy-2-methylbutanoic acid.

In certain embodiments, the compounds provided may be used in combination with one another and/or with a variety of reducing agents, anti-fade agents, free radical quenchers/scavengers, singlet oxygen quenchers, and/or triplet-state quenchers (e.g., 6-hydroxy-2,5,7,8-tetramethylchroman-2-carboxylic acid), including, for example, those provided in U.S. Patent Publication No. 20070161017, previously incorporated by reference, which also provides methods of mitigating the impact of photo-induced damage on the results of a given analytical operation that may be used with the compounds and Methods of the provided herein.

In certain embodiments, a photo-induced damage mitigating agent is a mixture of at least two different quinone derivatives, e.g., at least about 2, 3, 4, 5, 6, or 7 quinone derivatives provided herein. Such a mixture can comprise various ratios of any two of its constituent quinone derivatives, e.g., about 20:1, 10:1, 8:1, 6:1, 4:1, 2:1, 3:2, 1.5:1 1:1, 1:1.5, 2:3, 1:2, 1:4, 1:6, 1:8, 1:10, 1:20, etc. For example, there may be substantially equivalent amounts of multiple or each quinone derivative in the mixture, and/or at least one quinone derivative may be at a significantly higher concentration than at least one other. In some preferred embodiments, a mixture of at least two different quinone derivatives provided herein comprises various percentages of its constituent derivatives, e.g., less than about 95%, 85%, 75%, 65%, 55%, 45%, 35%, 25%, 15%, 10%, or 5%. Further, such mixtures may comprise various ranges of percentages for its constituent derivatives, such as, e.g., 5-10%, 10-15%, 10-20%, 20-30%, and the like. In certain embodiments, at least one quinone derivative is below a threshold level, e.g., below 5%, 4%, 3%, 2%, or below 1%. In certain embodiments, other components of a mixture comprising quinone derivatives of the invention fall within the ratios, percentages, and/or ranges provided herein. In certain embodiments, percentages of quinone derivatives in a mixture are relative to the initial total concentration of a starting compound from which they are derived, but such percentages may alternatively or additionally be relative to the total concentration of all quinone derivatives in a mixture. For example, in certain methods described herein a solution of 6-hydroxy-2,5,7,8-tetramethylchroman-2-carboxylic acid is treated to produce a mixture of quinone derivatives and the resulting percentages of these derivatives is relative to the initial total concentration of the 6-hydroxy-2,5,7,8-tetramethylchroman-2-carboxylic acid prior to the treatment.

In some preferred embodiments, a photo-induced damage mitigating agent is a mixture comprising at least one benzoquinone derivative of formula I and at least one hydroquinone derivative of formula II. In certain preferred embodiments, a photo-induced damage mitigating agent is a mixture of at least two or more quinone derivatives of formulas III, IV, V, VI, VII, VIII, IX, and X, preferably at least one of formula III and another of formula IV. In certain embodiments, at least one quinone derivative of each of formulas III and IV are present in a photo-induced damage mitigating agent, e.g., in a photo-induced damage mitigating agent admixture. In other preferred embodiments, a photo-induced damage mitigating agent is a mixture of at least one photo-induced damage mitigating agent that is not a quinone derivative of formula I, II, III, IV, V, VI, VII, VIII, IX, and X and at least one quinone derivative of formula I, II, III, IV, V, VI, VII, VIII, IX, and X. For example, data showing an increase in enzyme processivity in the presence of various mixtures comprising 6-hydroxy-2,5,7,8-tetramethylchroman-2-carboxylic acid and a benzoquinone derivative of formula I are provided in Example 5 and FIG. 13, below. In addition, data showing enzyme processivity in the presence of mixtures comprising quinone derivatives of the invention are provided in Example 7 and FIG. 17, below.

In certain embodiments, a quinone derivative mixture of the invention comprises at least about 5%, 10%, 15%, 20%, 30%, or 50; or less than about 50%, 30%, 20%, 15%, 10%, or 5% of a single quinone derivative therein. In certain embodiments, a quinone derivative mixture of the invention comprises at least 5%, 10%, 15%, or 20%; or less than about 30%, 20%, 15%, 10%, or 5% of multiple quinone derivatives therein. For example, in certain preferred embodiments, a quinone derivative mixture of the invention comprises at least about 5-40% of at least one quinone derivative of formula III, e.g., of formula H in FIG. 7. In other preferred embodiments, a quinone derivative mixture of the invention comprises at least about 5-40% of at least one quinone derivative of formula IV, e.g., of formula J in FIG. 8. In other preferred embodiments, a quinone derivative mixture comprises at least about 1-10% of each of multiple quinone derivatives of formulas III, IV, V, VI, VII, VIII, IX, and X. In yet further embodiments, a quinone derivative mixture comprising at least about 2-15% of each of multiple quinone derivatives of formulas III, IV, V, VI, VII, VIII, IX, and X further comprises at least about 2-15% or less than about 10% of at least one quinone derivative of formula I and/or II. Further, certain quinone derivative mixtures also comprise 6-hydroxy-2,5,7,8-tetramethylchroman-2-carboxylic acid, e.g. less than about 20%, or 10% or 5%. As noted elsewhere herein, these percentages describing quinone derivative mixtures of the invention refer to percentages present in admixtures prior to addition to an analytical reaction of interest, regardless of changes in such percentages that may occur upon or subsequent to such addition, e.g., during the course of the analytical reaction. As such, the term "photo-induced damage mitigating agent admixture" indicates a mixture comprising one or more photo-induced damage mitigating agents to be added to a reaction mixture wherein such percentages may change. A photo-induced damage mitigating agent admixture may further comprise additional components, e.g., buffers, salt, or other reagents necessary for initiation and/or progression of a reaction of interest, such as enzymes, substrates, cofactors, and the like.

These approaches are particularly useful in the optical interrogation of reactions where components of the reaction that are susceptible to photo-induced damage are spatially confined on an assay plate or substrate, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like.

In accordance with the present invention, photo-induced damage mitigating agents may generally be provided as a component of the reaction mixture, either through addition as an additive, either liquid or solid, or through predisposition and/or immobilization of the photo-induced damage mitigating agents within the region where the reaction is taking place. By way of example, in cases where the reaction of interest is confined to a particular region or location, it may be desirable to immobilize or otherwise localize the photo-induced damage mitigating agents within or proximal to that region. Likewise, where a photo-induced damage mitigating agent comprises cooperatively functioning components, e.g., dual enzyme systems, it may again be desirable to localize such components relative to each other, as well as to the reaction of interest.

In some cases, the photo-induced damage mitigating agents may be immobilized upon the surfaces of the substrates or reactions wells, or may be provided in a configuration that permits them to freely interact with the aqueous system components by including such agents within or linked to structures (e.g., caging groups, tridentate structures, etc.) that render the agents suspended in aqueous systems and additionally available to interact with relevant portions of the reaction mixture, e.g., dissolved oxygen species.

As used herein, a substrate may comprise any of a variety of formats, from planar substrates, e.g., glass slides or planar surfaces within a larger structure, e.g., a multi-well plates such as 96-well, 384-well, and 1536-well plates, or regularly spaced micro- or nano-porous substrates. Such substrates may also comprise more irregular porous materials, such as membranes, aerogels, fibrous mats, or the like, or they may comprise particulate substrates, e.g., beads, spheres, metal or semiconductor nanoparticles, optical fibers, or the like.

In addition to the foregoing, it will be appreciated that the other reagents in a given reaction of interest, including those reagents for which photo-induced damage is being mitigated in accordance with the invention, may be provided in any of a variety of different configurations. For example, they may be provided free in solution, or complexed with other materials, e.g., other reagents and/or solid supports. Likewise, such reagents may be provided coupled to beads, particles, nanocrystals or other nanoparticles, or they may be tethered to larger solid supports, such as matrices or planar surfaces. These reagents may be further coupled or complexed together with other reagents, or as separate reagent populations or even as individual molecules, e.g., that are detectably resolvable from other molecules within the reaction space. In addition, for purposes of discussion herein, whether a particular reagent is confined by virtue of structural barriers to its free movement or is chemically tethered or immobilized to a surface of a substrate, it will be described as being "confined." For example, in some preferred embodiments, one or more reagents in an assay system are confined within an optical confinement. Such an optical confinement may be an internal reflection confinement (IRC) or an external reflection confinement (ERC), a zero mode waveguide, or an alternative optical structure, such as one comprising porous film with reflective index media or a confinement using index matching solids. More detailed descriptions of various types of optical confinements are provided, e.g., in International Application Publication No. WO/2006/083751, U.S. Pat. No. 6,917,726, and U.S. Pat. No. 7,170,050, the full disclosures of which are incorporated herein by reference in their entireties for all purposes.

V. Exemplary Applications

As noted above, the methods and compositions of the invention are useful in a broad range of illuminated analytical reactions, and particularly those using photoluminescent or fluorescent reactants, and particularly such reactions where the reagents that are susceptible to photo-induced damage are present at relatively low levels. One exemplary application of the methods and compositions described herein is in single molecule analytical reactions, where the reaction of a single molecule (or very limited number of molecules) is observed in the analysis, such as observation of the action of a single enzyme molecule. In particular, when an analysis relies upon a small population of reagent molecules, damage to any significant fraction of that population will have a substantial impact on the analysis being performed. For example, prolonged interrogation of a limited population of reagents, e.g., fluorescent analogs and enzymes, can lead to photo-induced damage of the various reagents to the point of substantially impacting the activity or functionality of the enzyme. In particular, it has been shown that prolonged illumination of DNA polymerases involved in synthesis using fluorescent nucleotide analogs results in a dramatic decrease in the enzyme's ability to synthesize DNA, often measured as a reduction in processivity. Without being bound to any theory of operation, it is believed that in some cases the photo-induced damage event affects the catalytic region of the enzyme thus affecting either the ability of the enzyme to remain complexed with the template, or its ability to continue synthesis. The compositions and methods of the present invention can prevent or mitigate that impact by providing photo-induced damage mitigating agents in the reaction mixture.

As will be appreciated, the photo-induced damage of illuminated reactions sought to be prevented by the methods and compositions of the invention is not merely photo-induced damage to fluorescent reagents, e.g., photobleaching, but also includes the prevention or reduction of the downstream effects of photoactivation. In small volumes, reagents with a limited presence are greatly impacted by even slight losses due to photo-induced damage, particularly reactive proteins or enzymes. This damage, without being bound to a theory of operation, may include damage to the enzymes or reactive proteins or irreversible interactions between such enzymes or proteins and the photo-induced damaged reagents. Typically, such damage directly impacts either the reactant of interest, e.g., direct photo-induced damage, or impacts a reactant within one, two or three reactive steps of such reactant of interest.

In one aspect, the present invention is directed to illuminated reaction mixtures which include one or more agents that function to block or otherwise minimize the pathways that lead to damage due to the creation of reactive oxygen species during an illuminated reaction. Photo-induced damage mitigating agents include quinone derivatives, as described herein, as well as reducing agents or anti-fade agents, such as those that prevent photo-induced damage resulting from the presence of triplet-state fluorophores (also referred to as triplet-state quenchers) that can form during the course of an illuminated reaction. Photo-induced damage mitigating agents also include oxygen scavenging agents, which remove oxygen and reactive oxygen species from the reaction mixture. Such photo-induced damage mitigating agents are able to alleviate and/or prevent photo-induced damage by blocking the damage such species may cause to one or more reactants, particularly conjugates that include a dye.

In general, the photo-induced damage mitigating agents described herein are present in the reaction mixture at levels sufficient to provide beneficial impact, e.g., reduced photo-induced damage and/or extension of the photo-induced damage threshold period, but are not present at such levels as to interfere with the reaction of interest, e.g., the sequencing reaction. In certain preferred embodiments, the photo-induced damage mitigating agents are present at 0.5-10.0 mM, or more preferably between about 0.5 mM and 5 mM, which represents the total concentration of a single or a combination of photo-induced damage mitigating agents presented herein. However, these concentrations are merely exemplary and may be change depending on various factors including, e.g., the particular photo-induced damage mitigating agent and/or mixture thereof, the type of reaction to which it is added, conditions under which such reaction is to be performed, and the like. Such adjustments are well within the abilities of the ordinary practitioner.

In another aspect of the invention, the photo-induced damage mitigating agents described herein are particularly suitable for mitigating photo-induced damage to reactants in small reaction volume concentrations, wherein such reactants may be present in solution, but at very limited concentrations, e.g., less than 200 nM, in some cases less than 10 nM, and in still other cases less than 10 pM. In certain embodiments, such limited quantity reagents or reactants refer to reactants that are immobilized or otherwise confined within a given area, so as to provide a limited quantity of reagents in that given area, and in certain cases, provide small numbers of molecules of such reagents within that given area, e.g., from 1 to 1000 individual molecules, preferably between 1 and 10 molecules. As will be appreciated, photo-induced damage of immobilized reactants in a given area will have a substantial impact on the reactivity of that area, as other, non-damaged reactants are not free to diffuse into the reaction volume and mask the damage effects.

In yet another aspect, the present invention is directed to illuminated reactions for single molecule analysis, including sequencing of nucleic acids by observing incorporation of nucleotides into a nascent nucleic acid sequence during template-directed polymerase-based synthesis. Such methods, generally referred to as "sequencing-by-incorporation," involve the observation of the addition of nucleotides or nucleotide analogs in a template-dependent fashion in order to determine the sequence of the template strand. See, e.g., U.S. Pat. Nos. 6,780,591, 7,037,687, 7,344,865, 7,302,146, and Eid, et al. (2009) Science 323:133-138, all of which are incorporated herein by reference in their entireties for all purposes. Processes for performing this detection include the use of fluorescently labeled nucleotide analogs within a confined observation region, e.g., within a nanoscale well and/or tethered, either directly or indirectly to a surface, By using excitation illumination (i.e., illumination of an appropriate wavelength to excite the fluorescent label and induce a detectable signal), the fluorescently labeled bases can be detected as they are incorporated into the nascent strand, thus identifying the nature of the incorporated base, and as a result, the complementary base in the template strand.

One particularly preferred aspect of the invention is in conjunction with the sequencing by incorporation of nucleic acids within an optical confinement, such as a zero mode waveguide, Such reactions involve observation of an extremely small reaction volume in which one or only a few polymerase enzymes and their fluorescent substrates may be present. Zero mode waveguides, and their use in sequencing applications are generally described in U.S. Pat. Nos. 6,917,726 and 7,033,764, and preferred methods of sequencing by incorporation are generally described in Published U.S. Patent Application No. 2003-0044781, the full disclosures of which are incorporated herein by reference in their entireties for all purposes, and in particular for their teachings regarding such sequencing applications and methods. Briefly, arrays of zero mode waveguides ("ZMWs"), configured in accordance with the present invention may be employed as optical confinements for single molecule analytical reactions, e.g., for nucleic acid (e.g., DNA, RNA) sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, which is immobilized at the base of the ZMW, may then be specifically observed during synthesis to monitor incorporation of nucleotides in a template dependent fashion, and thus provide the identity and sequences of nucleotides in the template strand. This identification is typically accomplished by providing detectable label groups, such as fluorescent labeling molecules, on the nucleotides. In some instances, the labeled nucleotides terminate primer extension, allowing a "one base at a time" interrogation of the complex. If, upon exposure to a given labeled base, a base is incorporated, its representative fluorescent signal may be detected at the base of the ZMW. If no signal is detected, then the base was not incorporated and the complex is interrogated with each of the other bases, in turn. Once a base is incorporated, the labeling group is removed, e.g., through the use of a photocleavable linking group, and where the label was not the terminating group, a terminator, upon the 3' end of the incorporated nucleotide, may be removed prior to subsequent interrogation.

In accordance with the present invention, the above-described sequencing reaction may be carried out in the presence of one or more photo-induced damage mitigating agents (e.g., quinone derivatives, and conjugates and mixtures thereof) provided herein, either alone or in combination with other reaction mixture additives, such as reducing agents, antifade agents, free radical quenchers, triplet-state quenchers, singlet oxygen quenchers, or enzyme systems for depletion of oxygen species (e.g., comprising an oxidase). In certain preferred embodiments, the sequencing reactions may be carried out in the presence of at least one quinone derivative described herein. For example, a photo-induced damage mitigating agent may be a mixture comprising at least one hydroquinone derivative and at least one benzoquinone derivative, or at least two compounds of formulas I, II, III. IV, V, VI, VII, VIII, IX, and X. In certain embodiments, a photo-induced damage mitigating agent may be a mixture comprising at least one compound of formula III and at least one compound of formula IV. In certain embodiments, a photo-induced damage mitigating agent may be a mixture comprising one or more compounds of formulas III and IV and at least one compound of formula I. Further, a photo-induced damage mitigating agent may be a mixture comprising 6-hydroxy-2,5,7,8-tetramethylchroman-2-carboxylic acid and at least one quinone derivative provided herein. In a particularly preferred aspect, the illuminated reaction mixture includes a nucleoside polyphosphate connected to a fluorescent dye by a linker. The linker in such a reaction mixture itself may comprise one or more photo-induced damage mitigating agents, such as the quinone derivatives (or mixtures thereof) provided herein.

In addition to the use of photo-induced damage mitigating agents, the present invention also provides alternative methods of mitigating the impact of photo-induced damage on a reaction. Such alternative methods can be used in combination with the compositions and methods described above to further alleviate the effects of species that can be generated during an illuminated reaction.

One alternative method of mitigating the impact of photo-induced damage on the results of a given reaction is by only interrogating a reaction mixture, e.g., detecting fluorescent emission, during such portion of the illumination period before which excessive photo-induced damage has occurred. This approach is particularly useful in the optical interrogation of reactions where components of the reaction that are susceptible to photo-induced damage are spatially confined on an assay plate or substrate, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like.

Another alternative method of mitigating the impact of photo-induced damage on the results of a given reaction provides for the elimination of potentially damaging oxygen species using means other than the use of the photo-induced damage mitigating agents described above. In one example, dissolved oxygen species may be flushed out of aqueous systems by providing the reaction system under different gas environments, such as by exposing an aqueous reaction to neutral gas environments, such as argon, nitrogen, helium, xenon, or the like, to prevent dissolution of excess oxygen in the reaction mixture. By reducing the initial oxygen load of the system, it has been observed that photo-induced damage effects, e.g., on polymerase mediated DNA synthesis, is markedly reduced. In particularly preferred aspects, the system is exposed to a xenon atmosphere. In particular, since xenon can be induced to form a dipole, it operates as a triplet-state quencher in addition to supplanting oxygen in the aqueous system. (See, e.g., Vierstra and Poff, Plant Physiol. 1981 May; 67(5): 996-998, which is incorporated herein by reference in its entirety for all purposes) As such, xenon would also be categorized as a quencher, as set forth above.

These and further examples of alternative methods of mitigating photo-induced damage which can be used in combination with methods and compositions of the invention described herein are provided in commonly owned U.S. Patent Publication No. 20070036511, which is incorporated herein by reference in its entirety for all purposes and in particular for disclosure related to these methods of mitigating photo-induced damage.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

The following non-limiting examples are provided to further illustrate the invention.

VI. Examples

Example 1

FCS Analysis of 6-hydroxy-2,5,7,8-tetramethylchroman-2-carboxylic acid Derivatives Because of the value of single molecule analysis in nucleic acid sequencing applications, DNA polymerase systems were used to identify and analyze the photo-induced damage mitigating agents and methods of use thereof in accordance with the present invention.

6-hydroxy-2,5,7,8-tetramethylchroman-2-carboxylic acid is a vitamin E derivative that has been used to reduce radiation-induced damage, e.g., for fluorescent probes, and is generally commercially available from Sigma-Aldrich (St. Louis, MO). Surprisingly, it has been discovered that photomodified derivatives of this compound provide substantially better mitigation of photo-induced damage over the unmodified compound in illuminated sequencing reactions. Given the conventional use of the unmodified compound, the ability of photomodified versions of the compound to yield better performance in mitigating photo-induced damage was surprising.

A solution of photomodified 6-hydroxy-2,5,7,8-tetramethylchroman-2-carboxylic acid was prepared by adding 0.2966 grams of 6-hydroxy-2,5,7,8-tetramethylchroman-2-carboxylic acid to 1.278 mL of methanol and 9.58 mL of HPLC water. Drops of 1M KOH were added to the mixture until it became a uniformly transparent solution. The solution was irradiated for one hour under a UV lamp, and was subsequently exposed to room-light irradiation at room temperature for 18 hours.

Fluorescence correlation spectroscopy (FCS) is a commonly used technique for experimentally characterizing the dynamics of fluorescent species that was initially introduced in the early 1970's (Magde, D., et al, (1972) *Phys. Rev. Lett.* 29: 705-708). In FCS, light is focused on a sample in a very small detection volume, and the measured fluorescence intensity fluctuations (due to diffusion, physical or chemical reactions, aggregation, etc.) are analyzed using the temporal autocorrelation. Further details are provided, e.g., in Ehrenberg, M. et al. (1974) *Chem Phys* 4: 390-401; Elson, E. L., et al. (1974) *Biopolymers* 13: 1-27; Magde, D., et al. (1974) *Biopolymers* 13: 29-61; Thompson, N. L. (1991) Topics in Fluorescence Spectroscopy Techniques, Vol. 1, ed. J. R. Lakowicz (New York: Plenum) pp. 337-378; Hess, et al. (2002) *Biochemistry* 41: 697; and Krichevsky, O., et al. (2002) *Rep. Prog. Phys.* 65: 251-297.

FCS experiments using the fluorophore Alexa568 in low oxygen were used to monitor the amount of the dye triplet state upon excitation over time as a measure of triplet-state quenching by 6-hydroxy-2,5,7,8-tetramethylchroman-2-carboxylic acid and derivatives thereof. Briefly, these experiments were performed on a confocal microscope setup (Olympus IX71 with water-immersion objective UPlanSApo, 60×) using a single line laser excitation (532 nm) at 0.4-mW intensity and two single photon avalanche detectors (SPAD detectors; Perkin Elmer, Waltham, Mass.). The FCS measurements were done in a reaction buffer containing 50 mM ACES, pH 7.1; 75 mM potassium acetate; and 5 mM DTT. A protocatechuic acid/protocatechuate-3,4-dioxygenase (PCA/PCD) oxygen scavenging system (see, e.g., Aitken, et al. (2007) "An Oxygen Scavenging System for Improvement of Dye Stability in Single-Molecule Fluorescence Experiments," Biophys J. 94:1826-1835) was included, as well. Correlation curves were generated and recorded by a FLEX digital photon correlator (Correlator.com; Bridgewater, N.J.), and analyzed using Origin8.0 (OriginLabs; Northampton, Mass.).

In these experiments, the photo-induced damage mitigating ability of the preparation of photomodified 6-hydroxy-2,5,7,8-tetramethylchroman-2-carboxylic acid (described above), an aged 6-hydroxy-2,5,7,8-tetramethylchroman-2-carboxylic acid solution (stored at −20° C. for ~1 year), a freshly prepared 6-hydroxy-2,5,7,8-tetramethylchroman-2-carboxylic acid solution (prepared according to manufacturer's instructions), and fresh preparations treated with various UV exposure regimes were compared. The results are plotted as autocorrelation curves in FIG. 9, and the amplitude of the "hump" at around one microsecond (0.001 millisecond (ms)) to a few microseconds indicates the triplet fraction of the dye, so the smaller the amplitude, the better the triplet quencher. The greatest triplet-state quenching was seen with the new preparation of photomodified 6-hydroxy-2,5,7,8-tetramethylchroman-2-carboxylic acid ("Freshly prepared, 1 hr UV, 18 hr room-light irradiation") with an autocorrelation amplitude of ~0.065 at a lag time of 0.001 ms. The aged solution was the second best performer with an autocorrelation amplitude of ~0.07 at a lag time of 0.001 ms. The freshly prepared solution not treated with UV was the least effective triplet-state quencher with an autocorrelation function of ~0.2 at a lag time of 0.001 ms, and in general, increasing times of UV treatment increased effectiveness of triplet-state quenching by these solutions, although there were not large differences between the quenching ability of the solutions exposed for three, six, and 24 hours.

Example 2

Figure 10:
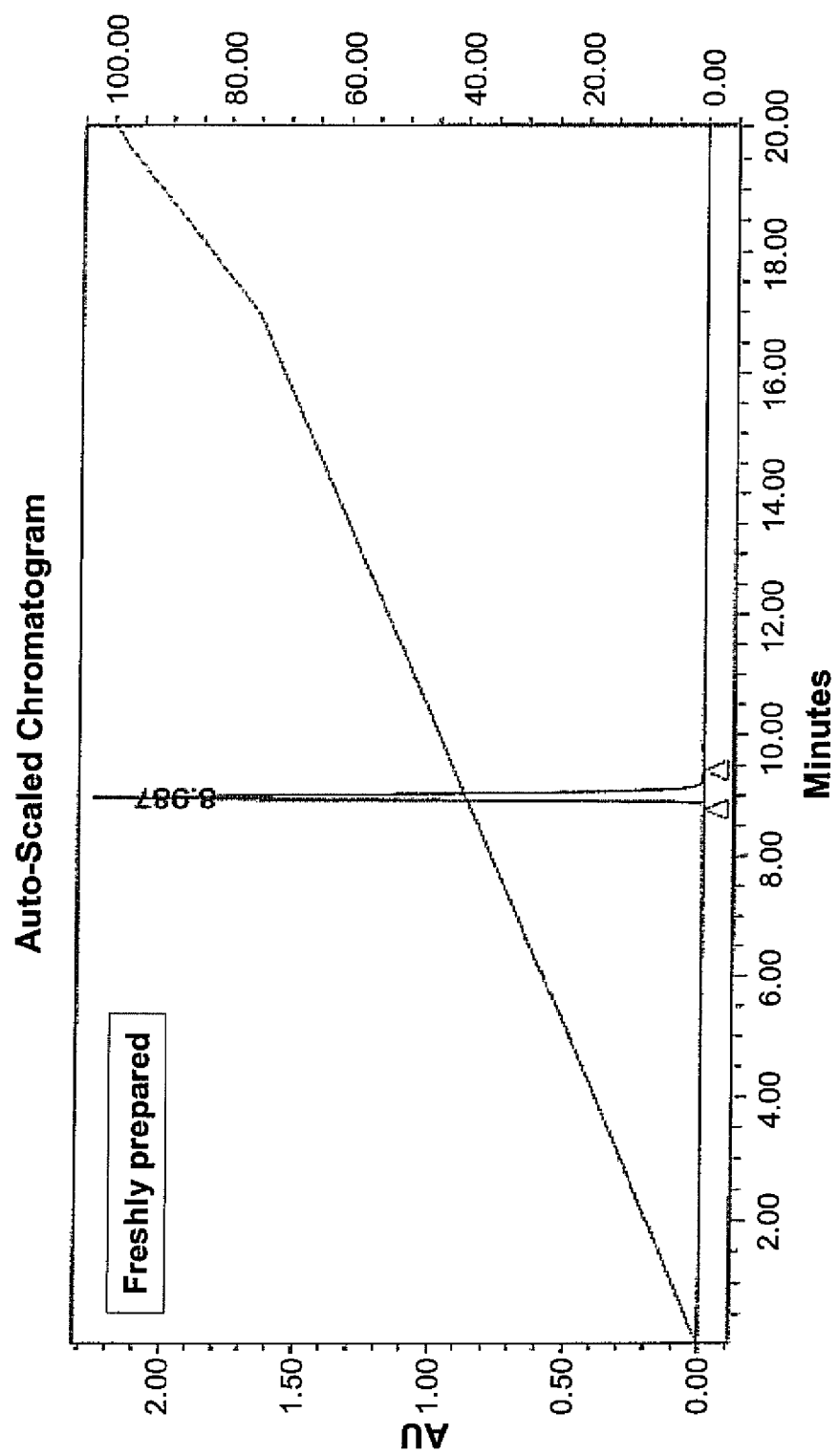
FIG. 10 shows reverse phase HPLC traces for 6-hydroxy-2,5,7,8-tetramethylchroman-2-carboxylic acid (A), photo-modified 6-hydroxy-2,5,7,8-tetramethylchroman-2-carboxylic acid solutions (B, C), Fraction A (D), and Fraction B (E).

HPLC Analysis of Photomodified 6-hydroxy-2,5,7,8-tetramethylchroman-2-carboxylic acid Solution Multiple procedures were developed for preparing photomodified 6-hydroxy-2,5,7,8-tetramethylchroman-2-carboxylic acid solutions. A first, described above, involves exposing a freshly prepared solution to UV irradiation for one hour followed by 18 hours of room-light irradiation. In a second, a freshly prepared solution was irradiated for 36 hours under a UV lamp. Reverse phase HPLC was performed on a freshly prepared solution of 6-hydroxy-2,5,7,8-tetramethylchroman-2-carboxylic acid and photomodified solutions prepared by these two methods. The top trace in FIG. 10A shows that freshly prepared 6-hydroxy-2,5,7,8-tetramethylchroman-2-carboxylic acid ran as a single species on reverse phase HPLC with a migration time of 8.987 minutes. The second trace (B) shows the peaks in the mixture produced by treating the fresh solution with UV light for one hour, followed by exposure to room-light radiation for 18 hours at room temperature. 6-hydroxy-2,5,7,8-tetramethylchroman-2-carboxylic acid and a first derivative termed "Fraction A" are clearly visible with migration times of 9.008 minutes and 9.791 minutes, respectively. The third trace (C) shows the peaks in the mixture produced by treating the fresh solution with UV light for 36 hours. 6-hydroxy-2,5,7,8-tetramethylchroman-2-carboxylic acid (migration time 8.969 minutes) and two major derivatives are clearly visible. The derivative with a migration time of 9.756 minutes was identified as "Fraction A" and the derivative with a migration time of 14.8501 minutes was termed "Fraction B." These two derivatives of 6-hydroxy-2,5,7,8-tetramethylchroman-2-carboxylic acid were purified and analyzed by reverse phase HPLC, as shown in FIG. 10D and FIG. 10E. The purified Fraction A had a major peak with a migration time of 9391 minutes (D), and the purified Fraction B had a major peak with a migration time of 14.919 minutes (E).

Example 3

Fluorescence Correlation Spectroscopy

The effectiveness of the photomodified solutions and the purified Fraction A and Fraction B as triplet-state quenchers/radical scavengers was tested by fluorescence correlation spectroscopy (FCS) using Alexa568 in low oxygen, as described above in Example 1. Two different intensity of excitation settings, 0.2 mW and 0.4 mW, were used for power dependence.

Figure 11:
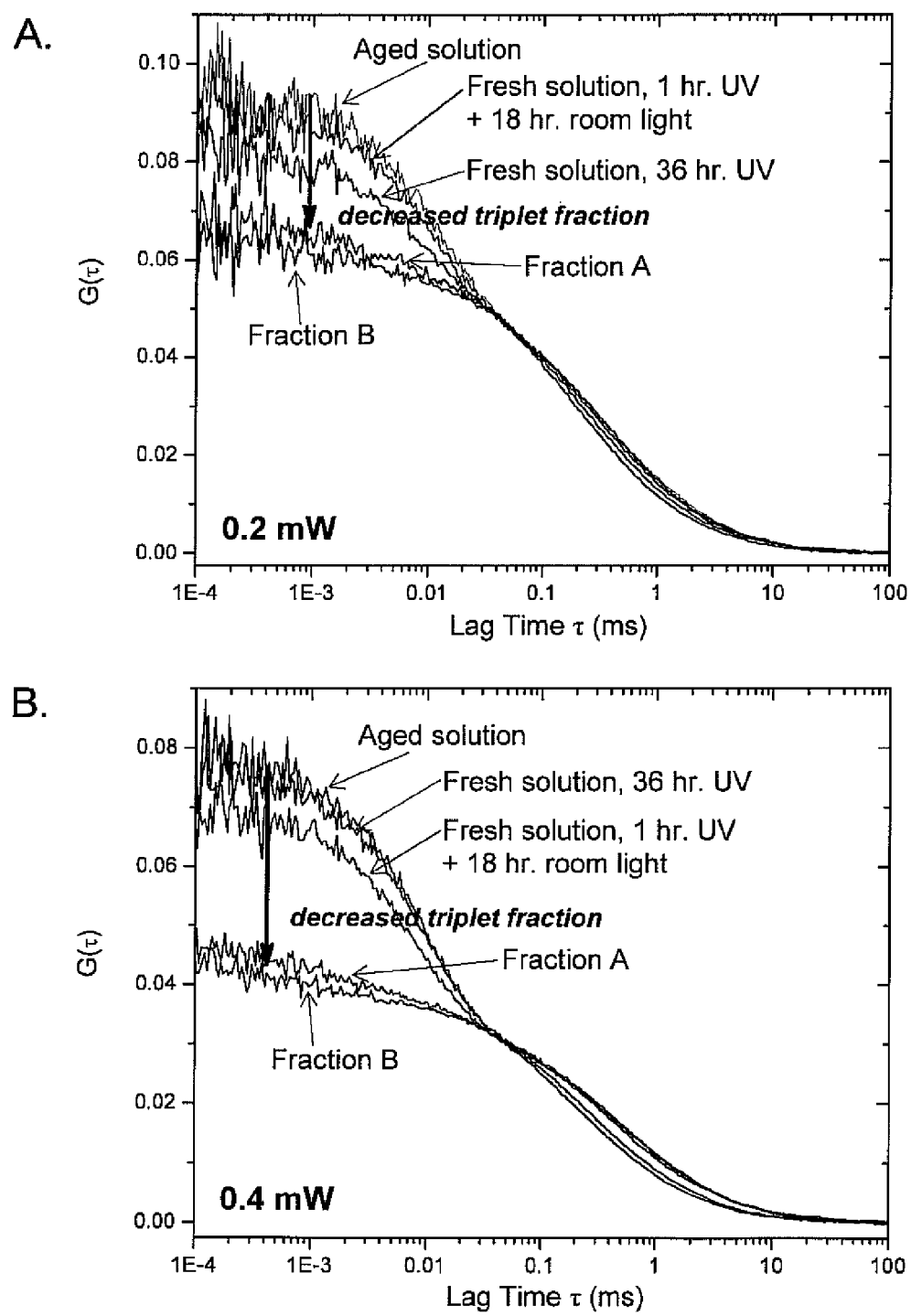
FIG. 11 provides fluorescence correlation spectroscopy (FCS) traces from experiments that measured the quenching activity of 6-hydroxy-2,5,7,8-tetramethylchroman-2-carboxylic acid and various solutions of photomodified 6-hydroxy-2,5,7,8-tetramethylchroman-2-carboxylic acid.

FIG. 11A provides an FCS autocorrelation curve at the 0.2 mW intensity of excitation setting for the aged solution, Fraction A, and Fraction B. At a lag time of 0.001 ms they had autocorrelation amplitudes of ~0.09, ±0.065, and ~0.06, respectively. These data show that both Fraction A and Fraction B had better quenching activity than the aged solution. In addition, the photomodified 6-hydroxy-2,5,7,8-tetramethylchroman-2-carboxylic acid derivative mixtures from the two preparation methods described above were tested in FCS and are included in FIG. 11. Both mixtures displayed triplet quenching activity similar to that observed with the aged solution and worse than that of the purified Fraction A and Fraction B samples, with autocorrelation amplitudes of ~0.08 and ~0.085 at a lag time of 0.001 ms.

The enhanced triplet quenching abilities of the purified Fraction A and Fraction B are even more evident in FIG. 11B, which provides an autocorrelation curve for FCS performed at the 0.4 mW intensity of excitation setting for all five solutions. At a lag time of 0.001 ms, Fraction A and Fraction B had autocorrelation amplitudes of ~0.043 and ~0.04, respectively, while the aged solution and the fresh solution exposed to one hour of UV light followed by 18 hours of room light had autocorrelation amplitudes of ~0.073, and the fresh solution exposed to 36 hours of UV light had an autocorrelation amplitude of ~0.065. These data show that purified Fraction A and purified Fraction B each display better triplet quenching activity under these conditions than freshly prepared photomodified 6-hydroxy-2,5,7,8-tetramethylchroman-2-carboxylic acid solutions or the aged solution of 6-hydroxy-2,5,7,8-tetramethylchroman-2-carboxylic acid.

Example 4

Conversion of Fraction A to Fraction B

Figure 12:
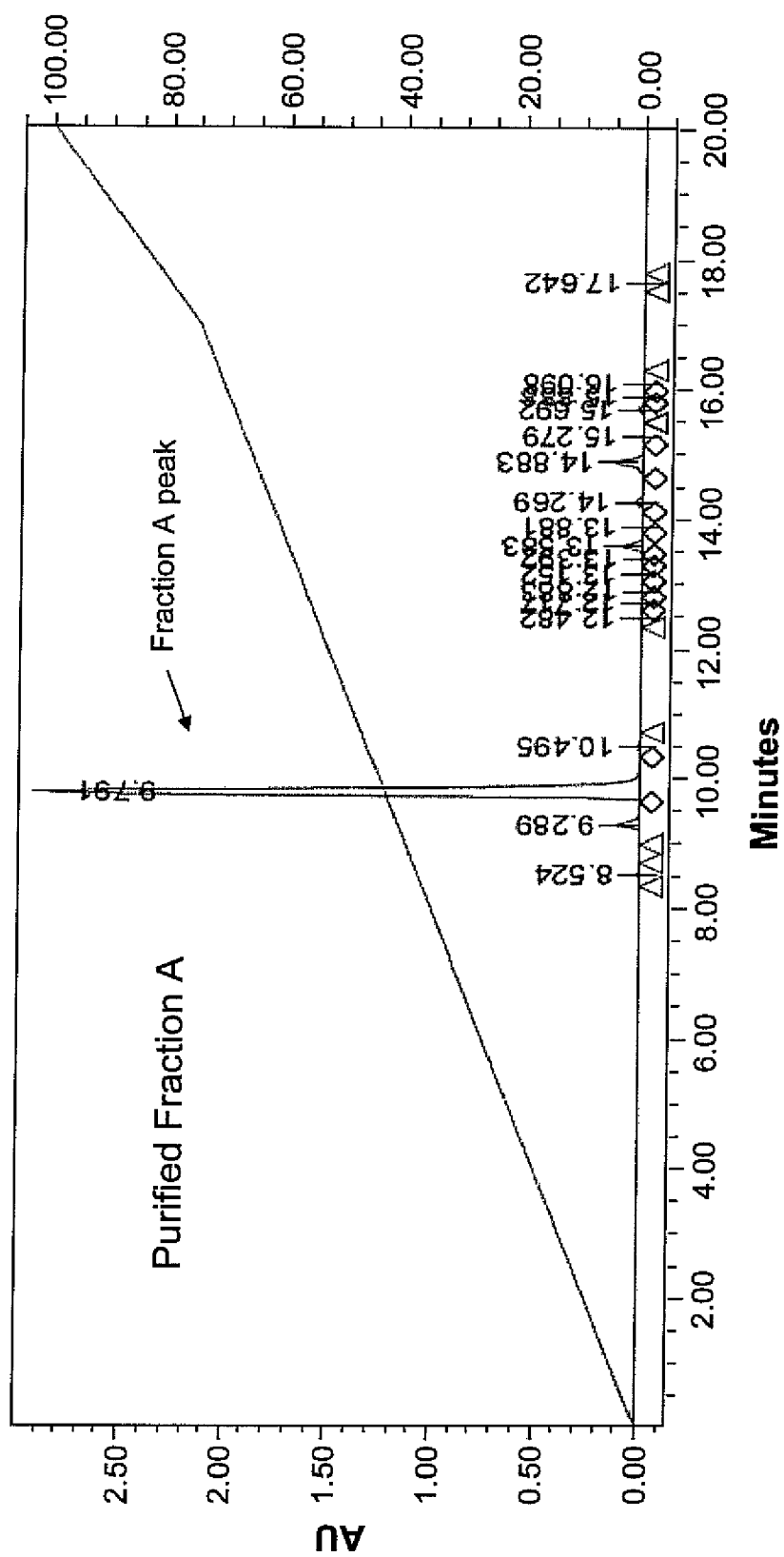
FIG. 12 provides reverse phase HPLC traces showing photolysis of the major component of Fraction A to the major component of Fraction B.

Fraction A was further converted to Fraction B by photolysis in a separate experiment. Specifically, purified Fraction A (reverse phase HPLC peak migration time of 9.791 minutes; FIG. 12A) was subjected to UV irradiation in water for one hour to produce Fraction B (reverse phase HPLC peak migration time of 14.891 minutes; FIG. 12B). The HPLC traces in FIGS. 12A and 12B showed an 80% conversion from Fraction A to Fraction B, with a half-life of 26 minutes, and an apparently very clean conversion. FIG. 12C shows the conversion is essentially complete in about four hours under a portable UV lamp with the major component of Fraction B representing the majority of the resulting mixture with a peak migration time of 14.837.

Example 5

Comparison of Sequencing Readlengths

Experiments were performed to test the performance of pure 6-hydroxy-2,5,7,8-tetramethylchroman-2-carboxylic acid against various mixtures of 6-hydroxy-2,5,7,8-tetramethylchroman-2-carboxylic acid and derivatives thereof. Specifically, the readlengths produced in sequencing-by-incorporation reactions in the presence of 0.5 mM freshly prepared 6-hydroxy-2,5,7,8-tetramethylchroman-2-carboxylic acid (protected from exposure to light, heat, and oxygen; "Fresh") were compared to those produced in the presence of a) 0.5 mM of the mixture produced from the "one hour UV+18 hours room temperature/light" method ("Photomodified mix"); b) 0.5 mM 6-hydroxy-2,5,7,8-tetramethylchroman-2-carboxylic acid and 0.05 mM purified Fraction A ("+0.05 mM FrA"); c) 0.5 mM 6-hydroxy-2,5,7,8-tetramethylchroman-2-carboxylic acid and 0.10 mM purified Fraction A ("+0.10 mM FrA"); and d) 0.5 mM 6-hydroxy-2,5,7,8-tetramethylchroman-2-carboxylic acid and 0.25 mM purified Fraction A ("+0.25 mM FrA").

Figure 13:
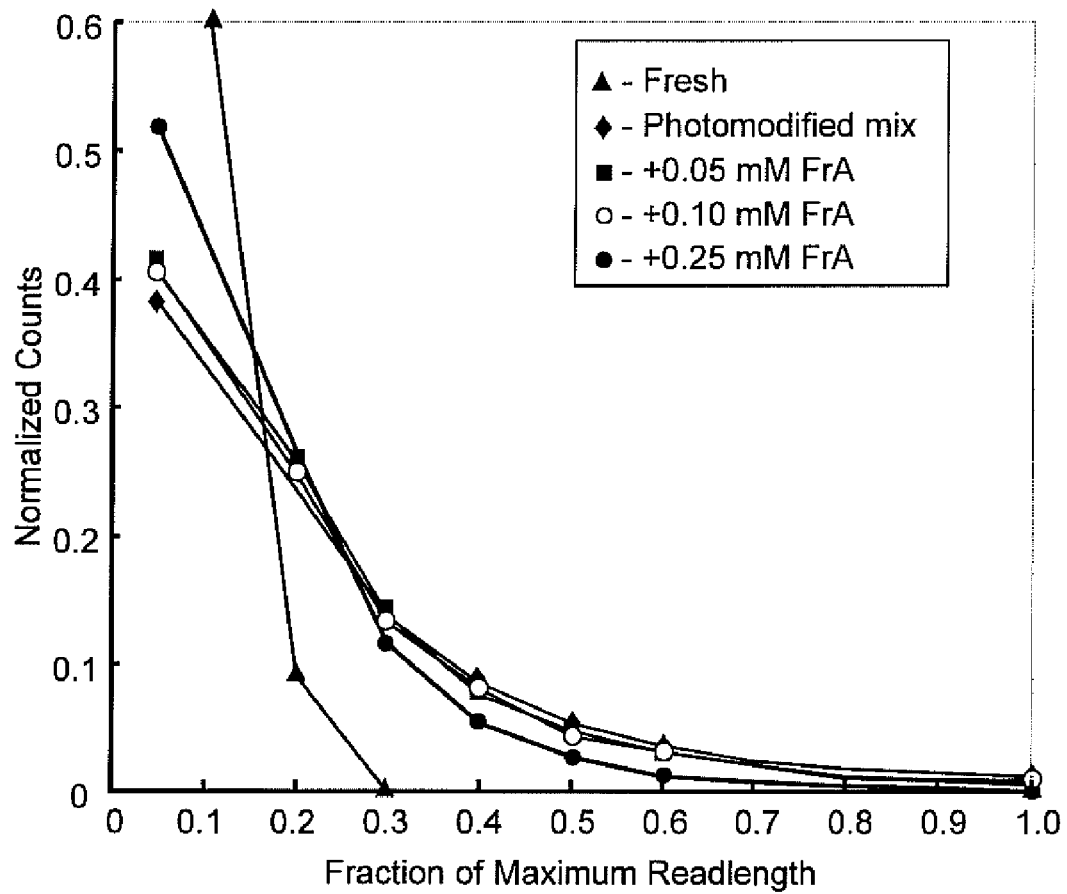
FIG. 13 provides results from an experiment comparing sequencing by incorporation readlengths in the presence of pure 6-hydroxy-2,5,7,8-tetramethylchroman-2-carboxylic acid and various mixtures of 6-hydroxy-2,5,7,8-tetramethylchroman-2-carboxylic acid and derivatives thereof.

FIG. 13 provides a graphical representation of the results from these experiments showing the relationship between the normalized counts versus the fraction of maximum readlength. Each point on each curve indicates a proportion of total sequencing reactions ("Normalized Counts") that achieved or exceeded a given sequencing readlength, where the readlength is measured as a fraction of the maximum readlength attained in any of the reactions. For example, for sequencing reactions performed in the presence of only "fresh" 6-hydroxy-2,5,7,8-tetramethylchroman-2-carboxylic acid (▲), the uppermost point on the graph is located at ~0.6 (y-axis) and ~0.1 (x-axis), indicating that 60% of the sequencing reactions in the presence of that solution attained a readlength of at least one-tenth that of the maximum readlength attained in any of the experiments. This curve further indicates that only about 10% of sequencing reactions attained a readlength of at least one-fifth the maximum, and that very few attained a readlength of at least 30% of the maximum. In contrast, sequencing reactions performed in the presence of the "photomodified mix" of 6-hydroxy-2,5,7,8-tetramethylchroman-2-carboxylic acid and photo-induced derivatives (♦) generally attained much longer readlengths, as did sequencing reactions in the presence of mixtures of 6-hydroxy-2,5,7,8-tetramethylchroman-2-carboxylic acid with (i) 0.05 mM purified Fraction A (■), (ii) 0.10 mM purified Fraction A (○), or (iii) 0.25 mM purified Fraction A (●). (Further HPLC analysis of the phosophomodified mix showed that the ratio of 6-hydroxy-2,5,7,8-tetramethylchroman-2-carboxylic acid to Fraction A in the mix was 10.86:1, which is comparable to the 10:1 ratio in the mixture of 6-hydroxy-2,5,7,8-tetramethylchroman-2-carboxylic acid with 0.05 mM purified Fraction A.) Please note that although the curves in FIG. 13 were generated with data from the experiments described above, the symbols on the curves were added to distinguish between the results for the different experiments, and therefore do not necessarily represent actual data points.

These results clearly showed that sequencing-by-incorporation experiments in the presence of either a mixture of photo-induced 6-hydroxy-2,5,7,8-tetramethylchroman-2-carboxylic acid derivatives or various mixtures of 6-hydroxy- 2,5,7,8-tetramethylchroman-2-carboxylic acid and purified Fraction A generally attained longer readlengths than those performed in the presence of a freshly prepared 6-hydroxy-2,5,7,8-tetramethylchroman-2-carboxylic acid solution. The longer readlengths in these reactions were interpreted as being indicative of a decrease in photo-induced damage to the reaction components, and in particular are believed to be at least partially the result of increased processivity of the polymerase due to reduced photo-induced damage that would otherwise have reduced the activity and/or processivity of the enzyme earlier in the course of the reaction.

Example 6

Identification of Fraction A and Fraction B

Figure 14:
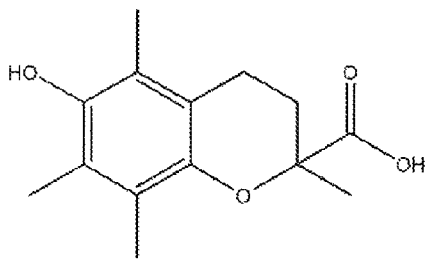
FIG. 14 provides a photodegradation pathway for 6-hydroxy-2,5,7,8-tetramethylchroman-2-carboxylic acid, as described further in Example 6.
Figure 14:
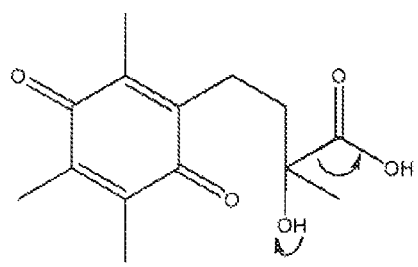
Figure 14:
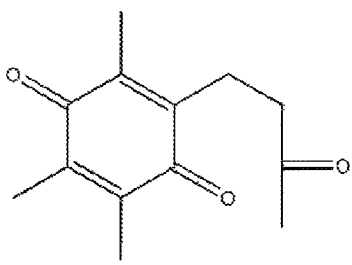

The structures of the major components of Fraction A and Fraction B were identified using $^1$H NMR and LC/MS, which showed the major component of Fraction A is the compound 2-hydroxy-2-methyl-4-(2,4,5-trimethyl-3,6-dioxocyclohexa-1,4-dienyl)butanoic acid, which was previously identified as a derivative of 6-hydroxy-2,5,7,8-tetramethylchroman-2-carboxylic acid (Nonell, et al. (1995) "Solvent influence on the kinetics of the photodynamic degradation of Trolox, a water-soluble model compound for vitamin E,"*Photochem. Photobiol.* 29:157-162). The major component of Fraction B is the decarboxylated product 2,3,5-trimethyl-6-(3-oxobutyl)-1,4-benzoquinone, herein termed "G-Lox." The degradation pathway is shown in FIG. 14. LC/MS was carried out with a Thermo Scientific LCQ Fleet ion trap mass spectrometer. For Fraction A the observed ion mass of 265.05 matches well with the expected M-1 exact mass of 265.11. $^1$H NMR was carried out in deutero chloroform solvent with trimethylsilane as internal reference. The chemical shifts recorded for fraction B (600 MHz, in CDCl$_3$) are 81.99 (s, 31-1). 2.00 (s, 3H), 2.04 (s, 31-1), 2.15 (s, 3H), 2.56 (t, 2H), 2.72 (t, 21-1).

Example 7

Methods of Preparation

As noted above, one method for preparing mixtures comprising certain quinone derivatives of the invention was by subjecting 6-hydroxy-2,5,7,8-tetramethylchroman-2-carboxylic acid to photodegradation by exposure to oxygen and irradiation under UV light (e.g., lamp) for one hour, followed by exposure to ambient light at room temperature for 18 hours to produce a mixture comprising quinone derivatives of the invention, including compounds of formula I such as 2-hydroxy-2-methyl-4-(2,4,5-trimethyl-3,6-dioxocyclohexa-1,4-dienyl)butanoic acid and 2,3,5-trimethyl-6-(3-oxobutyl)-1,4-benzoquinone. An alternative method used for preparing mixtures comprising certain quinone derivatives was to subject 6-hydroxy-2,5,7,8-tetramethylchroman-2-carboxylic acid to 36 hours of UV irradiation in the presence of oxygen. The product of both 6-hydroxy-2,5,7,8-tetramethylchroman-2-carboxylic acid photomodification methods is a mixture comprising, e.g., 2-hydroxy-2-methyl-4-(2,4,5-trimethyl-3,6-dioxocyclohexa-1,4-dienyl)butanoic acid and 2,3,5-trimethyl-6-(3-oxobutyl)-1,4-benzoquinone. These mixtures were optionally subjected to a 130 minute UV irradiation to convert all remaining 2-hydroxy-2-methyl-4-(2,4,5-trimethyl-3,6-dioxocyclohexa-1,4-dienyebutanoic acid into 2,3,5-trimethyl-6-(3-oxobutyl)-1,4-benzoquinone, as described above. As such, 2,3,5-trimethyl-6-(3-oxobutyl)-1,4-benzoquinone may also be prepared directly from 2-hydroxy-2-methyl-4-(2,4,5-trimethyl-3,6-dioxocyclohexa-1,4-dienyl)butanoic acid, as UV exposure in the presence of oxygen converts 2-hydroxy-2-methyl-4-(2,4,5-trimethyl-3,6-dioxocyclohexa-1,4-dienyl)butanoic acid into 2,3,5-trimethyl-6-(3-oxobutyl)-1,4-benzoquinone.

Figure 15:
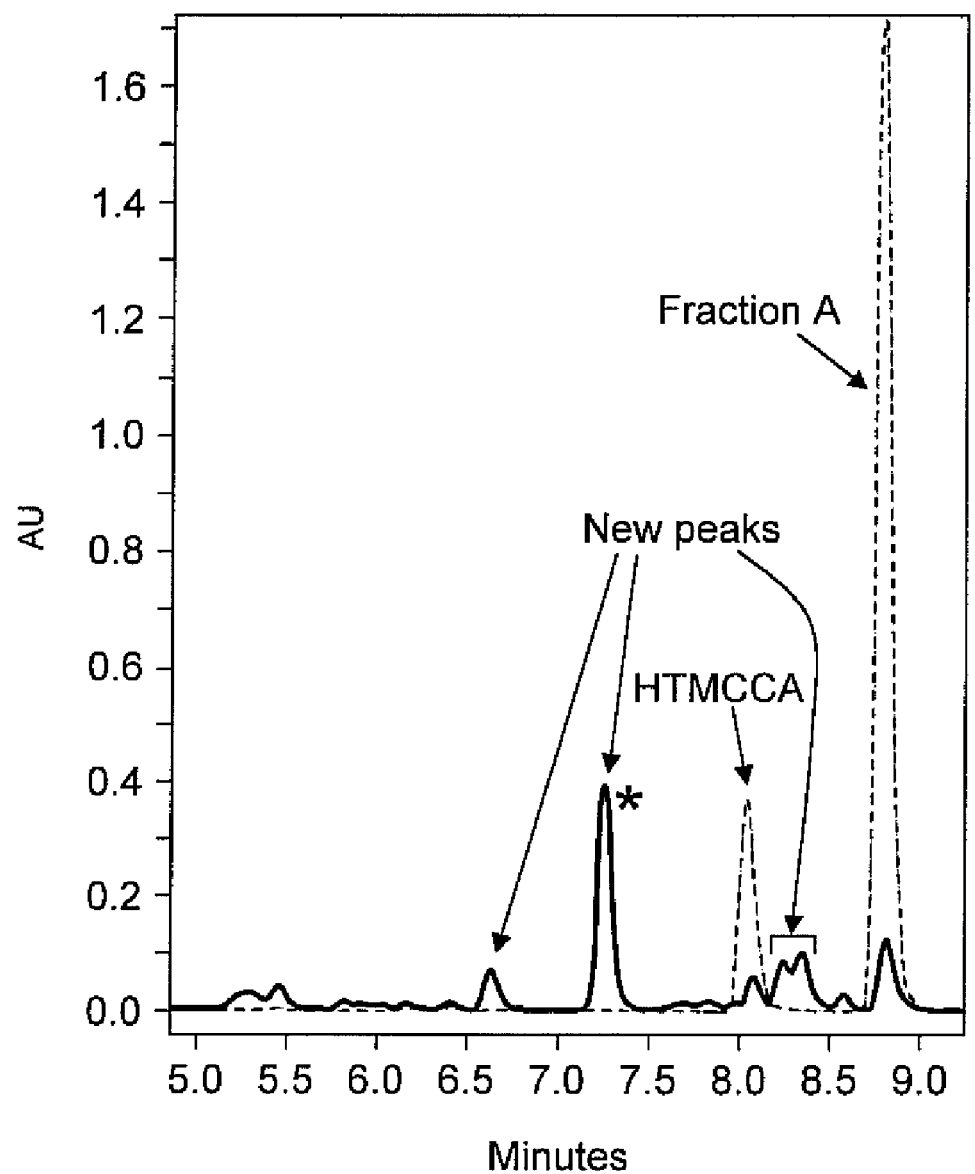
FIG. 15 provides a trace from a reverse phase HPLC performed on a mixture comprising photo-induced damage mitigating agents prepared by a method of the invention.

A further alternative method used for preparing a mixture comprising quinone derivatives of the invention was to expose 6-hydroxy-2,5,7,8-tetramethylchroman-2-carboxylic acid to a highly basic solution prior to UV irradiation. In one such experiment, 0.2503 grams of pure 6-hydroxy-2,5,7,8-tetramethylchroman-2-carboxylic acid was added to 1.08 mL methanol, shaken to form a homogeneous solution, and subsequently diluted with 6.0 mL water. The dilution was followed by addition of 1 mL of a KOH solution, and mixing by vortex until a transparent solution was formed. Droplets of 1M KOH were further added until the solution reached pH 12, at which time water was added to bring the total volume to 10.00 mL and the final concentration of 6-hydroxy-2,5,7,8-tetramethylchroman-2-carboxylic acid to 100 mM. The resulting solution was UV irradiated for one hour and subsequently exposed to ambient light at room temperature for 18 hours. Reverse phase HPLC was performed on a mixture prepared by this method, and the new species produced are shown in FIG. 15. The dashed trace shows the HPLC peaks from a mixture of quinone derivatives prepared from a solution of 6-hydroxy-2,5,7,8-tetramethylchroman-2-carboxylic acid under neutral pH (7.5), and this mixture comprises both 6-hydroxy-2,5,7,8-tetramethylchroman-2-carboxylic acid (at ~8.1 minutes) and Fraction A (at ~8.6 minutes). The solid trace shows the peaks in a mixture produced by increasing the pH of a solution of 6-hydroxy-2,5,7,8-tetramethylchroman-2-carboxylic acid prior to UV irradiation, as described above. The peaks for both 6-hydroxy-2,5,7,8-tetramethylchroman-2-carboxylic acid and Fraction A were dramatically reduced, and new peaks were observed, e.g., at ~6.6, ~7.3, and ~8.2-8.4 minutes. The peak indicated with an asterisk is a compound of the formula III or IV or a racemic mixture thereof. Further, the rightmost peak of the two bracketed peaks has been identified as a compound of formula V or VI or a racemic mixture thereof. The resulting mixture increased sequencing readlengths to a greater extent than did a mixture prepared at pH 7.5 (data not shown).

Although pH 12 was used in the preparation described above, the basic pH may be altered somewhat, although it was found that pH over 13 decreased the production of certain desirable fractions. For example, a 100 mM solution of 6-hydroxy-2,5,7,8-tetramethylchroman-2-carboxylic acid was prepared as described above except that it was titrated to pH 11.5 and exposed to ambient light at room temperature for 16 hours (no UV irradiation). The resulting mixture was produced the HPLC trace shown in FIG. 16, which is similar to the HPLC provide shown in FIG. 15. Major fractions are indicated by numbers 1-8, where fraction 6 is pure 6-hydroxy-2,5,7,8-tetramethylchroman-2-carboxylic acid and fraction 8 corresponds to previously identified Fraction A. Peaks 2-8 were isolated by HPLC, and Table 1 provides certain characteristics of the purified fractions.

TABLE 1

| Fraction | Retention time (min) | UV wavelength$_{MA}$ | Mass (amu) |
| --- | --- | --- | --- |
| 2 | 5.3/5.4 | 241 | 300 |
| 3 | 6.2 | 241 | 282 |
| 4 | 6.6 | 241 | 282 |
| 5 | 7.2 | 258 | 282 |
| 6 | 8.0 | 288 | 250 |

TABLE 1-continued

| Fraction | Retention time (min) | UV wavelength$_{MA}$ | Mass (amu) |
|---|---|---|---|
| 7 | 8.3 | 256 | 282 |
| 8 | 8.9 | 265 | 266 |

Purified fractions 5 and 7 were tested in sequencing readlength experiments as described above and both were found to significantly increase sequencing readlength indicating that they comprise photo-induced damage mitigating agents. Further, both purified fractions were also found to increase the brightness of Alexa A-647 dye, further demonstrating efficient triplet state quenching activity.

The type of UV and/or light exposure can also be modified. In one preferred method of preparing a photo-induced damage mitigating agent, 6-hydroxy-2,5,7,8-tetramethylchroman-2-carboxylic acid was dissolved in methanol and water was added to bring the volume up to 95% of the final total volume. The pH was raised to 11.5-12.0 by addition of potassium hydroxide. Once a pH of 11.5-12.0 was reached, the volume was increased to the final total volume, which produced a 100 mM final concentration of 6-hydroxy-2,5,7,8-tetramethylchroman-2-carboxylic acid in 10% methanol. The solution was incubated in the dark at 18° C.-22° C. for 72 hours. (Incubation with light was found to speed up the process, but was less controllable.) Subsequently, the pH was adjusted downward to pH 7.5 to stabilize the components of the resulting mixture. The preparation was filtered to remove particulates using a 0.2 μm filter prior to use. This method produced consistently effective photo-induced damage mitigating agents and admixtures thereof, the admixtures generally comprising 10-15% of fraction 5, 5-10% of fraction 7, 10-20% of fraction 4, 0-10% of fraction 8, and 0-10% of fraction 6. These percentages are all relative to the initial total concentration of 6-hydroxy-2,5,7,8-tetramethylchroman-2-carboxylic acid (100 mM).

Figure 17:
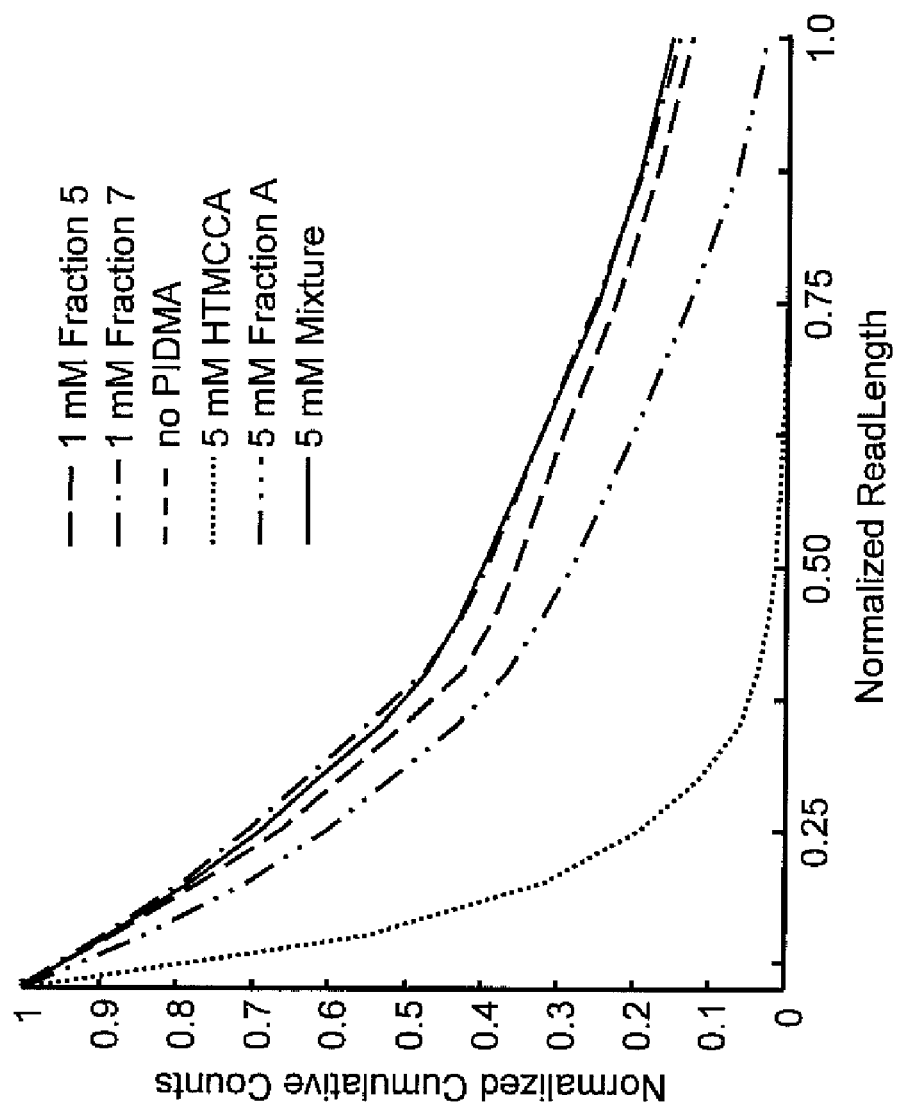
FIG. 17 provides data showing enzyme processivity in the presence of certain quinone derivatives of the invention.

FIG. 17 provides a graphical representation of the results from single-molecule, real-time sequencing reactions in the presence of purified fraction 5, purified fraction 7, no photo-induced damage mitigating agents ("no PIDMA"). 6-hydroxy-2,5,7,8-tetramethylchroman-2-carboxylic acid (HT-MCCA), Fraction A, and a mixture prepared by the method described in the previous paragraph (Mixture). This graph shows the relationship between the normalized counts versus the fraction of maximum readlength. Each point on each curve indicates a proportion of total sequencing reactions ("Normalized Counts") that achieved or exceeded a given sequencing readlength, where the readlength is measured as a fraction of the maximum readlength attained in any of the reactions. These data show that longer readlengths are produced in sequencing-by-incorporation reactions in the presence of purified fraction 5, purified fraction 7, a mixture of PIDMA prepared as described herein, and, to a lesser extent, Fraction A that readlengths produced in the presence of the photo-induced damage mitigating agent, 6-hydroxy-2,5,7,8-tetramethylchroman-2-carboxylic acid, which is surprisingly similar to having no PIDMA present at all. The longer readlengths in these reactions are interpreted as being indicative of a decrease in photo-induced damage to the reaction components, and in particular are believed to be at least partially the result of increased processivity of the polymerase due to reduced photo-induced damage that would otherwise have reduced the activity and/or processivity of the enzyme earlier in the course of the reaction.

Figure 9:
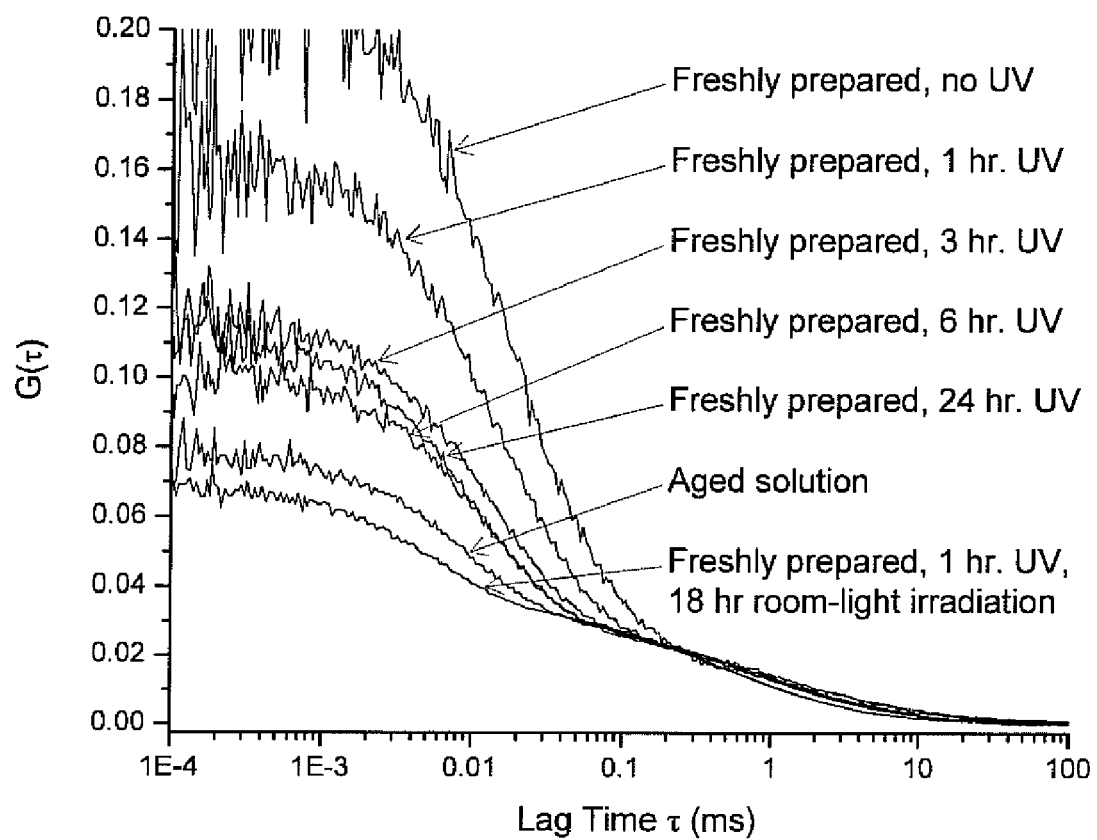
FIG. 9 provides fluorescence correlation spectroscopy (FCS) traces from experiments that measured the quenching activity of 6-hydroxy-2,5,7,8-tetramethylchroman-2-carboxylic acid and derivatives thereof.

Of course, the amount of time for UV irradiation and room light exposure can be adjusted, as can the concentration of the 6-hydroxy-2,5,7,8-tetramethylchroman-2-carboxylic acid solution to be treated. For example, one to twenty-four hours of UV irradiation have been employed, as have 18 to 36 hours room light exposure. In general, and as shown in FIG. 9 described above, increasing UV exposures increase the ability of the mixture to effectively mitigate photo-induced damage, although there was no significant difference between the three, six, and 24 hour exposures (FIG. 9). Further, the solutions of 6-hydroxy-2,5,7,8-tetramethylchroman-2-carboxylic acid subjected to photomodification were typically of a concentration of 95-100 mM, which is near the saturation point for the compound. However, treatment of more or less concentrated solutions in contemplated and known chemical methods may be employed to increase the solubility of the compound prior to treatment.

It is to be understood that this method of preparation of certain compounds of the inventions is exemplary and other methods for preparing this compound may be performed using chemistry methods well known to those of skill in the art, including direct synthesis methods, for example, starting with a quinone such as 1,4-benzoquinone or 1,4-hydroquinone.

Figure 18:
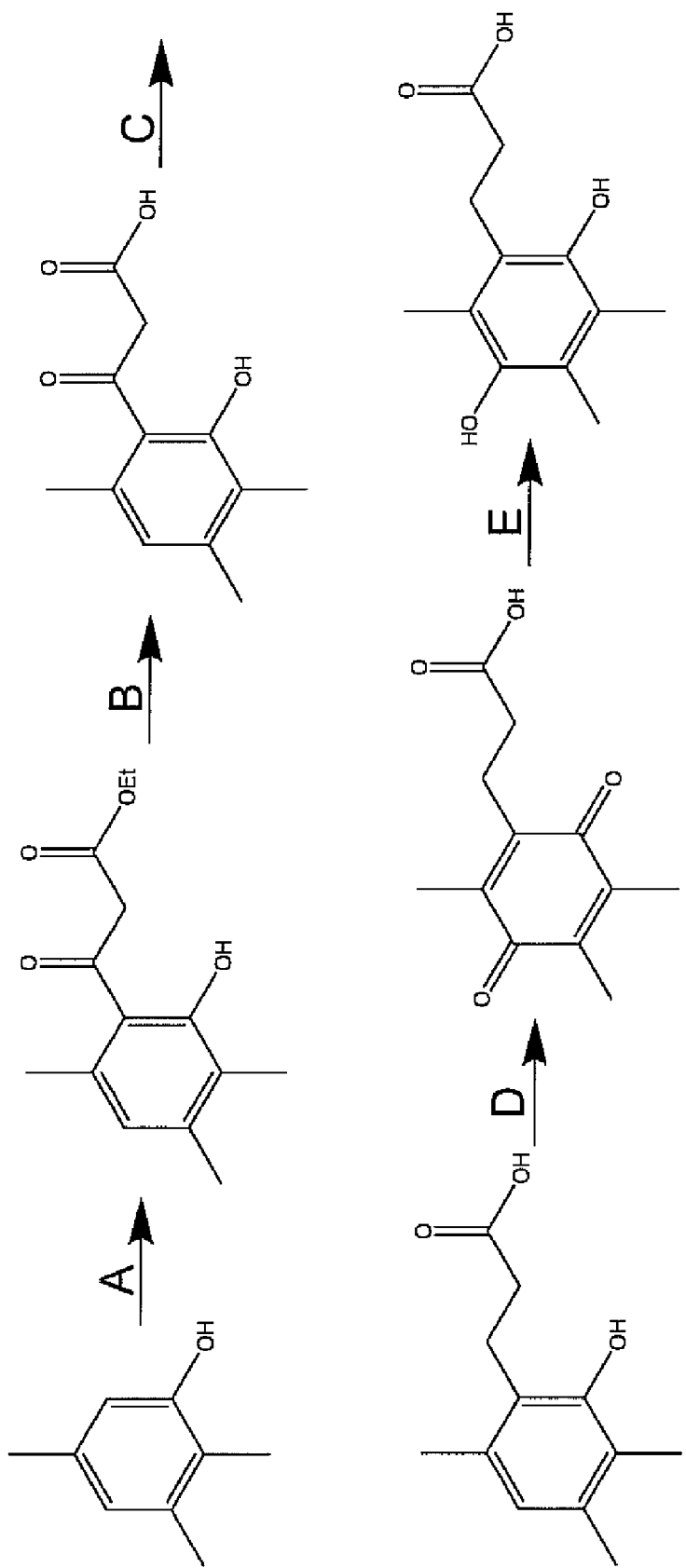
FIG. 18 provides a synthesis method for one of the compounds of formula II, as further described in Example 7.

One method for preparing a compound of formula H is shown in FIG. 18. As per FIG. 18, Friedel-Crafts acylation uses ethyl malonyl chloride as the agent and aluminum chloride ($AlCl_3$) as a catalyst to add the ethyl malonyl group to 2,3,5-trimethylphenol at step A, which is then hydrolyzed to the corresponding acid at step B. Reduction of the carbonyl group is achieved using either Wolff-Kishner reduction or Clemmensen reduction reaction at step C. Oxidation of the hydroxybenzylacid compound with potassium nitrosodisulfonate at step D gives the corresponding 1,4-benzoquinone acid, which is then reduced to the 1,4-hydroquinone acid with sodium hydrosulfite at step E.

Figure 19:
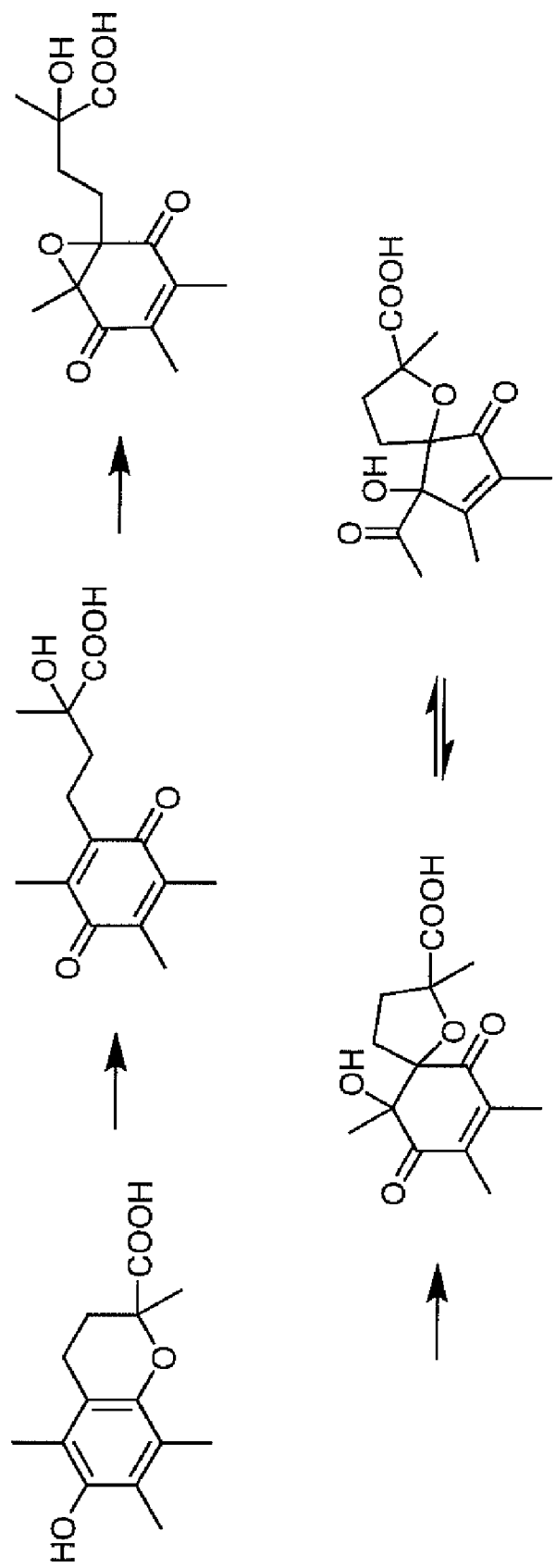
FIG. 19 provides a simplified scheme for the production of certain compounds of the invention.

In conclusion, derivatives of 6-hydroxy-2,5,7,8-tetramethylchroman-2-carboxylic acid and combinations thereof were found to be more potent fluorescent dye triplet-state and/or free radical quenchers than freshly prepared 6-hydroxy-2,5,7,8-tetramethylchroman-2-carboxylic acid alone. This more effective quenching slows the accumulation of the damaging triplet state of the fluorescent dyes, and thereby greatly improves the photophysical properties of the fluorescent dyes in an illuminated reaction allowing, e.g., allowing dramatically longer read lengths (e.g. from 50 to greater than 400 bases) in illuminated sequencing reactions. Further, it was found that mixtures of compounds of formula II with either 6-hydroxy-2,5,7,8-tetramethylchroman-2-carboxylic acid or compounds of formula I mitigate photo-induced damage far more effectively than freshly prepared 6-hydroxy-2,5,7,8-tetramethylchroman-2-carboxylic acid solutions, providing new and better methods for preventing and/or slowing the accumulation of photo-induced damaged components in reaction mixes. FIG. 19 provides a simplified scheme for the production of certain compounds of the invention from 6-hydroxy-2,5,7,8-tetramethylchroman-2-carboxylic acid solution. It is to be understood that this scheme for preparation of certain compounds of the inventions is exemplary and other methods for preparing this compound may be performed using chemistry methods well known to those of skill in the art.

Example 8

Crystal Structure Determination

Figure 6:
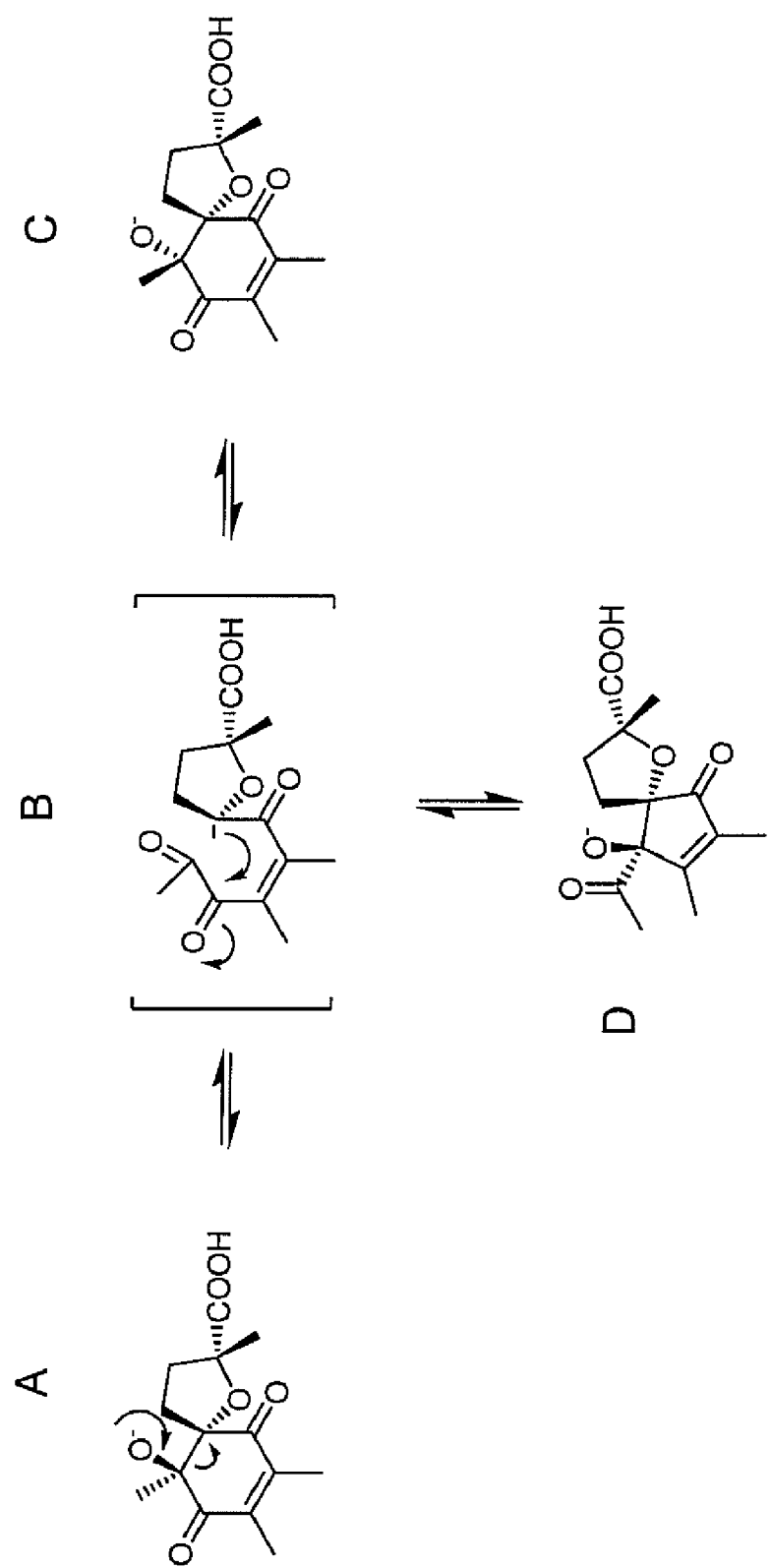
FIG. 6 provides a scheme showing the interconversion of certain photo-induced damage mitigating agents of the invention.
Figure 16:
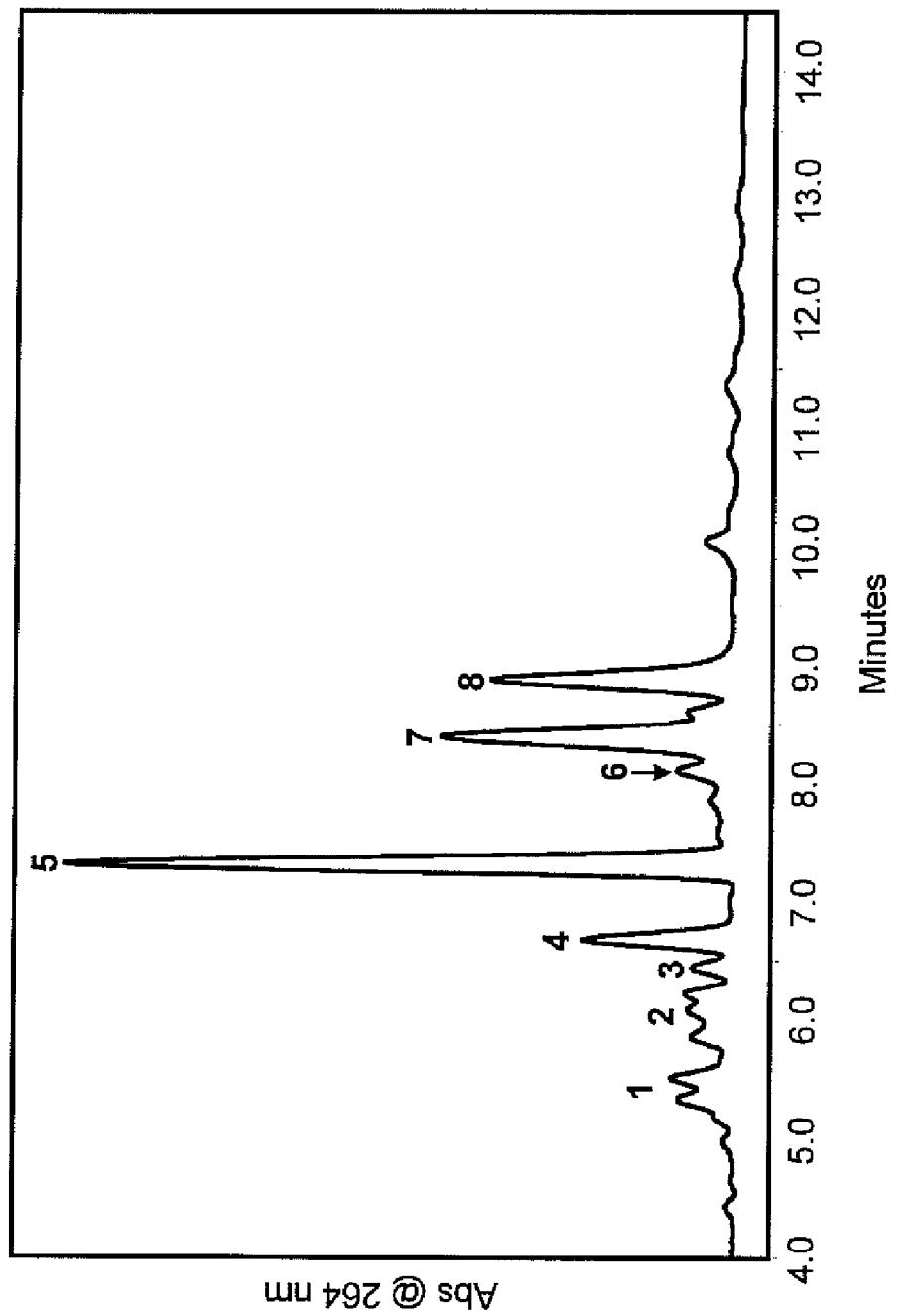
FIG. 16 provides a trace from a reverse phase HPLC performed on a mixture comprising photo-induced damage mitigating agents prepared by a method of the invention.
Figure 20:
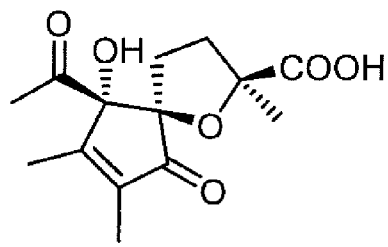
FIG. 20 provides illustrative examples of stereoisomers of certain compounds of formula IV (A, B) and formula III (C—F).
Figure 20:
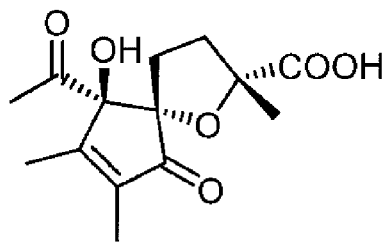
Figure 20:
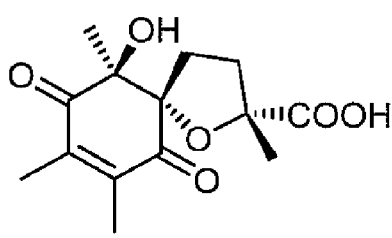
Figure 20:
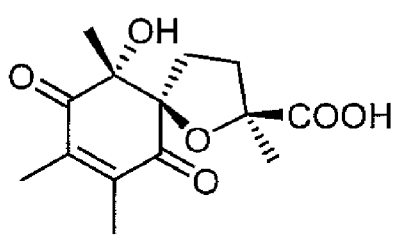
Figure 20:
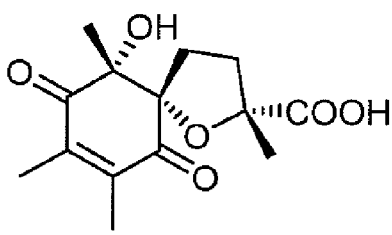
Figure 20:
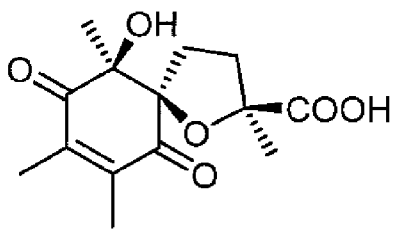

Fractions 4, 5, and 7 in FIG. 16 were purified by HPLC and concentrated to produce crystals. The crystal structure of these purified fractions was determined by X-ray crystallography and the stereoisomers so determined are provided in FIG. 20. Fraction 4 was determined to comprise a racemic mixture of compounds of formulas A and B. Fraction 5 was determined to comprise a racemic mixture of compounds of formulas C and D. Fraction 7 was determined to comprise a racemic mixture of compounds of formulas E and F. As will be clear to one of ordinary skill in the art, formulas C and D are diastereomers of formulas E and F, respectively. Without being bound to a particular theory or mechanism of operation, it is believed that both fraction 5 and fraction 7 are formed when fraction 4 is subjected to the base (low pH) treatment used in the preparation of certain mixtures and admixtures of the invention. This transformation is shown in FIG. 6. Under basic conditions, a five-carbon ring in the composition of fraction 4 interconverts with the six-carbon ring of the compositions of fractions 5 and 7, thereby creating an equilibrium of the three isomers. The structures are stabilized by decreasing the pH, which inhibits the transformations between the three isomers and thereby stabilizes the amounts of the structures in an admixture useful for mitigation of photo-induced damage.

Figure 27:
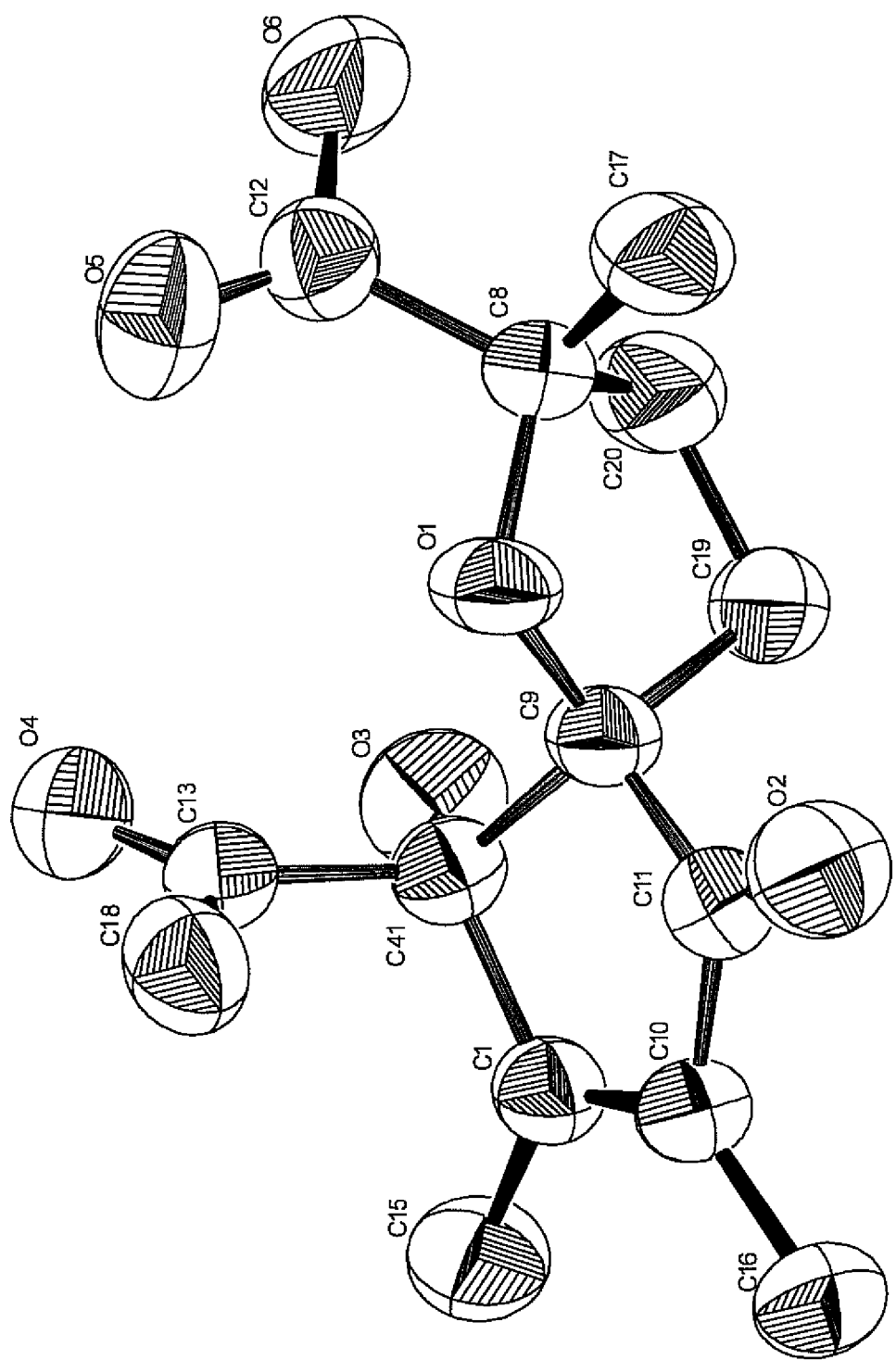
FIG. 27 provides a crystal structure for a preferred embodiment of a compound of formula IV that corresponds to fraction 4 described in Example 7.
Figure 28:
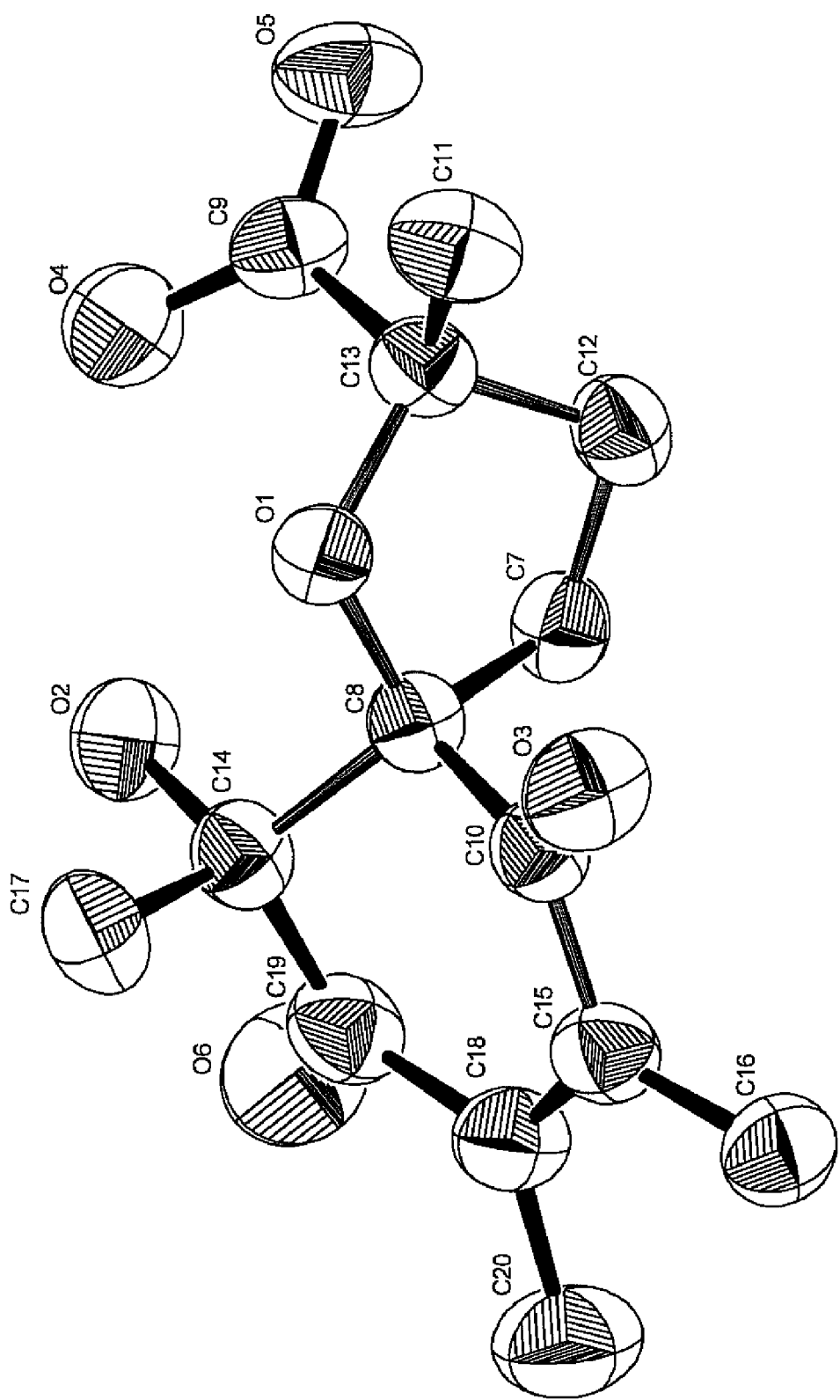
FIG. 28 provides a crystal structure for a preferred embodiment of a compound of formula III that corresponds to fraction 5 described in Example 7.
Figure 29:
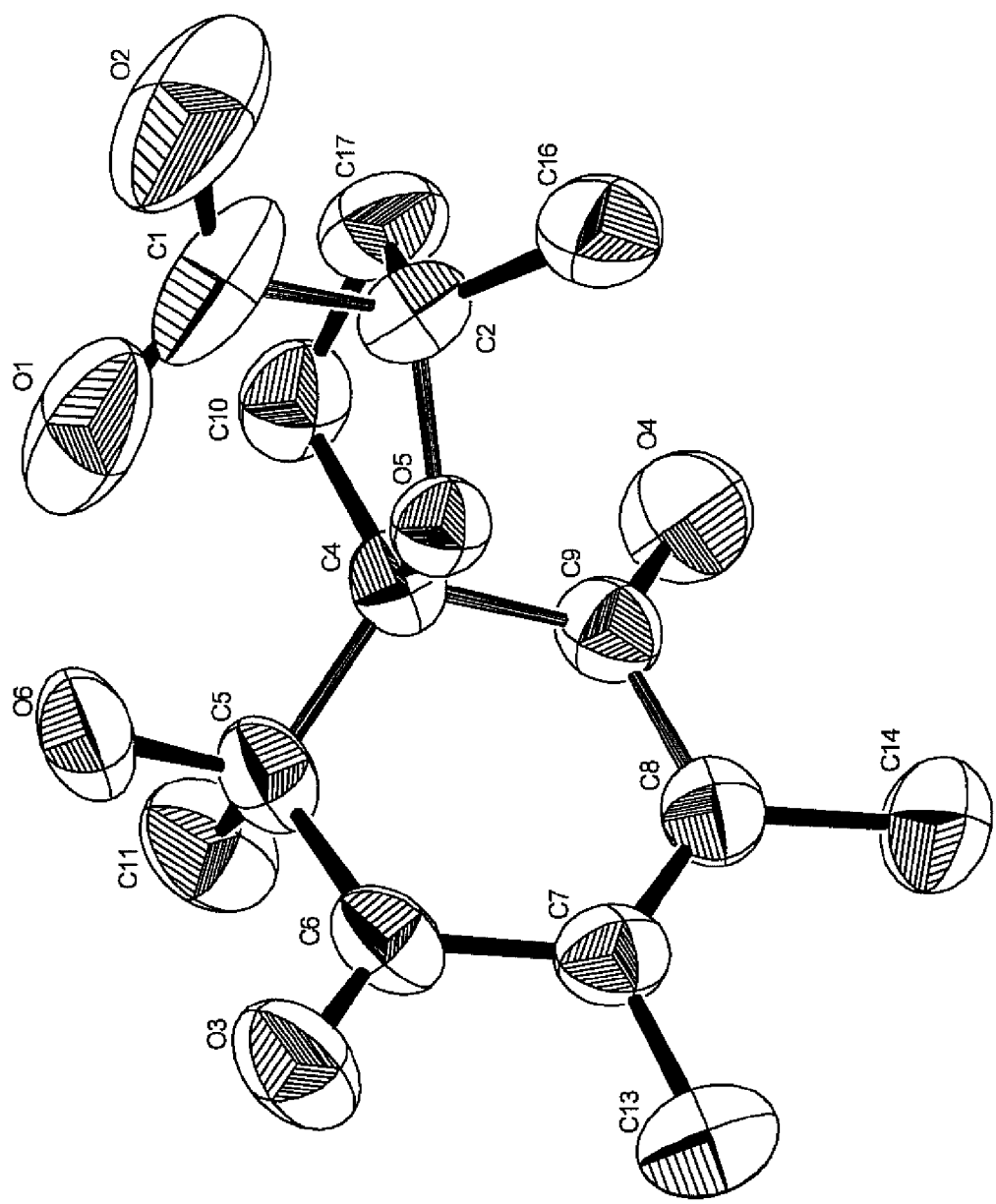
FIG. 29 provides a crystal structure for a preferred embodiment of a compound of formula III that corresponds to fraction 7 described in Example 7.

FIG. 27 provides a three-dimensional crystal structure of a compound of fraction 4; FIG. 28 provides a three-dimensional crystal structure of a compound of fraction 5; and FIG. 29 provides a three-dimensional crystal structure of a compound of fraction 7. Crystals and crystal structures for the compounds of fractions 4, 5, and 7 were performed in a substantially similar way. As an example, the data collection description for a crystal of fraction 4 is as follows: A colorless prism crystal of $C_{14}H_{18}O_6$ having approximate dimensions of 0.20×0.20×0.20 mm was mounted on a glass fiber. All measurements were made on a Rigaku RAXIS RAPID imaging plate area detector with graphite monochromated Cu-Kα radiation. Indexing was performed from 6 oscillations that were exposed for 120 seconds. The crystal-to-detector distance was 127.40 mm. Cell constants and an orientation matrix for data collection corresponded to a primitive monoclinic cell with dimensions:

a=8.52248(15) Å
b=11.7410(2) Å β=104.9429(7)°
c=14.7214(3) Å
V=1423.24(4) Å$^3$

For Z=4 and F.W.=282.29, the calculated density is 1.317 g/cm$^3$. The systematic absences of h01: 1±2n
0k0: k±2n uniquely determine the space group to be: P2$_1$/c (#14).

The data were collected at a temperature of 20±1° C. to a maximum 2θ value of 136.4°. A total of 108 oscillation images were collected. A sweep of data was done using ω scans from 20.0 to 200.0° in 5.0° step, at χ=0.0° and φ=0.0°. The exposure rate was 24.0 [sec./°]. A second sweep was performed using ω scans from 20.0 to 200.0° in 5.0° step, at χ=54.0° and φ=120.0°. The exposure rate was 24.0 [sec./°]. Another sweep was performed using ω scans from 20.0 to 200.0° in 5.0° step, at χ=54.0° and φ=240.0°. The exposure rate was 24.0 [sec./°]. The crystal-to-detector distance was 127.40 mm. Readout was performed in the 0.100 mm pixel mode.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. For example, benzoquinone derivatives may be converted to hydroquinone derivatives by reducing agents (e.g., DTT) present in a reaction mixture. To the extent not already expressly incorporated herein, all published references and patent documents referred to in this disclosure are incorporated herein by reference in their entirety for all purposes.

What is claimed is:

1. A composition comprising:
   a first reactant:
   a second reactant; and
   a photo-induced damage mitigating agent admixture comprising a compound of formula:

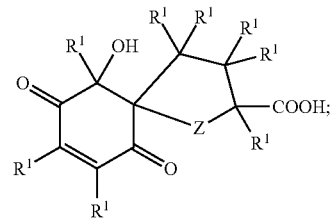

wherein $R^1$ is independently selected from the group consisting of hydrogen, halogen, alkyl, —$CH_3$, —$(CH_2)_n R^2$, —$(CH_2)_n R^2 R^3$, —$SO_3H$, —$NO^2$, —$OR^2$, —$COR^2$, —$COOR^2$, —$(CH_2)_n OR^2$, —$CH(OH)R^2$, —$S(O)_m R^2$, —$SO_3 R^2$, —$CONH_m (R^2)_{2-m}$, —$SO_2 NH_m (R^2)^{2-m}$, $NH_m (R^2)_{2-m}$, —$CONHSO_3 H$, —$(CH_2)_n R^5$, —$CH(OR^2)R^3$, —$(CH_2)_n R^2 R^5$, —$R^5$, —$OR^5$, —$COR^5$, —$COOR^5$, —$(CH_2)_n OR^5$, where m is an integer and where n is an integer from 1 to 4;

$R^2$ is selected from the group consisting of hydrogen, halogen, alkyl, —$CH_3$, hydroxyl, —$SO_3H$, —$NO_2$, —$OR^3$, —$COR^3$, —$COOR^3$, —$CH(OR^3)R^4$, —$CH(OH)R^3$, —$SO_3 R^3$, —$R^5$, —$OR^3 R^5$, —$COR^5$, —$COR^3 R^5$, —$COR^3 R^4 R^5$, —$CH(OH)R^5$, —$S(O)_m R^3$, —$SO_3 R^3$, —$CONH_m (R^3)_{2-m}$, $NH_m (R^3)$ —$CONHSO_3 H$, —$SO_2 NH_m (R^3)^{2-m}$, where m is an integer;

$R^3$ and $R^4$ are independently selected from the group consisting of hydrogen, halogen, hydroxyl, alkyl, —$CH_3$, —$SO_2 H$, $NO_2$, and —COOH;

$R^5$ is a linker, and Z is a bridging group;

and further wherein interaction of the first reactant with the second reactant under excitation illumination causes photo-induced damage to the first reactant in the absence of the photo-induced damage mitigating agent admixture.

2. The composition of claim 1, wherein the first reactant is confined.

3. The composition of claim 2, wherein the first reactant is immobilized on a surface comprising an optical confinement.

4. The composition of claim 3, wherein the optical confinement comprises a zero mode waveguide.

5. The composition of claim 1, wherein the first reactant is an enzyme.

6. The composition of claim 1, wherein the first reactant is a polymerase.

7. The composition of claim 1, wherein the photo-induced damage mitigating agent admixture further comprises another compound of a formula selected from the group consisting of

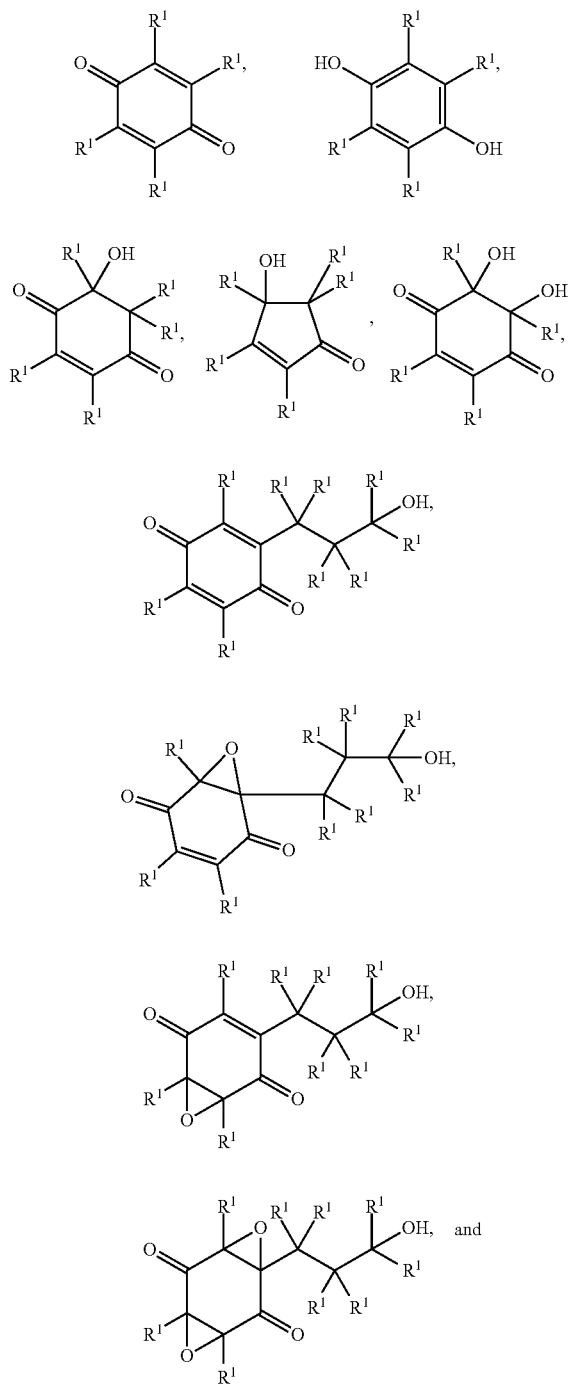

8. The composition of claim 7, wherein the photo-induced damage mitigating agent admixture comprises a compound of the formula

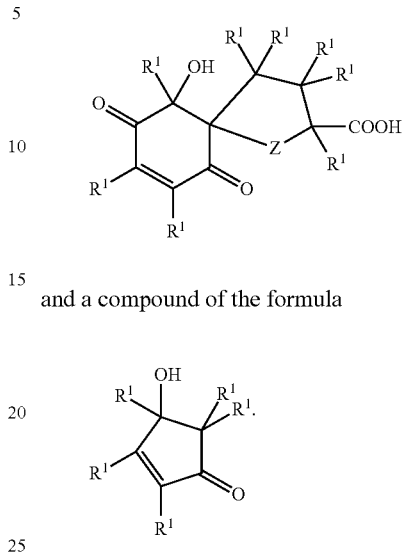

and a compound of the formula

9. The composition of claim 7, wherein the photo-induced damage mitigating agent admixture comprises multiple racemates and/or diastereomers of the formula

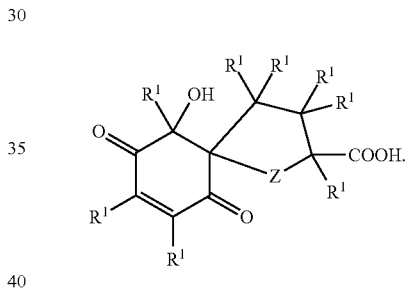

10. The composition of claim 7, wherein the photo-induced damage mitigating agent admixture further comprises at least 10% of a compound of the formula

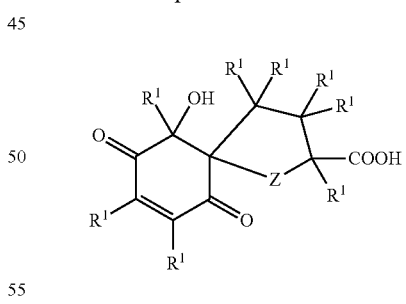

and no more than 50% of a compound of formula

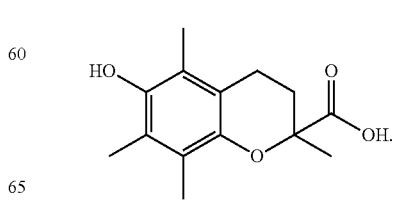

11. The composition of claim 1, wherein the second reactant comprises a fluorescent or fluorogenic molecule.

12. A method of performing an illuminated reaction, comprising:

providing a substrate having a reaction mixture disposed thereon, wherein the reaction mixture comprises the composition of claims 1, wherein the photo-induced damage mitigating agent admixture reduces an amount of photo-induced damage to the first reactant resulting from interaction of the first reactant with the second reactant under excitation illumination to an amount that is less than that which would occur in the absence of the photo-induced damage mitigating agent admixture; and illuminating the reaction mixture on the substrate with an excitation illumination.

13. The method of claim 12, further comprising the step of monitoring a reaction between the first and second reactant while illuminating the reaction mixture.

14. The method of claim 12, wherein said illuminated reaction is a base extension reaction.

15. The method of claim 12, wherein said first reactant is a polymerase enzyme.

16. The method of claim 12, wherein said second reactant comprises fluorescent or fluorogenic molecule.

17. The method of claim 12, wherein the photo-induced damage mitigating agent admixture further comprises another compound of a formula selected from the group consisting of

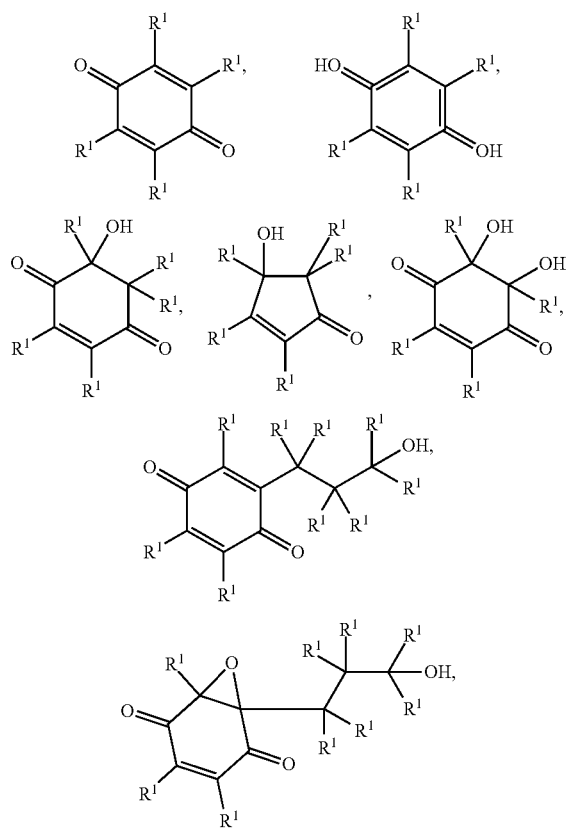

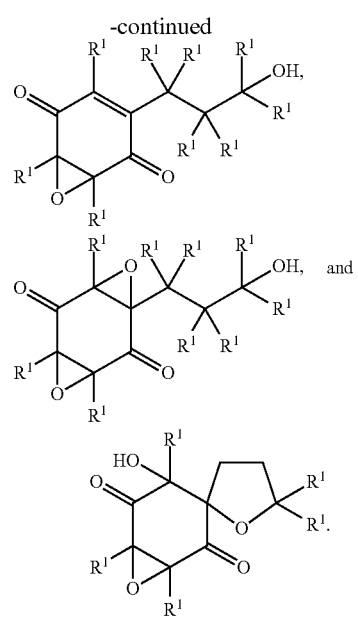

18. The method of claim 17, wherein the photo-induced damage mitigating agent admixture comprises both a compound of the formula

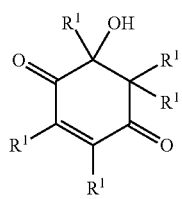

and a compound of the formula

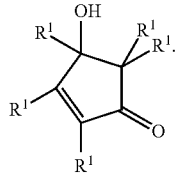

19. The method of claim 18, wherein the photo-induced damage mitigating agent admixture comprises multiple racemates and/or diastereomers of the formula

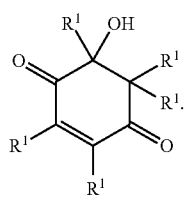

20. A device comprising:
a substrate having an observation region;
a first reactant immobilized within the observation region;
a second reactant disposed within the observation region, wherein interaction between the first and second reactants under excitation illumination causes photo-induced damage to the first reactant; and at least one photo-induced damage mitigating agent admixture comprising a compound of formula

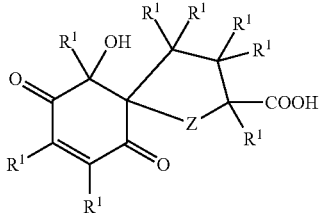

disposed within the observation region, wherein $R^1$ is independently selected from the group consisting of hydrogen, halogen, alkyl, —$CH_3$, —$(CH_2)_n R^2$, —$(CH_2)_n R^2 R^3$, —$SO_3H$, —$NO_2$, —$OR^2$, —$COR^2$, —$COOR^2$, —$(CH_2)_n OR^2$, —$CH(OH)R^2$, —$S(O)_m R^2$, —$SO_3 R^2$, —$CONH(R^2)_{2-m}$, —$SO_2 NH_m(R^2)^{2-m}$, $NH_m(R^2)_{2-m}$, —$CONHSO_3H$, —$(CH_2)_n R^5$, —$CH(OR^2)R^3$, —$(CH^2)_n R^2 R^5$, —$R^5$, —$OR^5$, —$COR^5$, —$COOR^5$, —$(CH_2)_n OR^5$, where m is an integer and where n is an integer from 1 to 4;

$R^2$ is selected from the group consisting of hydrogen, halogen, alkyl, —$CH_3$, hydroxyl, —$SO_3H$, —$NO_2$, $OR^3$, —$COR^3$, —$COOR^3$, —$CH(OR^3)R^4$, —$C(OH)R^3$, —$SO_3 R^3$, —$R^5$, —$OR^3 R^5$, $COR^5$, —$COR^3 R^5$, —$COR^3 R^4 R^5$, —$CH(OH)R^5$, —$S(O)_m R^3$, —$SO_3 R^3$, —$CONH_m(R^3)_{2-m}$, $NH_m(R^3)_{2-m}$, —$CONHSO_3H$, —$SO_2 NH_m(R^3)^{2-m}$, where m is an integer;

$R^3$ and $R^4$ are independently selected from the group consisting of hydrogen, halogen, hydroxyl, alkyl, —$CH_3$, —$SO_3H$, $NO_2$, and —$COOH$;

$R^5$ is a linker, and Z is a bridging group.

21. The device of claim 20, wherein the admixture further comprises at least one compound of formula

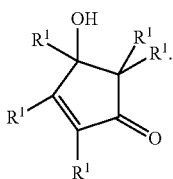

22. The device of claim 20, wherein the admixture comprises multiple racemates and/or diastereormers of the formula

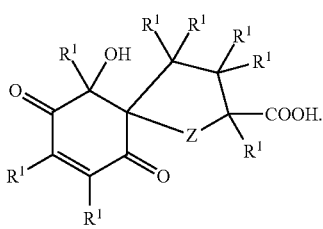

23. The device of claim 20, wherein the admixture comprises at least 10% of the compound having the formula

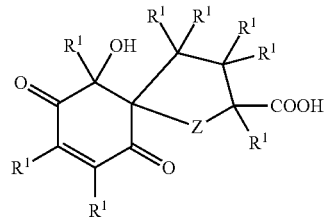

and no more than 50% of a compound of formula

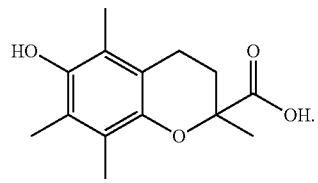 [SMILES: Cc1c(C)c2c(c(C)c1O)CCC(C)(C(=O)O)O2]

24. A photo-induced damage mitigating agent admixture comprising at least about 10% of a compound of formula,

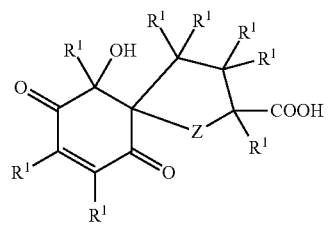

and no more than about 20% of a compound of formula

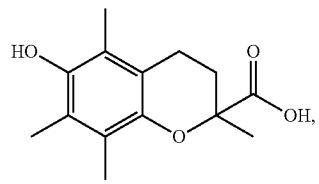

wherein $R^1$ is independently selected from the group consisting of hydrogen, halogen, alkyl, —$CH_3$, —$(CH_2)_n R^2$, —$(CH_2)_n R^2 R^3$, —$SO_3H$, —$NO_2$, —$OR^2$, —$COR^2$, —$COOR^2$, —$(CH_2)_n OR^2$, —$CH(OH)R^2$, —$S(O)_m R^2$, —$SO_3 R^2$, —$CONH_m(R^2)_{2-m}$, $SO_2 NH_m(R^2)^{2-m}$, $NH_m(R^2)_{2-m}$, —$CONHSO_3H$, —$(CH_2) R^5$, —$CH(OR^2)R^3$, $(CH_2)_n R^2 R^5$, —$R^5$, —$OR^5$, —$COR^5$, —$COOR^5$, —$(CH_2)_n OR^5$, where m is an integer and where n is an integer from 1 to 4;

$R^2$ is selected from the group consisting of hydrogen, halogen, alkyl, —$CH_3$, hydroxyl, —$SO_3H$, —$NO_2$, $OR^3$, —$COR^3$, —$COOR^3$, —$CH(OR^3)R^4$, —$C(OH)R^3$, —$SO_3 R^3$, —$R^5$, —$OR^3 R^5$, —$COR^5$, —$COR^3 R^5$, —$COR^3 R^4 R^5$, —$CH(OH)R^5$, —$S(O)_m R^3$, —$SO_3 R^3$, —$CONH_m(R^3)_{2-m}$, $NH_m (R^3)_{2-m}$, $CONHSO_3$, —$SO_2 NH_m(R^3)^{2-m}$, where m is an integer;

$R^3$ and $R^4$ are independently selected from the group consisting of hydrogen, halogen, hydroxyl alkyl, —$CH_3$, $SO_3H$, $NO_2$, and —$COOH$;

$R^5$ is a linker, and Z is a bridging group.

25. The method of claim 18, wherein the photo-induced damage mitigating agent admixture further comprises at least 10% of the compound of the formula
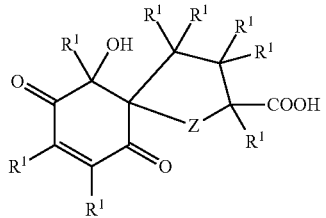
and no more than 50% of a compound of formula
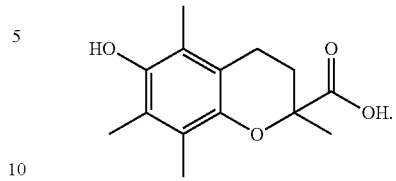
* * * * *